United States Patent
Kadow et al.

(10) Patent No.: US 10,407,410 B2
(45) Date of Patent: Sep. 10, 2019

(54) PYRIDIN-3-YL ACETIC ACID DERIVATIVES AS INHIBITORS OF HUMAN IMMUNODEFICIENCY VIRUS REPLICATION

(71) Applicant: ViiV HEALTHCARE UK (No.5) LIMITED, Brentford (GB)

(72) Inventors: John F. Kadow, Wallingford, CT (US); B. Narasimhulu Naidu, Wallingford, CT (US); Manoj Patel, Wallingford, CT (US); Michael A. Walker, Wallingford, CT (US); Tao Wang, Wallingford, CT (US); Zhiwei Yin, Wallingford, CT (US); Zhongxing Zhang, Wallingford, CT (US); Zhizhen Barbara Zheng, Wallingford, CT (US)

(73) Assignee: ViiV HEALTHCARE UK (NO.5) LIMITED, Brentford, Middlesex (GB)

( * ) Notice: Subject to any disclaimer, the term of this patent is extended or adjusted under 35 U.S.C. 154(b) by 0 days.

(21) Appl. No.: 16/094,536

(22) PCT Filed: May 9, 2017

(86) PCT No.: PCT/IB2017/052701
§ 371 (c)(1),
(2) Date: Oct. 18, 2018

(87) PCT Pub. No.: WO2017/195113
PCT Pub. Date: Nov. 16, 2017

(65) Prior Publication Data
US 2019/0127351 A1    May 2, 2019

Related U.S. Application Data

(60) Provisional application No. 62/334,718, filed on May 11, 2016.

(51) Int. Cl.
| | | |
|---|---|---|
| *C07D 401/14* | (2006.01) |
| *C07D 405/14* | (2006.01) |
| *C07D 413/14* | (2006.01) |
| *C07D 401/04* | (2006.01) |
| *C07D 407/14* | (2006.01) |
| *C07D 409/14* | (2006.01) |
| *C07D 417/14* | (2006.01) |
| *A61P 31/18* | (2006.01) |
| *A61K 31/4545* | (2006.01) |
| *A61K 31/4709* | (2006.01) |
| *A61K 31/4725* | (2006.01) |
| *A61K 31/5365* | (2006.01) |
| *C07D 411/14* | (2006.01) |

(52) U.S. Cl.
CPC ........ *C07D 401/14* (2013.01); *A61K 31/4545* (2013.01); *A61K 31/4709* (2013.01); *A61K 31/4725* (2013.01); *A61K 31/5365* (2013.01); *A61P 31/18* (2018.01); *C07D 401/04* (2013.01); *C07D 405/14* (2013.01); *C07D 407/14* (2013.01); *C07D 409/14* (2013.01); *C07D 411/14* (2013.01); *C07D 413/14* (2013.01); *C07D 417/14* (2013.01)

(58) Field of Classification Search
None
See application file for complete search history.

(56) References Cited

U.S. PATENT DOCUMENTS 9,193,720 B2 * 11/2015 Naidu .................. C07D 417/14

FOREIGN PATENT DOCUMENTS

| WO | WO 2010/130034 A1 | 11/2010 |
| WO | WO 2015/126776 A1 | 8/2015 |
| WO | WO 2017/025917 A1 | 2/2017 |
| WO | WO 2017/029631 A1 | 2/2017 |

* cited by examiner

*Primary Examiner* — Heidi Reese
(74) *Attorney, Agent, or Firm* — Robert H. Brink; Kathryn A. Lutomski; Edward R. Gimmi

(57) ABSTRACT

Disclosed are compounds of Formula I, including pharmaceutically acceptable salts, pharmaceutical compositions comprising the compounds, methods for making the compounds and their use in inhibiting HIV integrase and treating those infected with HIV or AIDS.

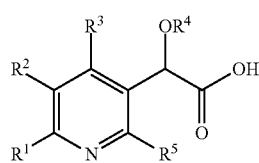

13 Claims, No Drawings

PYRIDIN-3-YL ACETIC ACID DERIVATIVES AS INHIBITORS OF HUMAN IMMUNODEFICIENCY VIRUS REPLICATION

This application is a § 371 of International Application No. PCT/IB2017/052701, filed 9 May 2017, which claims the benefit of U.S. Provisional Application No. 62/334,718, filed 11 May 2016.

FIELD OF THE INVENTION

The invention relates to compounds, compositions, and methods for the treatment of human immunodeficiency virus (HIV) infection. More particularly, the invention provides novel inhibitors of HIV, pharmaceutical compositions containing such compounds, and methods for using these compounds in the treatment of HIV infection. The invention also relates to methods for making the compounds hereinafter described.

BACKGROUND OF THE INVENTION

Human immunodeficiency virus (HIV) has been identified as the etiological agent responsible for acquired immune deficiency syndrome (AIDS), a fatal disease characterized by destruction of the immune system and the inability to fight off life threatening opportunistic infections. Recent statistics indicate that an estimated 35.3 million people worldwide are infected with the virus (UNAIDS: Report on the Global HIV/AIDS Epidemic, 2013). In addition to the large number of individuals already infected, the virus continues to spread. Estimates from 2013 point to close to 3.4 million new infections in that year alone. In the same year there were approximately 1.6 million deaths associated with HIV and AIDS.

Current therapy for HIV-infected individuals consists of a combination of approved anti-retroviral agents. Over two dozen drugs are currently approved for HIV infection, either as single agents or as fixed dose combinations or single tablet regimens, the latter two containing 2-4 approved agents. These agents belong to a number of different classes, targeting either a viral enzyme or the function of a viral protein during the virus replication cycle. Thus, agents are classified as either nucleotide reverse transcriptase inhibitors (NRTIs), non-nucleotide reverse transcriptase inhibitors (NNRTIs), protease inhibitors (PIs), integrase inhibitors (INIs), or entry inhibitors (one, maraviroc, targets the host CCR5 protein, while the other, enfuvirtide, is a peptide that targets the gp41 region of the viral gp160 protein). In addition, a pharmacokinetic enhancer with no antiviral activity, i.e., cobicistat, available from Gilead Sciences, Inc. under the tradename TYBOST™ (cobicistat) tablets, has recently been approved for use in combinations with certain antiretroviral agents (ARVs) that may benefit from boosting.

In the US, where combination therapy is widely available, the number of HIV-related deaths has dramatically declined (Palella, F. J.; Delany, K. M.; Moorman, A. C.; Loveless, M. O.; Furher, J.; Satten, G. A.; Aschman, D. J.; Holmberg, S. D. *N Engl. J. Med.* 1998, 338, 853-860).

Unfortunately, not all patients are responsive and a large number fail this therapy. In fact, initial studies suggest that approximately 30-50% of patients ultimately fail at least one drug in the suppressive combination. Treatment failure in most cases is caused by the emergence of viral resistance. Viral resistance in turn is caused by the replication rate of HIV-1 during the course of infection combined with the relatively high viral mutation rate associated with the viral polymerase and the lack of adherence of HIV-infected individuals in taking their prescribed medications. Clearly, there is a need for new antiviral agents, preferably with activity against viruses already resistant to currently approved drugs. Other important factors include improved safety and a more convenient dosing regimen than many of the currently approved drugs.

Compounds which inhibit HIV replication have been disclosed. See, for example, the following patent applications: WO2007131350, WO2009062285, WO2009062288, WO2009062289, WO2009062308, WO2010130034, WO2010130842, WO2011015641, WO2011076765, WO2012033735, WO2013123148, WO2013134113, WO2014164467, WO2014159959, and WO2015126726.

What is now needed in the art are additional compounds which are novel and useful in the treatment of HIV. Additionally, these compounds may desireably provide advantages for pharmaceutical uses, for example, with regard to one or more of their mechanisms of action, binding, inhibition efficacy, target selectivity, solubility, safety profiles, or bioavailability. Also needed are new formulations and methods of treatment which utilize these compounds.

SUMMARY OF THE INVENTION

The invention encompasses compounds of Formula I, including pharmaceutically acceptable salts thereof, as well as pharmaceutical compositions, and their use in inhibiting HIV and treating those infected with HIV or AIDS.

By virtue of the present invention, it is now possible to provide compounds that are novel and are useful in the treatment of HIV. Additionally, the compounds may provide advantages for pharmaceutical uses, for example, with regard to one or more of their mechanism of action, binding, inhibition efficacy, target selectivity, solubility, safety profiles, or bioavailability.

The invention also provides pharmaceutical compositions comprising the compounds of the invention, including pharmaceutically acceptable salts thereof, and a pharmaceutically acceptable carrier, excipient, and/or diluent.

In addition, the invention provides methods of treating HIV infection comprising administering a therapeutically effective amount of the compounds of the invention to a patient.

Also provided in accordance with the invention are methods for making the compounds of the invention.

The present invention is directed to these, as well as other important ends, hereinafter described.

DESCRIPTION OF THE INVENTION

Unless specified otherwise, these terms have the following meanings.

"Alkyl" means a straight or branched saturated hydrocarbon comprised of 1 to 10 carbons, and preferably 1 to 6 carbons.

"Alkenyl" means a straight or branched alkyl group comprised of 2 to 10 carbons with at least one double bond and optionally substituted with 0-3 halo or alkoxy group.

"Alkynyl" means a straight or branched alkyl group comprised of 2 to 10 carbons, preferably 2 to 6 carbons, containing at least one triple bond and optionally substituted with 0-3 halo or alkoxy group.

"Aryl" mean a carbocyclic group comprised of 1-3 rings that are fused and/or bonded and at least one or a combination of which is aromatic. The non-aromatic carbocyclic portion, where present, will be comprised of $C_3$ to $C_7$ alkyl group. Examples of aromatic groups include, but are not limited to indanyl, indenyl, naphthyl, phenyl, tetrahydronaphthyl and cyclopropylphenyl. The aryl group can be attached to the parent structure through any substitutable carbon atom in the group.

"Arylalkyl" is a $C_1$-$C_5$ alkyl group attached to 1 to 2 aryl groups and linked to the parent structure through the alkyl moiety. Examples include, but are not limited to, —$(CH_2)_n$Ph with n=1-5, —$CH(CH_3)$Ph, —$CH(Ph)_2$.

"Aryloxy" is an aryl group attached to the parent structure by oxygen.

"Cycloalkyl" means a monocyclic ring system composed of 3 to 7 carbons.

"Halo" includes fluoro, chloro, bromo, and iodo.

"Haloalkyl" and "haloalkoxy" include all halogenated isomers from monohalo to perhalo.

"Heteroaryl" is a subset of heterocyclic group as defined below and is comprised of 1-3 rings where at least one or a combination of which is aromatic and that the aromatic group contains at least one atom chosen from a group of oxygen, nitrogen or sulfur.

"Heterocyclyl or heterocyclic" means a cyclic group of 1-3 rings comprised of carbon and at least one other atom selected independently from oxygen, nitrogen and sulfur. The rings could be bridged, fused and/or bonded, through a direct or spiro attachment, with the option to have one or a combination thereof be aromatic. Examples include, but are not limited to, azaindole, azaindoline, azetidine, benzimidazole, bezodioxolyl, benzoisothiazole, benzothiazole, benzothiadiazole, benzothiophene, benzoxazole, carbazole, chroman, dihalobezodioxolyl, dihydrobenzofuran, dihydrobenzo[1,4]oxazine, 1,3-dihydrobenzo[c]thiophene 2,2-dioxide, 2,3-dihydrobenzo[d]isothiazole 1,1-dioxide, 3,4-dihydro-2H-pyrido[3,2-b][1,4]oxazine, 2,3-dihydro-1H-pyrrolo[3,4-c]pyridine and its regioisomeric variants, 6,7-dihydro-5H-pyrrolo[2,3-b]pyrazine and its regioisomeric variants, furanylphenyl, imidazole, imidazo[1,2-a]pyridine, indazole, indole, indoline, isoquinoline, isoquinolinone, isothiazolidine 1,1-dioxide, morpholine, 2-oxa-5-azabicyclo[2.2.1]heptane, oxadiazole-phenyl, oxazole, phenylaztidine, phenylindazole, phenylpiperidine, phenylpiperizine, phenyloxazole, phenylpyrrolidine, piperidine, pyridine, pyridinylphenyl, pyridinylpyrrolidine, pyrimidine, pyrimidinylphenyl, pyrrazole-phenyl, pyrrolidine, pyrrolidin-2-one, 1H-pyrazolo[4,3-c]pyridine and its regioisomeric variants, pyrrole, 5H-pyrrolo[2,3-b]pyrazine, 7H-pyrrolo[2,3-d]pyrimidine and its regioisomeric variants, quinazoline, quinoline, quinoxaline, tetrahydroisoquinoline, 1,2,3,4-tetrahydro-1,8-naphthyridine, tetrahydroquinoline, 4,5,6,7-tetrahydrothieno[3,2-c]pyridine, 1,2,5-thiadiazolidine 1,1-dioxide, thiophene, thiophenylphenyl, triazole, or triazolone. Unless otherwise specifically set forth, the heterocyclic group can be attached to the parent structure through any suitable atom in the group that results in a stable compound.

It is understood that a subset of the noted heterocyclic examples encompass regioisomers. For instance, "azaindole" refers to any of the following regioisomers: 1H-pyrrolo[2,3-b]pyridine, 1H-pyrrolo[2,3-c]pyridine, 1H-pyrrolo[3,2-c]pyridine, and 1H-pyrrolo[3,2-b]pyridine. In addition the "regioisomer variants" notation as in, for example, "5H-pyrrolo[2,3-b]pyrazine and its regioisomeric variants" would also encompass 7H-pyrrolo[2,3-d]pyrimidine, 7H-pyrrolo[2,3-c]pyridazine, 1H-pyrrolo[2,3-d]pyridazine, 5H-pyrrolo[3,2-c]pyridazine, and 5H-pyrrolo[3,2-d]pyrimidine. Similarly, 6,7-dihydro-5H-pyrrolo[2,3-b]pyrazine and its regioisomeric variants would encompass 6,7-dihydro-5H-pyrrolo[2,3-d]pyrimidine and 6,7-dihydro-5H-pyrrolo[2,3-c]pyridazine. It is also understood that the lack of "regioisomeric variants" notation does not in any way restrict the claim scope to the noted example only.

"Heterocyclylalkyl" is a heterocyclyl moiety attached to the parent structure through $C_1$-$C_5$ alkyl group. Examples include, but are not limited to, —$(CH_2)_n$—$R^Z$ or —CH$(CH_3)$—$(R^Z)$ where n=1-5 and that $R^Z$ is chosen from benzimidazole, imidazole, indazole, isooxazole, phenylpyrazole, pyridine, quinoline, thiazole, triazole, triazolone, oxadiazole.

Terms with a hydrocarbon moiety (e.g. alkoxy) include straight and branched isomers for the hydrocarbon portion with the indicated number of carbon atoms.

Bonding and positional bonding relationships are those that are stable as understood by practitioners of organic chemistry.

Parenthetic and multiparenthetic terms are intended to clarify bonding relationships to those skilled in the art. For example, a term such as ((R)alkyl) means an alkyl substituent further substituted with the substituent R.

Substituents which are illustrated by chemical drawing to bond at variable positions on a multiple ring system (for example a bicyclic ring system) are intended to bond to the ring where they are drawn to append. Parenthetic and multiparenthetic terms are intended to clarify bonding relationships to those skilled in the art. For example, a term such as ((R)alkyl) means an alkyl substituent further substituted with the substituent R.

"Combination," "coadministration," "concurrent" and similar terms referring to the administration of a compound of Formula I with at least one anti-HIV agent mean that the components are part of a combination antiretroviral therapy or highly active antiretroviral therapy ("HAART") as understood by practitioners in the field of AIDS and HIV infection.

"Therapeutically effective" means the amount of agent required to provide a benefit to a patient as understood by practitioners in the field of AIDS and HIV infection. In general, the goals of treatment are suppression of viral load, restoration and preservation of immunologic function, improved quality of life, and reduction of HIV-related morbidity and mortality.

"Patient" means a person infected with the HIV virus.

"Treatment," "therapy," "regimen," "HIV infection," "ARC," "AIDS" and related terms are used as understood by practitioners in the field of AIDS and HIV infection.

Those terms not specifically set forth herein shall have the meaning which is commonly understood and accepted in the art.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention exist in stereoisomeric forms. The invention includes all stereoisomeric forms of the compounds including enantiomers and diastereomers. Methods of making and separating stereoisomers are known in the art. The invention includes all tautomeric forms of the compounds. The invention includes atropisomers and rotational isomers.

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

In an aspect of the invention, there is provided a compound of Formula I:

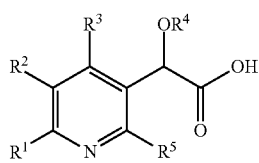

wherein:
$R^1$ is selected from hydrogen, alkyl, cycloalkyl, or hydroxyalkyl;
$R^2$ is selected from indanyl, tetrahydronaphthalinyl, indolyl, indolinyl, isoindolinyl, isoindolinonyl, benzofuranyl, benzothiophenyl, benzoimidazolonyl, chromanyl, quinolinyl, quinolinonyl, isoquinolinyl, tetrahydroisoquinolinonyl, dihydrobenzodioxinyl or benzoxazinyl, and is substituted with 0-1 $R^6$ substituent and also with 0-3 halo or alkyl substituents;
or $R^2$ is selected from hydroxydihydroquinolinonyl or bis-halobenzyldioxotetrahydroquinolinyl;
$R^3$ is selected from azetidinyl, pyrrolidinyl, piperidinyl, piperazinyl, morpholinyl, homopiperidinyl, homopiperazinyl, or homomorpholinyl, and is substituted with 0-3 substituents selected from cyano, halo, alkyl, haloalkyl, alkoxy, and haloalkoxy;
$R^4$ is selected from alkyl or haloalkyl;
$R^5$ is alkyl;
$R^6$ is selected from $(Ar^1)$alkyl, $((Ar^1)O)$alkyl, $(Ar^1)$alkenyl, hydroxy, alkoxy, $(Ar^1)O$, $(Ar^1)SO_2$, $(Ar^1)CO$, carboxy, or $Ar^1$; wherein $Ar^1$ is selected from phenyl, pyridinyl, or thiazolyl, and is substituted with 0-3 substituents selected from cyano, halo, alkyl, haloalkyl, alkoxy, and haloalkoxy;
or a pharmaceutically acceptable salt thereof.

For a particular compound of Formula I, the scope of any instance of a variable substituent, including $R^1$, $R^2$, $R^3$, $R^4$, $R^5$, $R^6$, and $Ar^1$ can be used independently with the scope of any other instance of a variable substituent. As such, the invention includes combinations of the different aspects.

In an aspect of the invention, $R^2$ is selected from indanyl, tetrahydronaphthalinyl, indolyl, indolinyl, isoindolinyl, isoindolinonyl, benzofuranyl, benzothiophenyl, benzoimidazolonyl, chromanyl, quinolinyl, quinolinonyl, isoquinolinyl, tetrahydroisoquinolinonyl, dihydrobenzodioxinyl or benzoxazinyl, and is substituted with 0-1 $R^6$ substituent and 0-3 halo or alkyl substituents. In an aspect of the invention, $R^2$ is selected from chromanyl substituted with 0-1 $R^6$ substituent and 0-3 halo or alkyl substituents. In an aspect of the invention, $R^2$ has 1 $R^6$ substituent and 0-3 halo or alkyl substituents. In an aspect of the invention, $R^3$ is piperidinyl substituted with 0-3 substituents selected from cyano, halo, alkyl, haloalkyl, alkoxy, and haloalkoxy. In an aspect of the invention, $R^6$ is selected from $(Ar^1)$alkyl, $((Ar^1)O)$alkyl, or $(Ar^1)$alkenyl. In an aspect of the invention, $R^6$ is selected from hydroxy, alkoxy, $(Ar^1)O$, $(Ar^1)SO_2$, $(Ar^1)CO$, or carboxy. In an aspect of the invention, $R^6$ is selected from phenyl, pyridinyl, or thiazolyl, and is substituted with 0-3 substituents selected from cyano, halo, alkyl, haloalkyl, alkoxy, and haloalkoxy.

In an aspect of the invention, there is provided a compound of Formula I:

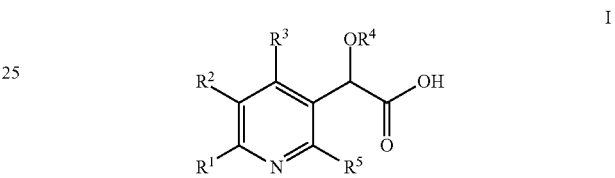

where:
$R^1$ is selected from hydrogen, alkyl, cycloalkyl, or hydroxyalkyl;
$R^2$ is selected from indanyl, tetrahydronaphthalinyl, indolyl, indolinyl, isoindolinyl, isoindolinonyl, benzofuranyl, benzothiophenyl, benzoimidazolonyl, chromanyl, quinolinyl, quinolinonyl, isoquinolinyl, tetrahydroisoquinolinonyl, dihydrobenzodioxinyl or benzoxazinyl, and is substituted with 0-1 $R^6$ substituent and 0-3 halo or alkyl substituents;
$R^3$ is selected from azetidinyl, pyrrolidinyl, piperidinyl, piperazinyl, morpholinyl, homopiperidinyl, homopiperazinyl, or homomorpholinyl, and is substituted with 0-3 substituents selected from cyano, halo, alkyl, haloalkyl, alkoxy, and haloalkoxy;
$R^4$ is selected from alkyl or haloalkyl;
$R^5$ is alkyl;
$R^6$ is selected from $(Ar^1)$alkyl, $((Ar^1)O)$alkyl, $(Ar^1)$alkenyl, hydroxy, alkoxy, $(Ar^1)O$, $(Ar^1)SO_2$, $(Ar^1)CO$, carboxy, or $Ar^1$; wherein $Ar^1$ is selected from phenyl, pyridinyl, or thiazolyl, and is substituted with 0-3 substituents selected from cyano, halo, alkyl, haloalkyl, alkoxy, and haloalkoxy;
or a pharmaceutically acceptable salt thereof.

In an aspect of the invention, $R^2$ is selected from tetrahydronaphthalinyl, isoindolinyl, isoindolinonyl, chromanyl, quinolinyl, quinolinonyl, isoquinolinyl and tetrahydroisoquinolinonyl, and is substituted with 0-1 $R^6$ substituent and 0-3 halo or alkyl substituents. In an aspect of the invention, $R^2$ is chromanyl substituted with 0-1 $R^6$ substituent and 0-3 halo or alkyl substituents. In an aspect of the invention, $R^2$ has 1 $R^6$ substituent and 0-3 halo or alkyl substituents. In an aspect of the invention, $R^3$ is piperidinyl substituted with 0-3 substituents selected from cyano, halo, alkyl, haloalkyl, alkoxy, and haloalkoxy. In an aspect of the invention, $R^6$ is selected from $(Ar^1)$alkyl, $((Ar^1)O)$alkyl, or $(Ar^1)$alkenyl. In an aspect of the invention, $R^6$ is selected from hydroxy, alkoxy, $(Ar^1)O$, $(Ar^1)SO_2$, $(Ar^1)CO$, or carboxy. In an aspect of the invention, $R^6$ is selected from phenyl, pyridinyl, or thiazolyl, and is substituted with 0-3 substituents selected from cyano, halo, alkyl, haloalkyl, alkoxy, and haloalkoxy.

In an aspect of the invention, there is provided a compound of Formula I:

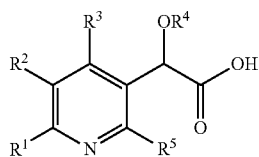

wherein:
$R^1$ is selected from hydrogen, alkyl, cycloalkyl, or hydroxyalkyl;
$R^2$ is selected from hydroxydihydroquinolinonyl or bis-halobenzyldioxotetrahydroquinolinyl;
$R^3$ is selected from azetidinyl, pyrrolidinyl, piperidinyl, piperazinyl, morpholinyl, homopiperidinyl, homopiperazinyl, or homomorpholinyl, and is substituted with 0-3 substituents selected from cyano, halo, alkyl, haloalkyl, alkoxy, and haloalkoxy;
$R^4$ is selected from alkyl or haloalkyl;
$R^5$ is alkyl;
$R^6$ is selected from $(Ar^1)$alkyl, $((Ar^1)O)$alkyl, $(Ar^1)$alkenyl, hydroxy, alkoxy, $(Ar^1)O$, $(Ar^1)SO_2$, $(Ar^1)CO$, carboxy, or $Ar^1$; wherein $Ar^1$ is selected from phenyl, pyridinyl, or thiazolyl, and is substituted with 0-3 substituents selected from cyano, halo, alkyl, haloalkyl, alkoxy, and haloalkoxy; or a pharmaceutically acceptable salt thereof.

In an aspect of the invention, $R^2$ has 1 $R^6$ substituent and 0-3 halo or alkyl substituents. In an aspect of the invention, $R^3$ is piperidinyl substituted with 0-3 substituents selected from cyano, halo, alkyl, haloalkyl, alkoxy, and haloalkoxy. In an aspect of the invention, $R^6$ is selected from $(Ar^1)$alkyl, $((Ar^1)O)$alkyl, or $(Ar^1)$alkenyl. In an aspect of the invention, $R^6$ is selected from hydroxy, alkoxy, $(Ar^1)O$, $(Ar^1)SO_2$, $(Ar^1)CO$, or carboxy. In an aspect of the invention, $R^6$ is selected from phenyl, pyridinyl, or thiazolyl, and is substituted with 0-3 substituents selected from cyano, halo, alkyl, haloalkyl, alkoxy, and haloalkoxy.

In an aspect of the invention, there is provided a composition useful for treating HIV infection comprising a therapeutic amount of a compound of Formula I and a pharmaceutically acceptable carrier. In an aspect of the invention, the composition further comprises a therapeutically effective amount at least one other agent used for treatment of AIDS or HIV infection selected from nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors, and a pharmaceutically acceptable carrier. In an aspect of the invention, the other agent is dolutegravir.

In an aspect of the invention, there is provided a method for treating HIV infection comprising administering a therapeutically effective amount of a compound of Formula I, or a pharmaceutically acceptable salt thereof, to a patient in need thereof. In an aspect of the invention, the method further comprises administering a therapeutically effective amount of at least one other agent used for treatment of AIDS or HIV infection selected from nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors. In an aspect of the invention, the other agent is dolutegravir. In an aspect of the invention, the other agent is administered to the patient prior to, simultaneously with, or subsequently to the compound of Formula I.

Preferred compounds in accordance with the present invention include the following:
(S)-2-(tert-butoxy)-2-(4-(4,4-dimethylpiperidin-1-yl)-5-(isoquinolin-7-yl)-2,6-dimethylpyridin-3-yl)acetic acid;
(S)-2-(tert-butoxy)-2-(4-(4,4-dimethylpiperidin-1-yl)-2,6-dimethyl-5-(quinolin-3-yl)pyridin-3-yl)acetic acid;
(S)-2-(tert-butoxy)-2-(5-(2,3-dihydrobenzo[b][1,4]dioxin-6-yl)-4-(4,4-dimethylpiperidin-1-yl)-2,6-dimethylpyridin-3-yl)acetic acid;
(S)-2-(tert-butoxy)-2-(4-(4,4-dimethylpiperidin-1-yl)-5-(1H-indol-6-yl)-2,6-dimethylpyridin-3-yl)acetic acid;
(S)-2-(tert-butoxy)-2-(5-(2,3-dihydro-1H-inden-5-yl)-4-(4,4-dimethylpiperidin-1-yl)-2,6-dimethylpyridin-3-yl)acetic acid;
(S)-5-(5-(tert-butoxy(carboxy)methyl)-4-(4,4-dimethylpiperidin-1-yl)-2,6-dimethylpyridin-3-yl)benzo[b]thiophene-2-carboxylic acid;
(2S)-2-(5-(benzofuran-3-yl)-4-(4,4-dimethylpiperidin-1-yl)-2,6-dimethylpyridin-3-yl)-2-(tert-butoxy)acetic acid;
(S)-2-(tert-butoxy)-2-(4-(4,4-dimethylpiperidin-1-yl)-2,6-dimethyl-5-(2-oxo-2,3-dihydro-1H-benzo[d]imidazol-5-yl)pyridin-3-yl)acetic acid;
(S)-2-(tert-butoxy)-2-(4-(4,4-dimethylpiperidin-1-yl)-2,6-dimethyl-5-(4-methyl-3,4-dihydro-2H-benzo[b][1,4]oxazin-7-yl)pyridin-3-yl)acetic acid;
(S)-2-(tert-butoxy)-2-(4-(4,4-dimethylpiperidin-1-yl)-2,6-dimethyl-5-(1-oxo-1,2,3,4-tetrahydroisoquinolin-6-yl)pyridin-3-yl)acetic acid;
(S)-2-(tert-butoxy)-2-(4-(4,4-dimethylpiperidin-1-yl)-2,6-dimethyl-5-(1-oxoisoindolin-5-yl)pyridin-3-yl)acetic acid;
(S)-2-(tert-butoxy)-2-(4-(4,4-dimethylpiperidin-1-yl)-5-(4-hydroxy-2-oxo-1,2-dihydroquinolin-6-yl)-2,6-dimethylpyridin-3-yl)acetic acid;
(S)-2-(tert-butoxy)-2-(4-(4,4-dimethylpiperidin-1-yl)-5-(2-(4-fluorobenzyl)-1-oxoisoindolin-5-yl)-2,6-dimethylpyridin-3-yl)acetic acid;
(S)-2-(tert-butoxy)-2-(4-(4,4-dimethylpiperidin-1-yl)-5-(2-(4-fluorobenzyl)-1-oxo-1,2,3,4-tetrahydroisoquinolin-6-yl)-2,6-dimethylpyridin-3-yl)acetic acid;
(S)-2-(tert-butoxy)-2-(4-(4,4-dimethylpiperidin-1-yl)-2,6-dimethyl-5-(1-oxo-2-(thiazol-2-ylmethyl)-1,2,3,4-tetrahydroisoquinolin-6-yl)pyridin-3-yl)acetic acid;
(S)-2-(tert-butoxy)-2-(4-(4,4-dimethylpiperidin-1-yl)-5-(4-((4-fluorobenzyl)oxy)-2-oxo-1,2-dihydroquinolin-6-yl)-2,6-dimethylpyridin-3-yl)acetic acid;
(S)-2-(5-(3,3-bis(4-fluorobenzyl)-2,4-dioxo-1,2,3,4-tetrahydroquinolin-6-yl)-4-(4,4-dimethylpiperidin-1-yl)-2,6-dimethylpyridin-3-yl)-2-(tert-butoxy)acetic acid;
(S)-2-(tert-butoxy)-2-(4-(4,4-dimethylpiperidin-1-yl)-5-(4-((4-fluorobenzyl)oxy)-1-methyl-2-oxo-1,2-dihydroquinolin-6-yl)-2,6-dimethylpyridin-3-yl)acetic acid;
(S)-2-(tert-butoxy)-2-(4-(4,4-dimethylpiperidin-1-yl)-2,6-dimethyl-5-(1-oxo-2-(thiazol-4-ylmethyl)-1,2,3,4-tetrahydroisoquinolin-6-yl)pyridin-3-yl)acetic acid;
(S)-2-(tert-butoxy)-2-(4-(4,4-dimethylpiperidin-1-yl)-2,6-dimethyl-5-(2-((4-methylthiazol-5-yl)methyl)-1-oxo-1,2,3,4-tetrahydroisoquinolin-6-yl)pyridin-3-yl)acetic acid;

(S)-2-(tert-butoxy)-2-(4-(4,4-dimethylpiperidin-1-yl)-5-(2-(4-fluorobenzyl)isoindolin-5-yl)-2,6-dimethylpyridin-3-yl)acetic acid;

(S)-2-(tert-butoxy)-2-(4-(4,4-dimethylpiperidin-1-yl)-5-(2-(4-fluorobenzoyl)isoindolin-5-yl)-2,6-dimethylpyridin-3-yl)acetic acid;

(S)-2-(tert-butoxy)-2-(4-(4,4-dimethylpiperidin-1-yl)-5-(2-((4-ethoxyphenyl)sulfonyl)isoindolin-5-yl)-2,6-dimethylpyridin-3-yl)acetic acid;

(S)-2-(tert-butoxy)-2-(4-(4,4-dimethylpiperidin-1-yl)-5-(2-((4-methoxyphenyl)sulfonyl)isoindolin-5-yl)-2,6-dimethylpyridin-3-yl)acetic acid;

(S)-2-(tert-butoxy)-2-(4-(4,4-dimethylpiperidin-1-yl)-5-(6-(4-fluorobenzylidene)-5,6,7,8-tetrahydronaphthalen-2-yl)-2,6-dimethylpyridin-3-yl)acetic acid;

(2S)-2-(tert-butoxy)-2-(4-(4,4-dimethylpiperidin-1-yl)-5-(6-(4-fluorobenzyl)-5,6,7,8-tetrahydronaphthalen-2-yl)-2,6-dimethylpyridin-3-yl)acetic acid;

(2S)-2-(tert-butoxy)-2-(4-(4,4-dimethylpiperidin-1-yl)-5-(6-(4-fluorophenoxy)-5,6,7,8-tetrahydronaphthalen-2-yl)-2,6-dimethylpyridin-3-yl)acetic acid;

(S)-2-(tert-butoxy)-2-(5-((S)-2-(3,4-difluorobenzyl)chroman-6-yl)-4-(4,4-dimethylpiperidin-1-yl)-2,6-dimethylpyridin-3-yl)acetic acid;

(S)-2-(tert-butoxy)-2-(5-((R)-2-(3,4-difluorobenzyl)chroman-6-yl)-4-(4,4-dimethylpiperidin-1-yl)-2,6-dimethylpyridin-3-yl)acetic acid;

(S)-2-(tert-butoxy)-2-(4-(4,4-dimethylpiperidin-1-yl)-5-((S)-2-(2-fluoro-4-methylbenzyl)chroman-6-yl)-2,6-dimethylpyridin-3-yl)acetic acid;

(S)-2-(tert-butoxy)-2-(4-(4,4-dimethylpiperidin-1-yl)-5-((R)-2-(2-fluoro-4-methylbenzyl)chroman-6-yl)-2,6-dimethylpyridin-3-yl)acetic acid;

(S)-2-(5-((S)-2-benzylchroman-6-yl)-4-(4,4-dimethylpiperidin-1-yl)-6-(hydroxymethyl)-2-methylpyridin-3-yl)-2-(tert-butoxy)acetic acid;

(S)-2-(5-((S)-2-benzylchroman-6-yl)-4-(4,4-dimethylpiperidin-1-yl)-6-(hydroxymethyl)-2-methylpyridin-3-yl)-2-(tert-butoxy)acetic acid;

(S)-2-(tert-butoxy)-2-(4-(4,4-dimethylpiperidin-1-yl)-5-((S)-2-(4-fluorobenzyl)chroman-6-yl)-2,6-dimethylpyridin-3-yl)acetic acid;

(S)-2-(tert-butoxy)-2-(4-(4,4-dimethylpiperidin-1-yl)-5-((R)-2-(4-fluorobenzyl)chroman-6-yl)-2,6-dimethylpyridin-3-yl)acetic acid;

(S)-2-(tert-butoxy)-2-(4-(4,4-dimethylpiperidin-1-yl)-5-((S)-2-(4-fluorobenzyl)chroman-6-yl)-6-(hydroxymethyl)-2-methylpyridin-3-yl)acetic acid;

(S)-2-(tert-butoxy)-2-(4-(4,4-dimethylpiperidin-1-yl)-5-((R)-2-(4-fluorobenzyl)chroman-6-yl)-6-(hydroxymethyl)-2-methylpyridin-3-yl)acetic acid;

(S)-2-(tert-butoxy)-2-(4-(4,4-dimethylpiperidin-1-yl)-5-((R)-2-(4-fluorobenzyl)-2-methylchroman-6-yl)-2,6-dimethylpyridin-3-yl)acetic acid;

(S)-2-(tert-butoxy)-2-(4-(4,4-dimethylpiperidin-1-yl)-5-((S)-2-(4-fluorobenzyl)-2-methylchroman-6-yl)-2,6-dimethylpyridin-3-yl)acetic acid;

(2S)-2-(tert-butoxy)-2-(4-(4,4-dimethylpiperidin-1-yl)-5-(2-((2-fluorophenoxy)methyl)chroman-6-yl)-2,6-dimethylpyridin-3-yl)acetic acid;

(2S)-2-(tert-butoxy)-2-(5-(2-((2,3-difluorophenoxy)methyl)chroman-6-yl)-4-(4,4-dimethylpiperidin-1-yl)-2,6-dimethylpyridin-3-yl)acetic acid;

(2S)-2-(tert-butoxy)-2-(4-(4,4-dimethylpiperidin-1-yl)-5-(2-(4-fluorophenyl)chroman-6-yl)-2,6-dimethylpyridin-3-yl)acetic acid;

(2S)-2-(tert-butoxy)-2-(4-(4,4-dimethylpiperidin-1-yl)-5-(2-(4-fluorophenyl)chroman-6-yl)-6-(hydroxymethyl)-2-methylpyridin-3-yl)acetic acid;

(2S)-2-(tert-butoxy)-2-(4-(4,4-dimethylpiperidin-1-yl)-2,6-dimethyl-5-(2-(6-methylpyridin-2-yl)chroman-6-yl)pyridin-3-yl)acetic acid; and (2S)-2-(tert-butoxy)-2-(4-(4,4-dimethylpiperidin-1-yl)-6-(hydroxymethyl)-2-methyl-5-(2-(6-methylpyridin-2-yl)chroman-6-yl)pyridin-3-yl)acetic acid or pharmaceutically acceptable salts thereof.

The compounds of the invention herein described may typically be administered as pharmaceutical compositions. These compositions are comprised of a therapeutically effective amount of a compound of Formula I or its pharmaceutically acceptable salt, and a pharmaceutically acceptable carrier and may contain conventional excipients and/or diluents. A therapeutically effective amount is that which is needed to provide a meaningful patient benefit. Pharmaceutically acceptable carriers are those conventionally known carriers having acceptable safety profiles. Compositions encompass all common solid and liquid forms, including capsules, tablets, lozenges, and powders, as well as liquid suspensions, syrups, elixirs, and solutions. Compositions are made using available formulation techniques, and excipients (such as binding and wetting agents) and vehicles (such as water and alcohols) which are generally used for compositions. See, for example, Remington's Pharmaceutical Sciences, 17th edition, Mack Publishing Company, Easton, Pa. (1985).

Solid compositions which are normally formulated in dosage units and compositions providing from about 1 to 1000 milligram ("mg") of the active ingredient per dose are typical. Some examples of dosages are 1 mg, 10 mg, 100 mg, 250 mg, 500 mg, and 1000 mg. Generally, other antiretroviral agents will be present in a unit range similar to agents of that class used clinically. Typically, this is about 0.25-1000 mg/unit.

Liquid compositions are usually in dosage unit ranges. Generally, the liquid composition will be in a unit dosage range of about 1-100 milligram per milliliter ("mg/mL"). Some examples of dosages are 1 mg/mL, 10 mg/mL, 25 mg/mL, 50 mg/mL, and 100 mg/mL. Generally, other antiretroviral agents will be present in a unit range similar to agents of that class used clinically. Typically, this is about 1-100 mg/mL.

The invention encompasses all conventional modes of administration; oral and parenteral methods are preferred. Generally, the dosing regimen will be similar to other antiretroviral agents used clinically. Typically, the daily dose will be about 1-100 milligram per kilogram ("mg/kg") body weight daily. Generally, more compound is required orally and less parenterally. The specific dosing regimen, however, will be determined by a physician using sound medical judgment.

The compounds of this invention desireably have activity against HIV. Accordingly, another aspect of the invention is a method for treating HIV infection in a human patient comprising administering a therapeutically effective amount of a compound of Formula I, or a pharmaceutically acceptable salt thereof, with a pharmaceutically acceptable carrier, excipient and/or diluent.

The invention also encompasses methods where the compound is given in combination therapy. That is, the compound can be used in conjunction with, but separately from, other agents useful in treating AIDS and HIV infection. The compound can also be used in combination therapy wherein the compound and one or more of the other agents are physically together in a fixed-dose combination (FDC). Some of these agents include HIV attachment inhibitors, CCR5 inhibitors, CXCR4 inhibitors, HIV cell fusion inhibitors, HIV integrase inhibitors, HIV nucleoside reverse transcriptase inhibitors, HIV non-nucleoside reverse transcriptase inhibitors, HIV protease inhibitors, budding and maturation inhibitors, HIV capsid inhibitors, anti-infectives, and immunomodulators, such as, for example, PD-1 inhibitors, PD-L1 inhinitors, antibodies, and the like. In these combination methods, the compound of Formula I will generally be given in a daily dose of about 1-100 mg/kg body weight daily in conjunction with other agents. The other agents generally will be given in the amounts used therapeutically. The specific dosing regimen, however, will be determined by a physician using sound medical judgment.

Examples of nucleoside HIV reverse transcriptase inhibitors include abacavir, didanosine, emtricitabine, lamivudine, stavudine, tenofovir, zalcitabine, and zidovudine.

Examples of non-nucleoside HIV reverse transcriptase inhibitors include delavirdine, efavirenz, etrivirine, nevirapine, and rilpivirine.

Examples of HIV protease inhibitors include amprenavir, atazanavir, darunavir, fosamprenavir, indinavir, lopinavir, nelfinavir, ritonavir, saquinavir and, tipranavir.

An example of an HIV fusion inhibitor is enfuvirtide or T-1249.

An example of an HIV entry inhibitor is maraviroc.

Examples of HIV integrase inhibitors include dolutegravir, elvitegravir, or raltegravir.

An example of an HIV attachment inhibitor is fostemsavir.

An example of an HIV maturation inhibitor is BMS-955176, having the following structure:

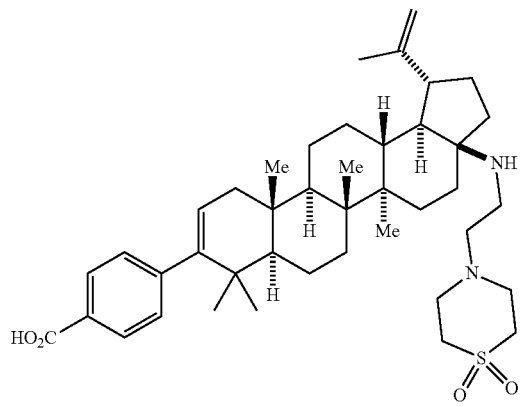

Thus, as set forth above, contemplated herein are combinations of the compounds of Formula I, together with one or more agents useful in the treatment of AIDS. For example, the compounds of the invention may be effectively administered, whether at periods of pre-exposure and/or post-exposure, in combination with effective amounts of the AIDS antivirals, immunomodulators, anti-infectives, or vaccines, such as those in the following non-limiting table:

| ANTIVIRALS | | |
|---|---|---|
| Drug Name | Manufacturer | Indication |
| Rilpivirine | Tibotec | HIV infection, AIDS, ARC (non-nucleoside reverse transcriptase inhibitor) |
| COMPLERA ® | Gilead | HIV infection, AIDS, ARC; combination with emtricitabine, rilpivirine, and tenofovir disoproxil fumarate |
| 097 | Hoechst/Bayer | HIV infection, AIDS, ARC (non-nucleoside reverse transcriptase (RT) inhibitor) |
| Amprenavir 141 W94 GW 141 | Glaxo Wellcome | HIV infection, AIDS, ARC (protease inhibitor) |
| Abacavir (1592U89) GW 1592 | Glaxo Wellcome | HIV infection, AIDS, ARC (RT inhibitor) |
| Acemannan | Carrington Labs (Irving, TX) | ARC |
| Acyclovir | Burroughs Wellcome | HIV infection, AIDS, ARC |
| AD-439 | Tanox Biosystems | HIV infection, AIDS, ARC |
| AD-519 | Tanox Biosystems | HIV infection, AIDS, ARC |
| Adefovir dipivoxil | Gilead Sciences | HIV infection |
| AL-721 | Ethigen (Los Angeles, CA) | ARC, PGL HIV positive, AIDS |
| Alpha Interferon | Glaxo Wellcome | Kaposi's sarcoma, HIV in combination w/Retrovir |
| Ansamycin LM 427 | Adria Laboratories (Dublin, OH) Erbamont (Stamford, CT) | ARC |

-continued

ANTIVIRALS

| Drug Name | Manufacturer | Indication |
|---|---|---|
| Antibody which Neutralizes pH Labile alpha aberrant Interferon | Advanced Biotherapy Concepts (Rockville, MD) | AIDS, ARC |
| AR177 | Aronex Pharm | HIV infection, AIDS, ARC |
| Beta-fluoro-ddA | Nat'l Cancer Institute | AIDS-associated diseases |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus Immune globin | MedImmune | CMV retinitis |
| Cytovene Ganciclovir | Syntex | Sight threatening CMV peripheral CMV retinitis |
| Darunavir | Tibotec-J & J | HIV infection, AIDS, ARC (protease inhibitor) |
| Delaviridine | Pharmacia-Upjohn | HIV infection, AIDS, ARC (RT inhibitor) |
| Dextran Sulfate | Ueno Fine Chem. Ind. Ltd. (Osaka, Japan) | AIDS, ARC, HIV positive asymptomatic |
| ddC Dideoxycytidine | Hoffman-La Roche | HIV infection, AIDS, ARC |
| ddI Dideoxyinosine | Bristol-Myers Squibb | HIV infection, AIDS, ARC; combination with AZT/d4T |
| DMP-450 | AVID (Camden, NJ) | HIV infection, AIDS, ARC (protease inhibitor) |
| Efavirenz (DMP 266, SUSTIVA ®) (−)6-Chloro-4-(S)-cyclopropylethynyl-4(S)-trifluoro-methyl-1,4-dihydro-2H-3,1-benzoxazin-2-one, STOCRINE | Bristol Myers Squibb | HIV infection, AIDS, ARC (non-nucleoside RT inhibitor) |
| EL10 | Elan Corp, PLC (Gainesville, GA) | HIV infection |
| Etravirine | Tibotec/J & J | HIV infection, AIDS, ARC (non-nucleoside reverse transcriptase inhibitor) |
| Famciclovir | Smith Kline | herpes zoster, herpes simplex |
| GS 840 | Gilead | HIV infection, AIDS, ARC (reverse transcriptase inhibitor) |
| HBY097 | Hoechst Marion Roussel | HIV infection, AIDS, ARC (non-nucleoside reverse transcriptase inhibitor) |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| ISIS 2922 | ISIS Pharmaceuticals | CMV retinitis |
| KNI-272 | Nat'l Cancer Institute | HIV-assoc. diseases |
| Lamivudine, 3TC | Glaxo Wellcome | HIV infection, AIDS, ARC (reverse transcriptase |

ANTIVIRALS -continued

| Drug Name | Manufacturer | Indication |
|---|---|---|
| | | inhibitor); also with AZT |
| Lobucavir | Bristol-Myers Squibb | CMV infection |
| Nelfinavir | Agouron Pharmaceuticals | HIV infection, AIDS, ARC (protease inhibitor) |
| Nevirapine | Boeheringer Ingleheim | HIV infection, AIDS, ARC (RT inhibitor) |
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc. | CMV retinitis, HIV infection, other CMV infections |
| PNU-140690 | Pharmacia Upjohn | HIV infection, AIDS, ARC (protease inhibitor) |
| Probucol | Vyrex | HIV infection, AIDS |
| RBC-CD4 | Sheffield Med. Tech (Houston, TX) | HIV infection, AIDS, ARC |
| Ritonavir | Abbott | HIV infection, AIDS, ARC (protease inhibitor) |
| Saquinavir | Hoffmann-LaRoche | HIV infection, AIDS, ARC (protease inhibitor) |
| Stavudine; d4T Didehydrodeoxy-Thymidine | Bristol-Myers Squibb | HIV infection, AIDS, ARC |
| Tipranavir | Boehringer Ingelheim | HIV infection, AIDS, ARC (protease inhibitor) |
| Valaciclovir | Glaxo Wellcome | Genital HSV & CMV Infections |
| Virazole Ribavirin | Viratek/ICN (Costa Mesa, CA) | asymptomatic HIV positive, LAS, ARC |
| VX-478 | Vertex | HIV infection, AIDS, ARC |
| Zalcitabine | Hoffmann-LaRoche | HIV infection, AIDS, ARC, with AZT |
| Zidovudine; AZT | Glaxo Wellcome | HIV infection, AIDS, ARC, Kaposi's sarcoma, in combination with other therapies |
| Tenofovir disoproxil, fumarate salt (VIREAD ®) | Gilead | HIV infection, AIDS, (reverse transcriptase inhibitor) |
| EMTRIVA ® (Emtricitabine) (FTC) | Gilead | HIV infection, AIDS, (reverse transcriptase inhibitor) |
| COMBIVIR ® | GSK | HIV infection, AIDS, (reverse transcriptase inhibitor) |
| Abacavir succinate (or ZIAGEN ®) | GSK | HIV infection, AIDS, (reverse transcriptase inhibitor) |
| REYATAZ ® (or atazanavir) | Bristol-Myers Squibb | HIV infection AIDs, protease inhibitor |
| FUZEON ® (Enfuvirtide or T-20) | Roche/Trimeris | HIV infection AIDs, viral Fusion inhibitor |
| LEXIVA ® (or Fosamprenavir calcium) | GSK/Vertex | HIV infection AIDs, viral protease inhibitor |
| SELZENTRY ™ Maraviroc; (UK 427857) | Pfizer | HIV infection AIDs, (CCR5 antagonist, in development) |

| ANTIVIRALS | | |
|---|---|---|
| Drug Name | Manufacturer | Indication |
| TRIZIVIR ® | GSK | HIV infection AIDs, (three drug combination) |
| Sch-417690 (vicriviroc) | Schering-Plough | HIV infection AIDs, (CCR5 antagonist, in development) |
| TAK-652 | Takeda | HIV infection AIDs, (CCR5 antagonist, in development) |
| GSK 873140 (ONO-4128) | GSK/ONO | HIV infection AIDs, (CCR5 antagonist, in development) |
| Integrase Inhibitor MK-0518 Raltegravir | Merck | HIV infection AIDs |
| TRUVADA ® | Gilead | Combination of Tenofovir disoproxil fumarate salt (VIREAD ®) and EMTRIVA ® (Emtricitabine) |
| Integrase Inhibitor GS917/JTK-303 Elvitegravir | Gilead/Japan Tobacco | HIV Infection AIDs in development |
| Triple drug combination ATRIPLA ® | Gilead/Bristol-Myers Squibb | Combination of Tenofovir disoproxil fumarate salt (VIREAD ®), EMTRIVA ® (Emtricitabine), and SUSTIVA ® (Efavirenz) |
| FESTINAVIR ® | Oncolys BioPharma | HIV infection AIDs in development |
| CMX-157 Lipid conjugate of nucleotide tenofovir | Chimerix | HIV infection AIDs |
| GSK1349572 Integrase inhibitor TIVICAY ® dolutegravir | GSK | HIV infection AIDs |

| IMMUNOMODULATORS | | |
|---|---|---|
| Drug Name | Manufacturer | Indication |
| AS-101 | Wyeth-Ayerst | AIDS |
| Bropirimine | Pharmacia Upjohn | Advanced AIDS |
| Acemannan | Carrington Labs, Inc. (Irving, TX) | AIDS, ARC |
| CL246,738 | Wyeth Lederle Labs | AIDS, Kaposi's sarcoma |
| FP-21399 | Fuki ImmunoPharm | Blocks HIV fusion with CD4+ cells |
| Gamma Interferon | Genentech | ARC, in combination w/TNF (tumor necrosis factor) |
| Granulocyte Macrophage Colony Stimulating Factor | Genetics Institute Sandoz | AIDS |
| Granulocyte Macrophage Colony Stimulating Factor | Hoechst-Roussel Immunex | AIDS |
| Granulocyte Macrophage Colony Stimulating Factor | Schering-Plough | AIDS, combination w/AZT |
| HIV Core Particle Immunostimulant | Rorer | Seropositive HIV |
| IL-2 Interleukin-2 | Cetus | AIDS, in combination w/AZT |
| IL-2 Interleukin-2 | Hoffman-LaRoche Immunex | AIDS, ARC, HIV, in combination w/AZT |
| IL-2 Interleukin-2 (aldeslukin) | Chiron | AIDS, increase in CD4 cell counts |
| Immune Globulin Intravenous (human) | Cutter Biological (Berkeley, CA) | Pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma |
| Granulocyte Colony Stimulating Factor | Amgen | AIDS, in combination w/AZT |
| Remune | Immune Response Corp. | Immunotherapeutic |
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |

-continued

IMMUNOMODULATORS

| Drug Name | Manufacturer | Indication |
|---|---|---|
| Interferon Alfa 2a | Hoffman-La Roche | Kaposi's sarcoma AIDS, ARC, in combination w/AZT |
| SK&F106528 Soluble T4 | Smith Kline | HIV infection |
| Thymopentin | Immunobiology Research Institute (Annandale, NJ) | HIV infection |
| Tumor Necrosis Factor; TNF | Genentech | ARC, in combination w/gamma Interferon |

ANTI-INFECTIVES

| Drug Name | Manufacturer | Indication |
|---|---|---|
| Clindamycin with Primaquine | Pharmacia Upjohn | PCP |
| Fluconazole | Pfizer | Cryptococcal meningitis, candidiasis |
| Pastille Nystatin Pastille | Squibb Corp. | Prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | Antibacterial |
| Trimethoprim/sulfa | | Antibacterial |
| Piritrexim | Burroughs Wellcome | PCP treatment |
| Pentamidine Isethionate for Inhalation | Fisons Corporation | PCP prophylaxis |
| Spiramycin | Rhone-Poulenc | Cryptosporidial diarrhea |
| Intraconazole-R51211 | Janssen-Pharm. | Histoplasmosis; cryptococcal meningitis |
| Trimetrexate | Warner-Lambert | PCP |
| Daunorubicin | NeXstar, Sequus | Kaposi's sarcoma |
| Recombinant Human Erythropoietin | Ortho Pharm. Corp. | Severe anemia assoc. with AZT therapy |
| Recombinant Human Growth Hormone | Serono | AIDS-related wasting, cachexia |
| Megestrol Acetate | Bristol-Myers Squibb | Treatment of anorexia assoc. W/AIDS |
| Testosterone | Alza, Smith Kline | AIDS-related wasting |
| Total Enteral Nutrition | Norwich Eaton Pharmaceuticals | Diarrhea and malabsorption related to AIDS |

Methods of Synthesis

The compounds of this invention can be made by various methods known in the art including those of the following schemes and in the specific embodiments section. The structure numbering and variable numbering shown in the synthetic schemes are distinct from, and should not be confused with, the structure or variable numbering in the claims or the rest of the specification. The variables in the schemes are meant only to illustrate how to make some of the compounds of this invention. The disclosure is not limited to the foregoing illustrative examples and the examples should be considered in all respects as illustrative and not restrictive, reference being made to the appended claims, rather than to the foregoing examples, and all changes which come within the meaning and range of equivalency of the claims are therefore intended to be embraced.

Abbreviations used in the schemes and examples generally follow conventions used in the art. Chemical abbreviations used in the specification and examples are defined as follows: "KHMDS" for potassium bis(trimethylsilyl)amide; "DMF" for N,N-dimethylformamide; "HATU" for O-(t-Azabenzotriazol-1-yl)-N,N,N',N'-tetramethyluronium hexafluorophosphate, "MeOH" for methanol; "Ar" for aryl; "TFA" for trifluoroacetic acid, "DMSO" for dimethylsulfoxide; "h" for hours; "rt" for room temperature or retention time (context will dictate); "min" for minutes; "EtOAc" for ethyl acetate; "THF" for tetrahydrofuran; "Et$_2$O" for diethyl ether; "DMAP" for 4-dimethylaminopyridine; "DCE" for 1,2-dichloroethane; "ACN" for acetonitrile; "DME" for 1,2-dimethoxyethane; "HOBt" for 1-hydroxybenzotriazole hydrate; and "DIEA" for diisopropylethylamine.

Certain other bbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "mmol" for millimole or millimoles, "atm" for atmosphere, "psi" for pounds per square inch, "conc." for concentrate, "sat" or "sat'd" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Some compounds of this invention can be prepared by the methods outlined in the Scheme I

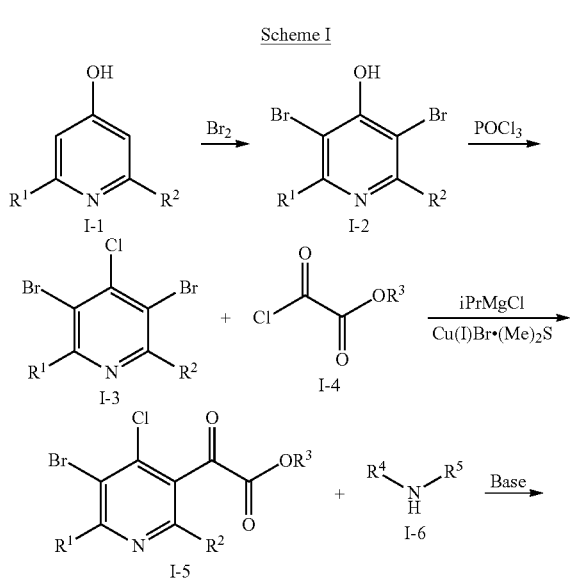

Scheme I

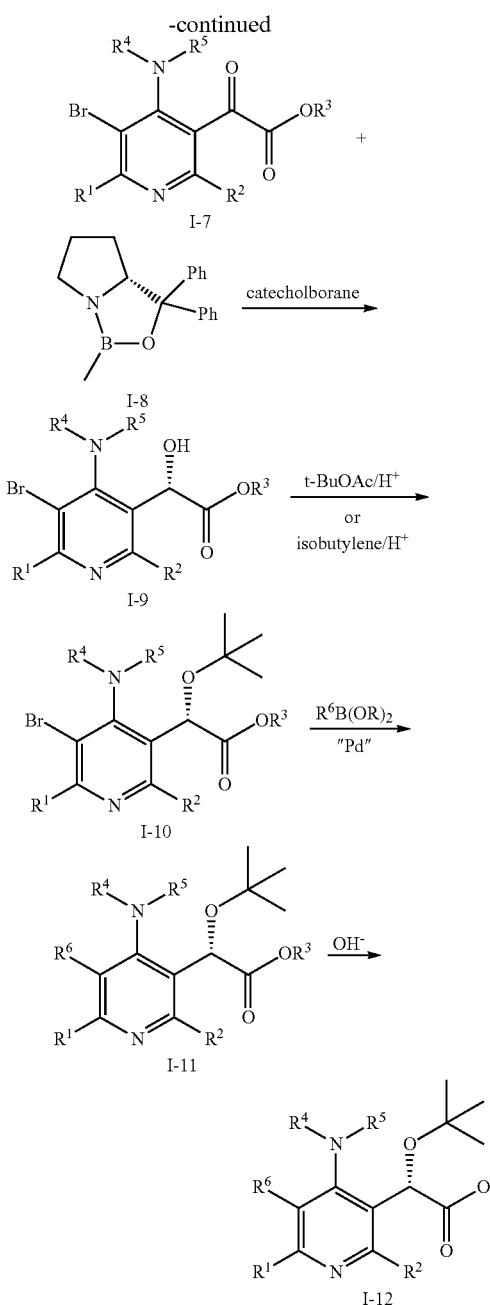

EXAMPLES

The following examples are provided by way of illustration only, and should not be construed as limiting the scope of the invention.

The compounds of the invention according to the various aspects can be made, for example, accorfing to the specific examples which follow. The structure numbering and variable numbering shown in the examples may be distinct from, and should not be confused with, the structure or variable numbering in the claims or the rest of the specification. The variables in the examples are meant only to illustrate how to make some of the compounds of the invention.

The compounds described herein were purified by the methods well known to those skilled in art by normal phase column chromatography on silica gel column using appropriate solvent system described. Preparative HPLC purifications mentioned in this experimentation section were carried out gradient elution either on Sunfire Prep C18 ODB column (5 μm; 19 or 30×100 mm) or Waters Xbridge C18 column (5 μM; 19×200 or 30×100 mm) or Water Atlantis (5 μm; 19 or 30×100 mm) using the following mobile phases. Mobile phase A: 9:1 $H_2O$/acetonitrile with 10 mM $NH_4OAc$ and mobile phase B:A: 9:1 acetonitrile/$H_2O$ with 10 mM $NH_4OAc$; or mobile phase A: 9:1 $H_2O$/acetonitrile with 0.1% TFA and mobile phase B:A: 9:1 acetonitrile/$H_2O$ with 0.1% TFA; or mobile phase A: water/MeOH (9:1) with 20 mM $NH_4OAc$ and mobile phase B: 95:5 MeOH/$H_2O$ with 20 mM $NH_4OAc$ or mobile phase A: water/MeOH (9:1) with 0.1% TFA and mobile phase B: 95:5 MeOH/$H_2O$ with 0.1% TFA or mobile Phase A: 5:95 acetonitrile: water with 10-mM ammonium acetate; Mobile Phase B: 95:5 acetonitrile: water with 10-mM ammonium acetate.

All Liquid Chromatography (LC) data were recorded on a Shimadzu LC-10AS or LC-20AS liquid chromotograph using a SPD-10AV or SPD-20A UV-Vis detector and Mass Spectrometry (MS) data were determined with a Micromass Platform for LC in electrospray mode.

Compounds purified by preparative HPLC were diluted in methanol (1.2 mL) or DMF and purified using a Shimadzu LC-8A or LC-10A automated preparative HPLC system.

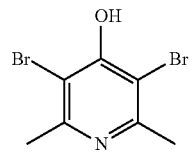

3,5-Dibromo-2,6-dimethylpyridin-4-ol

A 3-neck R.B-flask equipped with mechanical stirrer, addition funnel and condenser is charged with 2,6-dimethylpyridin-4-ol (100 g, 812 mmol), $CH_2Cl_2$ (1000 mL) and MeOH (120 mL). To the resulting light brown or tan solution was added tert-BuNH2 (176 ml, 1665 mmol), cooled in water bath maintained between 5-10° C. (ice-water) and added drop wise Br2 (84 ml, 1624 mmol) over 70 min. After the addition was complete cold bath was removed and stirred for 1.5 h at rt. Then, the light orange slurry was filtered and the filter cake was washed with ether (250 mL) and dried to afford 3,5-dibromo-2,6-dimethylpyridin-4-ol, hydrobromide (280.75 g, 776 mmol, 96% yield) as white solid which was used in the next step without further purification. $^1$H NMR (500 MHz, DMSO-$d_6$) δ 12.08 (br. s., 1H), 2.41 (s, 6H). LCMS (M+H)=281.9.

Alternative Procedure:

Bromine (72.8 mL, 1.4 mol) was added via addition funnel over 60 min to a mechanically stirred cold (ice-water bath) solution of 2,6-dimethylpyridin-4-ol (87 g, 706 mmol) and 4-methylmorpholine (156 mL, 1.4 mol) in dichloromethane (1 L) and methanol (100 mL) and then stirred for 2 h at rt. Additional bromine (~15 mL) was added based on monitoring by LCMS. The product was filtered, washed with ether, and dried under vacuum to give 3,5-dibromo-2, 6-dimethylpyridin-4-ol 176.8 g (88%).

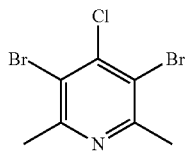

3,5-Dibromo-4-chloro-2,6-dimethylpyridine

Triethylamine (28.8 mL, 206 mmol) was added to a nitrogen purged solution of 3,5-dibromo-2,6-dimethylpyridin-4-ol (58 g, 206 mmol) and phosphorous oxychloride (57.7 mL, 619 mmol) in chloroform (450 mL) and stirred for 1 h at rt, then 3 h at 80° C. The reaction was removed from heating and immediately concentrated under house vaccum; then under high vacuum. The appearance was a cream colored solid, which was azeotroped with toluene (2×100 mL); treated with ice (200 g) for 10 min and carefully neutralized with NaHCO₃ (powder), and 1N NaOH solution, and extracted with DCM (2×400 mL). The combined organic layers were dried (MgSO₄), concentrated, and a beige solid was obtained that was washed with hexanes and dried under high vacuum to give 3,5-dibromo-4-chloro-2,6-dimethyl-pyridine 52.74 g (85.1%). Concentration of the hexanes gave 3.5 g of less pure product. $^1$H NMR (500 MHz, CDCl₃) δ 2.59 (s, 6H). LCMS (M+H)=300.0.

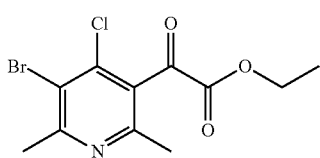 [SMILES: CCOC(=O)C(=O)c1c(C)nc(C)c(Br)c1Cl]

Ethyl 2-(5-bromo-4-chloro-2,6-dimethylpyridin-3-yl)-2-oxoacetate

To a stirred mixture of 3,5-dibromo-4-chloro-2,6-dimethylpyridine (14.94 g, 49.9 mmol) and Cu(I)Br Me2S (0.513 g, 2.495 mmol) in THF (50 mL) was added drop wise 2M iPrMgCl/THF (26.2 ml, 52.4 mmol) at −30° C. over 5 min. Then, the resulting slurry was warmed to −10° C. over 30 min and stirred for 30 min. The homogeneous brown reaction mixture was rapidly transferred via cannula to a solution of ethyl 2-chloro-2-oxoacetate (6.14 ml, 54.9 mmol, degassed for 5 min by bubbling N2 through the solution) in THF (50 mL) maintained at −30° C. The resulting reaction mixture was stirred (1.5 h) while warming to 0° C. Then, taken up in to Et₂O (200 mL), washed with 1:1 sat Na₂CO₃/1M NH₄Cl (3×50 mL), dried (MgSO₄), filtered and concentrated to give brown viscous oil. Flash chromatography using 2.5, 5 and 7.5% EtOAc/Hex afforded ethyl 2-(5-bromo-4-chloro-2,6-dimethylpyridin-3-yl)-2-oxoacetate (14.37 g, 44.8 mmol, 90% yield) as white solid. $^1$H NMR (400 MHz, CDCl₃) δ 4.42 (q, J=7.0 Hz, 2H), 2.76 (s, 3H), 2.46 (s, 3H), 1.41 (t, J=7.2 Hz, 3H). LCMS (M+H)=322.1.

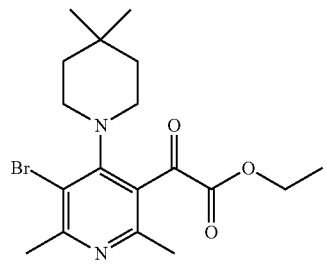 [SMILES: CCOC(=O)C(=O)c1c(C)nc(C)c(Br)c1N1CCC(C)(C)CC1]

Ethyl 2-(5-bromo-4-(4,4-dimethylpiperidin-1-yl)-2,6-dimethylpyridin-3-yl)-2-oxoacetate To a solution of 4,4-dimethylpiperidine (1.245 g, 11.00 mmol) and DIEA (3.49 ml, 20.00 mmol) in anhydrous CH₃CN (40 mL) was added ethyl 2-(5-bromo-4-chloro-2,6-dimethylpyridin-3-yl)-2-oxoacetate (3.21 g, 10 mmol) at rt. The resulting mixture was placed in a pre-heated oil bath (80° C.). After 22 h, the reaction mixture was concentrated and the residue was purified by flash chromatography using 1-lit each 2.5, 5, 7.5 and 10% EtOAc/Hex to afford ethyl 2-(5-bromo-4-(4,4-dimethylpiperidin-1-yl)-2,6-dimethyl-pyridin-3-yl)-2-oxoacetate (2.846 g, 7.16 mmol, 71.6% yield) as yellow solid. $^1$H NMR (500 MHz, CDCl₃) δ 4.37 (q, J=7.1 Hz, 2H), 3.67-2.75 (br.s., 4H), 2.71 (s, 3H), 2.44 (s, 3H), 1.42 (t, J=7.1 Hz, 3H), 1.38 (t, J=5.6 Hz, 4H), 1.00 (s, 6H). LCMS (M+H)=399.4.

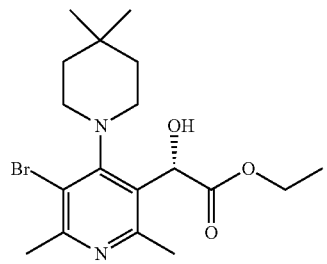 [SMILES: CCOC(=O)[C@@H](O)c1c(C)nc(C)c(Br)c1N1CCC(C)(C)CC1]

(S)-Ethyl 2-(5-bromo-4-(4,4-dimethylpiperidin-1-yl)-2,6-dimethylpyridin-3-yl)-2-hydroxyacetate To stirred yellow solution of ethyl 2-(5-bromo-4-(4,4-dimethylpiperidin-1-yl)-2,6-dimethylpyridin-3-yl)-2-oxoacetate (2.25 g, 5.66 mmol) and (R)-1-methyl-3,3-diphenyl-hexahydropyrrolo[1,2-c][1,3,2]oxazaborole (0.314 g, 1.133 mmol) in toluene (30 mL) at −35° C. was added drop wise 50% catecholborane (1.819 ml, 8.49 mmol) over 10 min. The reaction mixture was slowly warmed to −15° C. over 1 h and then left for 2 h at −15° C. Then, diluted with EtOAc (100 mL), washed with sat Na₂CO₃ (4×25 mL) by vigorously stirring and separating aqueous layers. The organic layer dried (MgSO₄), filtered, concentrated and purified by flash chromatography using 10, 20 and 25% EtOAc/Hex to afford desired (S)-ethyl 2-(5-bromo-4-(4,4-dimethylpiperidin-1-yl)-2,6-dimethylpyridin-3-yl)-2-hydroxyacetate (2.2596 g, 5.66 mmol, 100% yield) contaminated with about 10% of (S)-ethyl 2-(5-bromo-4-chloro-2,6-dimethylpyridin-3-yl)-2-hydroxyacetate. Used in the next step without further purification. $^1$H NMR (500 MHz, CDCl₃) δ 5.71 (d, J=7.3 Hz, 1H), 5.54 (d, J=7.4 Hz, 1H), 4.29 (dq, J=10.8, 7.1

Hz, 1H), 4.16 (dq, J=10.8, 7.1 Hz, 1H), 3.94-3.83 (m, 2H), 2.71 (d, J=11.9 Hz, 1H), 2.67 (s, 3H), 2.59 (s, 3H), 2.54 (d, J=12.0 Hz, 1H), 1.71 (td, J=12.7, 4.7 Hz, 1H), 1.62 (td, J=13.0, 4.7 Hz, 1H), 1.42 (dd, J=13.1, 2.2 Hz, 1H), 1.37 (dd, J=12.9, 2.4 Hz, 1H), 1.25 (t, J=7.1 Hz, 3H), 1.09 (s, 3H), 1.04 (s, 3H). LCMS (M+H)=401.3.

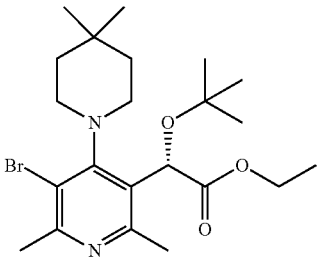 [SMILES: CCOC(=O)[C@@H](OC(C)(C)C)c1c(C)nc(C)c(Br)c1N1CCC(C)(C)CC1]

(S)-Ethyl 2-(5-bromo-4-(4,4-dimethylpiperidin-1-yl)-2,6-dimethylpyridin-3-yl)-2-(tert-butoxy)acetate A stirred ice-cold yellow mixture of (S)-ethyl 2-(5-bromo-4-(4,4-dimethylpiperidin-1-yl)-2,6-dimethylpyridin-3-yl)-2-hydroxyacetate (2.45 g, 6.14 mmol) and 70% HClO$_4$ (1.054 ml, 12.27 mmol) in CH$_2$Cl$_2$ (100 mL) was saturated with isobutylene gas by bubbling through the reaction mixture (10 min). After 2 h, cold bath was removed and the turbid reaction mixture stirred for 22 h at rt. LCMS at this point showed 4:1 product to sm. So, saturated with isobutylene (5 min) at rt and stirred for additional 24 h. Then, neutralized with sat. Na$_2$CO$_3$ (30 mL), organic layer separated and aqueous layer extracted with CH$_2$Cl$_2$ (25 mL). The combined organic layers dried (MgSO$_4$), filtered, concentrated and purified by flash chromatography using 5, 10, 15, 20 and 40% EtOAc/hex to afford (S)-ethyl 2-(5-bromo-4-(4,4-dimethylpiperidin-1-yl)-2,6-dimethylpyridin-3-yl)-2-(tert-butoxy)acetate (2.3074 g, 5.07 mmol, 83% yield) as yellow oil: $^1$H NMR (500 MHz, CDCl$_3$) δ 6.19 (br. s., 1H), 4.17-4.24 (m, 1H), 4.08-4.14 (m, 1H), 4.04 (dt, J=2.5, 12.1 Hz, 1H), 3.51 (dt, J=2.5, 12.1 Hz, 1H), 2.85-2.91 (m, 1H), 2.64 (s, 3H), 2.57-2.62 (m, 1H), 2.55 (s, 3H), 1.55-1.66 (m, 2H), 1.41-1.46 (m, 1H), 1.32-1.37 (m, 1H), 1.21 (s, 9H), 1.20 (t, J=7.2 Hz, 2H), 1.08 (s, 3H), 1.03 (s, 3H). LCMS (M+H)=457.4. And (S)-ethyl 2-(5-bromo-4-(4,4-dimethylpiperidin-1-yl)-2,6-dimethylpyridin-3-yl)-2-hydroxyacetate (0.3 g, 0.751 mmol, 12.24% yield) as pale yellow paste: LCMS (M+H)=401.3.

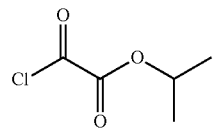

Isopropyl 2-chloro-2-oxoacetate

The propan-2-ol (38.2 mL, 499 mmol) was added drop wise over 15 min to a cold (0° C.), nitrogen purged solution of oxalyl dichloride (101 g, 799 mmol) and the reaction was stirred at room temperature for 2.5 h. Then a reflux condenser was fitted and a slight vacuum was applied for about 1 h until HCl gas was removed (the HCl was trapped in by a sat'd solution of NaHCO$_3$). The reflux condenser was removed and the flask was fitted with a short path distillation head. Excess reagent was removed by distillation under house vacuum (oil bath heated to 65° C.), and then the temperature was raised to between 85-95° C. and the product was distilled (NOTE: The 1$^{st}$ fraction of ~5 mL was discarded) to provide isopropyl 2-chloro-2-oxoacetate 52.62 g (70%).

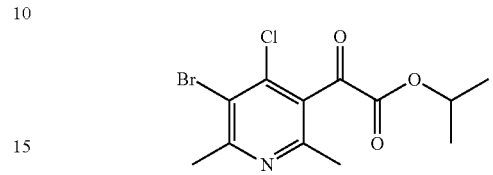

Isopropyl 2-(5-bromo-4-chloro-2,6-dimethylpyridin-3-yl)-2-oxoacetate

A solution of 2M isopropyl magnesium chloride (84 mL, 168 mmol) was added drop wise over 20 min to a cold (−70° C.), nitrogen purged solution of 3,5-dibromo-4-chloro-2,6-dimethylpyridine (48 g, 160 mmol) and copper(I)bromide-dimethyl sulfide complex (1.65 g, 8.02 mmol) in THF (240 mL), which was then allowed to warm to −10° C. over 60 min. The reaction mixture was transferred via cannula into a 1 L RB-flask containing isopropyl 2-chloro-2-oxoacetate (26.6 g, 176 mmol) in THF (160 mL) maintained at −60° C., and the reaction stirred an additional 2.5 h while being allowed to warm to −10° C. The reaction was quenched upon diluted with a mixture of 10% NH$_4$Cl solution (80 mL) in ether (320 mL). The organic layer was washed with 160 mL of sat'd NaHCO$_3$/10% NH$_4$Cl solution (1:1), brine, and dried (Na$_2$SO$_4$). The crude product was charged (DCM solution) to a 330 g ISCO silica gel cartridge and gradient eluted (5-20% EtOAc/hexanes) using an Isolera chromatography station gave isopropyl 2-(5-bromo-4-chloro-2,6-dimethylpyridin-3-yl)-2-oxoacetate 40.38 g (76%). $^1$H NMR (500 MHz, CDCl$_3$) δ 5.28-5.21 (m, 1H), 2.77 (s, 3H), 2.47 (s, 3H), 1.40 (d, J=6.3 Hz, 6H). LCMS (M+H)=336.04.

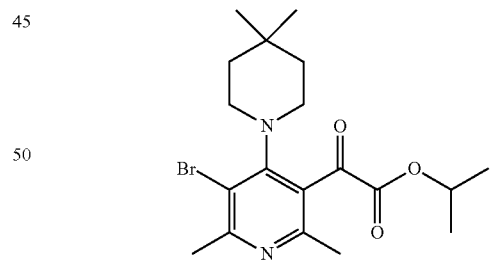

Isopropyl 2-(5-bromo-4-(4,4-dimethylpiperidin-1-yl)-2,6-dimethylpyridin-3-yl)-2-oxoacetate To a stirred solution of isopropyl 2-(5-bromo-4-chloro-2,6-dimethylpyridin-3-yl)-2-oxoacetate (7.2 g, 21.52 mmol) and DIEA (4.13 mL, 23.67 mmol) in anhydrous acetonitrile (15 mL) was added 4,4-dimethylpiperidine (2.68 g, 23.67 mmol) in acetonitrile (15 mL). The resulting solution was placed in a pre-heated oil bath at 75° C. After heating (75-78° C.) for 24 h, the temperature was raised to 85° C. for 24 h. Another portion of DIEA (3.5 mL, 20.04 mmol) and 4,4-dimethylpiperidine (0.27 g, 2.4 mmol) in acetonitrile (3 mL) was added and hearted at 85° C. for a day. The reaction mixture was diluted with ether (100 mL), washed with water (100 mL), brine (50 mL), dried (MgSO$_4$), filtered, concentrated and purified by ISCO 120 g cartridge (EtOAc/hex: 0 to 20%) to afford isopropyl 2-(5-bromo-4-(4,4-dimethylpiperidin-1-yl)-2,6-dimethylpyridin-3-yl)-2-oxoacetate (6.8 g, 16.53 mmol, 77% yield. $^1$H NMR (500 MHz, CDCl$_3$) δ 5.25-5.11 (m, 1H), 3.17 (br. s., 4H), 2.71 (s, 3H), 2.41 (s, 3H), 1.42-1.37 (m, 10H), 1.00 (s, 6H).). LCMS (M+H)=413.3.

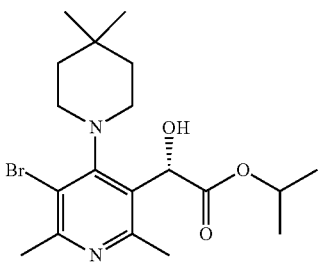 [SMILES: Cc1nc(C)c([C@H](O)C(=O)OC(C)C)c(N2CCC(C)(C)CC2)c1Br]

(S)-Isopropyl 2-(5-bromo-4-(4,4-dimethylpiperidin-1-yl)-2,6-dimethylpyridin-3-yl)-2-hydroxyacetate To a yellow solution of isopropyl 2-(5-bromo-4-(4,4-dimethylpiperidin-1-yl)-2,6-dimethylpyridin-3-yl)-2-oxoacetate (7.7 g, 18.72 mmol) and (R)-1-methyl-3,3-diphenylhexahydropyrrolo[1,2-c][1,3,2]oxazaborole (7.5 mL, 7.50 mmol) in anhydrous toluene (100 mL) was added drop wise 50% catecholborane/toluene (6 mL, 28.0 mmol) over 5 min at −50° C. Then, the reaction mixture was slowly warmed to −30° C. over 1 h and left in refrigerator (−20° C.) for 3 days. Then, the reaction mixture was diluted with EtOAc (100 mL) and 20 mL of 1M Na$_2$CO$_3$, and vigorously stirred for 30 min. Aqueous layer separated and organic layer washed with sat'd Na$_2$CO$_3$ (2×25 mL) by vigorously stirring for 15 each time, then dried (MgSO$_4$), filtered and concentrated to give crude product as light purple paste which was purified by flash chromatography using 0 to 40% EtOAc/hex to afford (S)-isopropyl 2-(5-bromo-4-(4,4-dimethylpiperidin-1-yl)-2,6-dimethylpyridin-3-yl)-2-hydroxyacetate (6.7 g, 15.72 mmol, 84% yield) as colorless thick paste. $^1$H NMR (500 MHz, CDCl$_3$) δ 5.85 (d, J=5.7 Hz, 1H), 5.59 (d, J=7.4 Hz, 1H), 5.08 (dt, J=12.5, 6.3 Hz, 1H), 3.98-3.88 (m, 1H), 3.88-3.78 (m, 1H), 2.76-2.68 (m, 1H), 2.67 (s, 3H), 2.64-2.58 (m, 1H), 2.57 (s, 3H), 1.73 (td, J=12.8, 4.8 Hz, 1H), 1.65-1.59 (m, 1H), 1.47-1.35 (m, 2H), 1.27 (d, J=6.3 Hz, 3H), 1.17 (d, J=6.1 Hz, 3H), 1.09 (s, 3H), 1.04 (s, 3H). LCMS (M+H)=414.6.

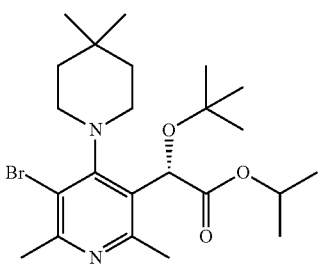 [SMILES: Cc1nc(C)c([C@H](OC(C)(C)C)C(=O)OC(C)C)c(N2CCC(C)(C)CC2)c1Br]

(S)-Isopropyl 2-(5-bromo-4-(4,4-dimethylpiperidin-1-yl)-2,6-dimethylpyridin-3-yl)-2-(tert-butoxy)acetate A stirred ice-cold yellow mixture of (S)-isopropyl 2-(5-bromo-4-(4,4-dimethylpiperidin-1-yl)-2,6-dimethylpyridin-3-yl)-2-hydroxyacetate (6.7 g, 16.21 mmol) and 70% HClO$_4$ (2.2 mL, 25.6 mmol) in dichloromethane (400 mL) was saturated with isobutylene gas by bubbling through the reaction mixture (10 min). The reaction mixture was cloudy sealed in a seal tube, stirred for 24 h at rt. The reaction mixture was recooled in a −10° C. bath, bubbled additional isobutylene (~15 min). The reaction mixture became a clear solution at this point. The tube was sealed and stirred at rt for 16 h. LCMs at this point showed incomplete reaction. So, the reaction mixture was cooled down to −30° C. and bubbled isobutene (~15 min). After 24 h, reaction mixture was neutralized with sat. Na$_2$CO$_3$ (20 mL), organic layer separated and aqueous layer was extracted with CH$_2$Cl$_2$ (25 mL). The combined organic layers were dried (MgSO$_4$), filtered, concentrated and purified on a ISCO 120 g column (EtOAc/hex: 0 to 40%) to afford (S)-isopropyl 2-(5-bromo-4-(4,4-dimethylpiperidin-1-yl)-2,6-dimethylpyridin-3-yl)-2-(tert-butoxy)acetate (5.43 g, 9.83 mmol, 60.7% yield) as a viscous oil. $^1$H NMR (500 MHz, CDCl$_3$) δ 6.26 (br. s., 1H), 5.09-4.97 (m, 1H), 4.06 (br. s., 1H), 3.51 (br. s., 1H), 2.90 (br. s., 1H), 2.65 (s, 3H), 2.56 (s, 3H), 1.72-1.54 (m, 3H), 1.47 (br. s., 1H), 1.37 (br. s., 1H), 1.23-1.20 (m, 12H), 1.15 (d, J=6.1 Hz, 3H), 1.09 (br. s., 3H), 1.04 (br. s., 3H). LCMS (M+H)=471.3.

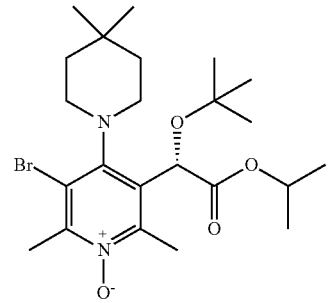

(S)-3-Bromo-5-(1-(tert-butoxy)-2-isopropoxy-2-oxoethyl)-4-(4,4-dimethylpiperidin-1-yl)-2,6-dimethylpyridine 1-oxide To a stirred solution of (S)-isopropyl 2-(5-bromo-4-(4,4-dimethylpiperidin-1-yl)-2,6-dimethylpyridin-3-yl)-2-(tert-butoxy)acetate (1.81 g, 3.86 mmol) in DCM (25 mL) was added mCPBA (1.296 g, 5.78 mmol) at rt. After 2 h, the reaction mixture was washed with sat. Na2CO3 (3×10 mL), dried (MgSO$_4$), filtered and concentrated to give (S)-3-bromo-5-(1-(tert-butoxy)-2-isopropoxy-2-oxoethyl)-4-(4,4-dimethylpiperidin-1-yl)-2,6-dimethylpyridine 1-oxide (1.854 g, 3.82 mmol, 99% yield) as pale yellow foam which was used in the next step without purification. LCMS (M+H)=487.1.

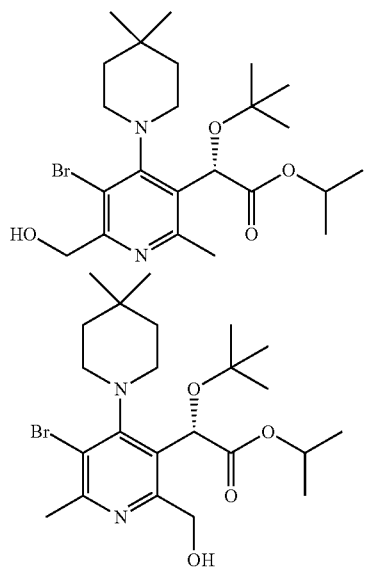

To a stirred solution of (S)-3-bromo-5-(1-(tert-butoxy)-2-isopropoxy-2-oxoethyl)-4-(4,4-dimethylpiperidin-1-yl)-2,6-dimethylpyridine 1-oxide (1.874 g, 3.86 mmol) in anhydrous DCM (20 mL) was added trifluoroacetic anhydride (1.090 ml, 7.72 mmol) at rt and then refluxed for 2.5 h. Then, MeOH (1 mL) and Et₃N (0.7 mL, 5 mmol) were added and stirred for 30 min. Then, cooled, washed with sat Na₂CO₃ (10 mL), dried (MgSO₄), filtered, concentrated and purified by flash chromatography using 5 and 10% EtOAc/hex to afford two compounds.

(S)-Isopropyl 2-(5-bromo-4-(4,4-dimethylpiperidin-1-yl)-6-(hydroxymethyl)-2-methylpyridin-3-yl)-2-(tert-butoxy)acetate Viscous colorless oil which turns into white solid over the time, 1.3311 g (71%). ¹H NMR (500 MHz, CDCl₃) δ 6.25 (br. s., 1H), 5.06 (spt, J=6.3 Hz, 1H), 4.75-4.79 (m, 1H), 4.74-4.62 (m, 2H), 4.02-4.12 (br. s., 1H), 3.54-3.46 (m, 1H), 2.93 (d, J=11.5 Hz, 1H), 2.70-2.63 (m, 1H), 2.61 (s, 3H), 1.65-1.56 (m, 2H), 1.50-1.43 (m, 1H), 1.35-1.40 (m, 1H), 1.23 (d, J=6.2 Hz, 3H), (1.22 (s, 9H), 1.16 (d, J=6.3 Hz, 3H), 1.09 (s, 3H), 1.05 (s, 3H). LCMS (M+H)=485.35 and 487.2.

(S)-Isopropyl 2-(5-bromo-4-(4,4-dimethylpiperidin-1-yl)-2-(hydroxymethyl)-6-methylpyridin-3-yl)-2-(tert-butoxy)acetate Pale yellow paste, 0.2762 g (15%). ¹H NMR (500 MHz, CDCl₃) δ 6.21 (br. s., 1H), 5.03 (spt, J=6.3 Hz, 1H), 4.95 (d, J=15.1 Hz, 1H), 4.64 (dd, J=15.3, 5.0 Hz, 1H), 4.50 (br. s., 1H), 4.05-3.97 (m, 1H), 3.57 (td, J=12.1, 2.5 Hz, 1H), 2.84 (d, J=11.8 Hz, 1H), 2.69 (s, 3H), 2.62 (d, J=11.8 Hz, 1H), 1.66-1.55 (m, 2H), 1.47 (dd, J=13.2, 2.0 Hz, 1H), 1.40-1.34 (m, 1H), 1.23 (d, J=6.3 Hz, 3H), 1.22 (s, 9H), 1.16 (d, J=6.1 Hz, 3H), 1.09 (s, 3H), 1.05 (s, 3H). LCMS (M+H)=485.2 and 487.05.

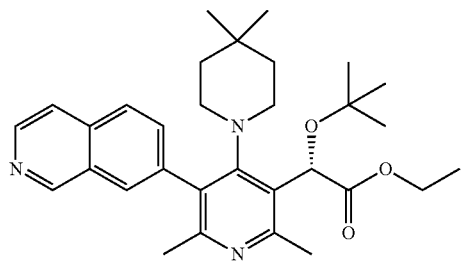 [SMILES: CCOC(=O)[C@@H](OC(C)(C)C)c1c(C)nc(C)c(-c2ccc3ccncc3c2)c1N1CCC(C)(C)CC1]

(S)-Ethyl 2-(tert-butoxy)-2-(4-(4,4-dimethylpiperidin-1-yl)-5-(isoquinolin-7-yl)-2,6-dimethylpyridin-3-yl)acetate A mixture of (S)-ethyl 2-(5-bromo-4-(4,4-dimethylpiperidin-1-yl)-2,6-dimethylpyridin-3-yl)-2-(tert-butoxy)acetate (0.052 g, 0.114 mmol), isoquinolin-7-ylboronic acid (0.030 g, 0.171 mmol) and 2M Na₂CO₃ (0.143 ml, 0.285 mmol) in DMF (2 mL) was degassed for 10 min. Then, Pd(Ph₃P)₄ (0.013 g, 0.011 mmol) added, degassed for 5 min and placed in a oil bath pre-heated to 100° C. After 2 h at 110° C., cooled and purified by prep-HPLC to afford (S)-ethyl 2-(tert-butoxy)-2-(4-(4,4-dimethylpiperidin-1-yl)-5-(isoquinolin-7-yl)-2,6-dimethylpyridin-3-yl)acetate (0.015 g, 0.030 mmol, 26.1% yield) as white solid. ¹HNMR shows as a mixture of two compounds, possibly atropisomers. LCMS (M+H)=504.5.

Example 1

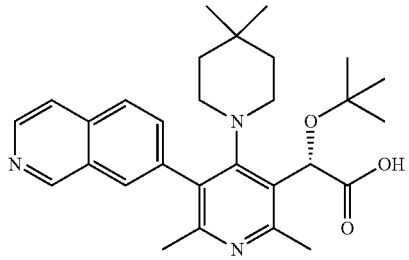 [SMILES: Cc1nc(C)c([C@H](OC(C)(C)C)C(=O)O)c(N2CCC(C)(C)CC2)c1-c1ccc2ccncc2c1]

(S)-2-(tert-Butoxy)-2-(4-(4,4-dimethylpiperidin-1-yl)-5-(isoquinolin-7-yl)-2,6-dimethylpyridin-3-yl) acetic acid A mixture of (S)-ethyl 2-(tert-butoxy)-2-(4-(4,4-dimethylpiperidin-1-yl)-5-(isoquinolin-7-yl)-2,6-dimethylpyridin-3-yl)acetate (0.015 g, 0.030 mmol) and LiOH (7.13 mg, 0.298 mmol) in 9:1 EtOH/H2O was refluxed for 2.5 h. Then, cooled and purified by prep-HPLC to afford (S)-2-(tert-butoxy)-2-(4-(4,4-dimethylpiperidin-1-yl)-5-(isoquinolin-7-yl)-2,6-dimethylpyridin-3-yl)acetic acid (0.0105 g, 0.022 mmol, 74.1% yield) as white solid. ¹H NMR (500 MHz, CDCl₃) δ 9.32 (d, J=8.0 Hz, 1H), 8.63 (t, J=6.3 Hz, 1H), 7.75-8.00 (m, 3H), 7.53-7.68 (m, 1H), 6.04 (br. s., 1H), 3.32-3.88 (m, 2H), 2.74-3.10 (m, 2H), 2.67 (s, 1.5H), 2.67 (s, 1.5H), 2.25 (s, 1.5H), 2.21 (s, 1.5H), 1.27 (s, 9H), 0.82 (br. s., 3H), 0.36 (br. s., 3H). 4H of piperidine are missing. LCMS (M+H)=476.5. HNMR indicates this compound is ~1:1 mixture of isomers.

General Procedure for the Synthesis of Compounds of the Invention from (S)-ethyl or (S)-iso propyl 2-(5-bromo-4-(4,4-dimethylpiperidin-1-yl)-2,6-dimethylpyridin-3-yl)-2-(tert-butoxy)acetate

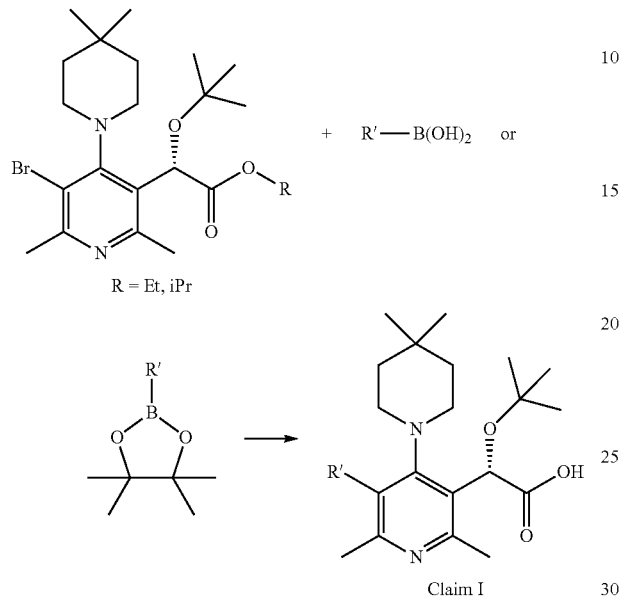

Claim I

To a mixture of (S)-ethyl or (S)-isopropyl 2-(5-bromo-4-(4,4-dimethylpiperidin-1-yl)-2,6-dimethylpyridin-3-yl)-2-(tert-butoxy)acetate (1 eq.), aryl boronic acid or ester (1-5 eq.) and $Cs_2CO_3$ (2-10 eq.) in 1,4-dioxane and water (volume ratio 20:1 to 1:1) was added $Pd(PPh_3)_4$ (0.01-1 eq.). The mixture was flushed with nitrogen and then heated at 50-150° C. for 1 to 48 hours. The mixture was diluted with water and then extracted with EtOAc. The organic layers were combined, washed with brine and concentrated to give a crude product, which was diluted with MeOH and $H_2O$ or THF (20:1 to 1:1), before NaOH or KOH (0.1-5 eq.) was added. The mixture was heated at 50-150° C. for 1 to 48 hours. All the solvents were removed under vacuum and the residue which was purified by preparative HPLC to give the desired product.

| Example | Name Structure | LCMS (M + H) |
|---|---|---|
| 2 | (S)-2-(tert-butoxy)-2-(4-(4,4-dimethylpiperidin-1-yl)-2,6-dimethyl-5-(quinolin-3-yl)pyridin-3-yl)acetic acid | 476.3 |
| 3 | (S)-2-(tert-butoxy)-2-(5-(2,3-dihydrobenzo[b][1,4]dioxin-6-yl)-4-(4,4-dimethylpiperidin-1-yl)-2,6-dimethylpyridin-3-yl)acetic acid | 483.3 |
| 4 | (S)-2-(tert-butoxy)-2-(4-(4,4-dimethylpiperidin-1-yl)-5-(1H-indol-6-yl)-2,6-dimethylpyridin-3-yl)acetic acid | 464.3 |
| 5 | (S)-2-(tert-butoxy)-2-(5-(2,3-dihydro-1H-inden-5-yl)-4-(4,4-dimethylpiperidin-1-yl)-2,6-dimethylpyridin-3-yl)acetic acid | 465.3 |
| 6 | (S)-5-(5-(tert-butoxy(carboxy)methyl)-4-(4,4-dimethylpiperidin-1-yl)-2,6-dimethylpyridin-3-yl)benzo[b]thiophene-2-carboxylic acid | 525.2 |

| Example | Name Structure | LCMS (M + H) |
|---|---|---|
| 7 | (2S)-2-(5-(benzofuran-3-yl)-4-(4,4-dimethylpiperidin-1-yl)-2,6-dimethylpyridin-3-yl)-2-(tert-butoxy)acetic acid | 465.3 |

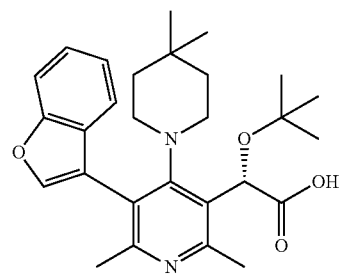 [SMILES: Cc1nc(C)c([C@H](OC(C)(C)C)C(=O)O)c(N2CCC(C)(C)CC2)c1-c1coc2ccccc12]

| | | |
|---|---|---|
| 8 | (S)-2-(tert-butoxy)-2-(4-(4,4-dimethylpiperidin-1-yl)-2,6-dimethyl-5-(2-oxo-2,3-dihydro-1H-benzo[d]imidazol-5-yl)pyridin-3-yl)acetic acid | 481.3 |

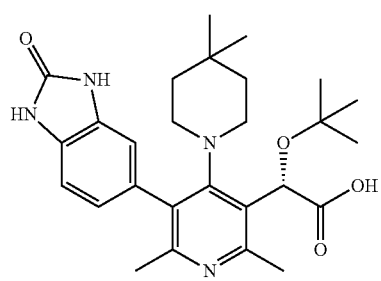 [SMILES: Cc1nc(C)c([C@H](OC(C)(C)C)C(=O)O)c(N2CCC(C)(C)CC2)c1-c1ccc2[nH]c(=O)[nH]c2c1]

| | | |
|---|---|---|
| 9 | (S)-2-(tert-butoxy)-2-(4-(4,4-dimethylpiperidin-1-yl)-2,6-dimethyl-5-(4-methyl-3,4-dihydro-2H-benzo[b][1,4]oxazin-7-yl)pyridin-3-yl)acetic acid | 496.3 |

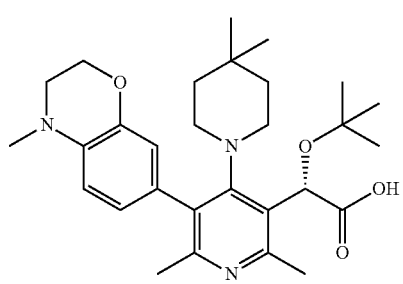 [SMILES: Cc1nc(C)c([C@H](OC(C)(C)C)C(=O)O)c(N2CCC(C)(C)CC2)c1-c1ccc2c(c1)OCCN2C]

| | | |
|---|---|---|
| 10 | (S)-2-(tert-butoxy)-2-(4-(4,4-dimethylpiperidin-1-yl)-2,6-dimethyl-5-(1-oxo-1,2,3,4-tetrahydroisoquinolin-6-yl)pyridin-3-yl)acetic acid | 494.3 |

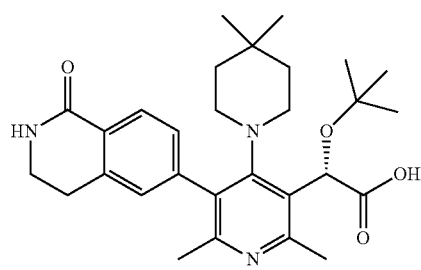 [SMILES: Cc1nc(C)c([C@H](OC(C)(C)C)C(=O)O)c(N2CCC(C)(C)CC2)c1-c1ccc2c(c1)CCNC2=O]

| Example | Name Structure | LCMS (M + H) |
|---|---|---|
| 11 | (S)-2-(tert-butoxy)-2-(4-(4,4-dimethylpiperidin-1-yl)-2,6-dimethyl-5-(1-oxoisoindolin-5-yl)pyridin-3-yl)acetic acid | 480.2 |

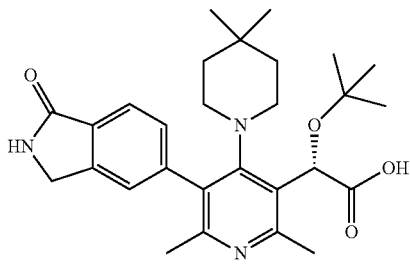 [SMILES: Cc1nc(C)c([C@H](OC(C)(C)C)C(=O)O)c(N2CCC(C)(C)CC2)c1-c1ccc2c(c1)CNC2=O]

| | | |
|---|---|---|
| 12 | (S)-2-(tert-butoxy)-2-(4-(4,4-dimethylpiperidin-1-yl)-5-(4-hydroxy-2-oxo-1,2-dihydroquinolin-6-yl)-2,6-dimethylpyridin-3-yl)acetic acid | 508.2 |

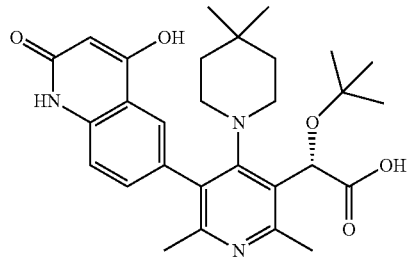 [SMILES: Cc1nc(C)c([C@H](OC(C)(C)C)C(=O)O)c(N2CCC(C)(C)CC2)c1-c1ccc2[nH]c(=O)cc(O)c2c1]

Example 13

Preparation of (S)-2-(tert-butoxy)-2-(4-(4,4-dimethylpiperidin-1-yl)-5-(2-(4-fluorobenzyl)-1-oxoisoindolin-5-yl)-2,6-dimethylpyridin-3-yl)acetic acid

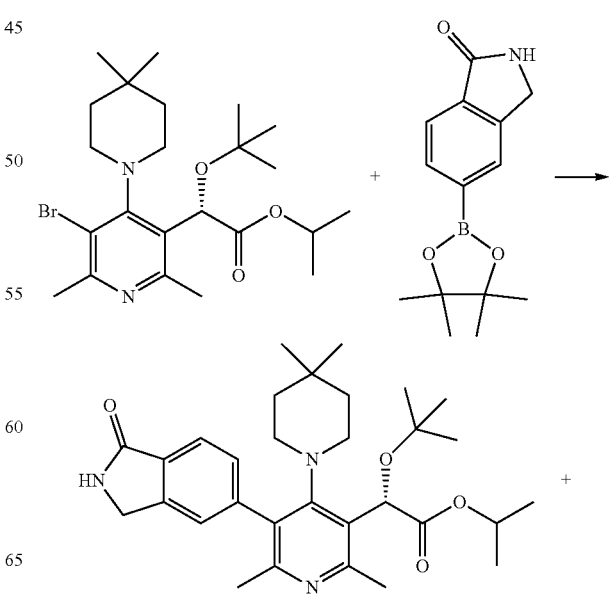

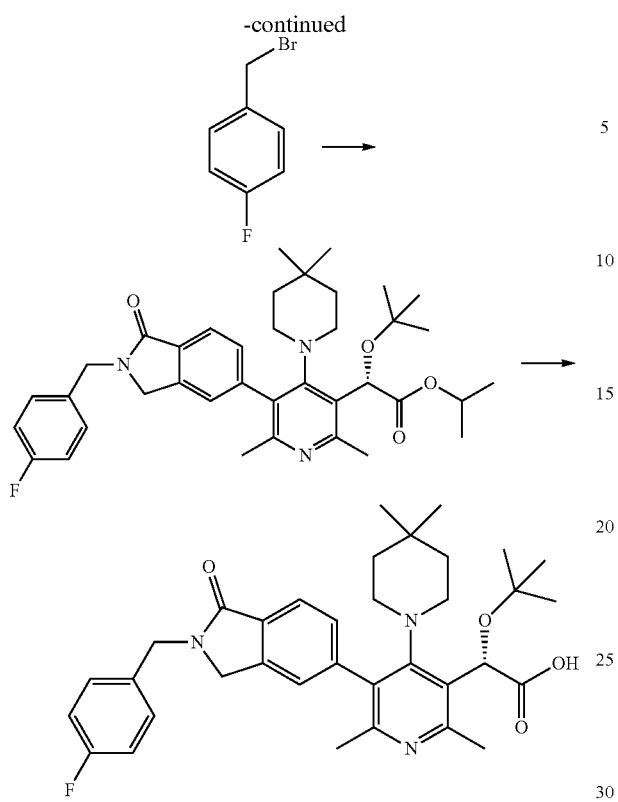

Step 1: To a mixture of (S)-isopropyl 2-(5-bromo-4-(4,4-dimethylpiperidin-1-yl)-2,6-dimethylpyridin-3-yl)-2-(tert-butoxy)acetate (150 mg), 5-(4,4,5,5-tetramethyl-1,3,2-dioxaborolan-2-yl)isoindolin-1-one (124 mg) and Cs$_2$CO$_3$ (208 mg) in 1,4-dioxane (2 mL)/water (0.4 mL) was added Pd(PPh$_3$)$_4$ (36.9 mg). The mixture was flushed with nitrogen and then heated at 85° C. for 6 hours. The mixture was diluted with water and then extracted with EtOAc (2×20 mL). The organic layers were combined, washed with brine (20 mL) and concentrated under vaccum to give a residue, which was purified by the preparative HPLC system to give (S)-isopropyl 2-(tert-butoxy)-2-(4-(4,4-dimethylpiperidin-1-yl)-2,6-dimethyl-5-(1-oxoisoindolin-5-yl)pyridin-3-yl)acetate. LCMS: (M+H)=522.3.

Step 2: To a solution of (S)-isopropyl 2-(tert-butoxy)-2-(4-(4,4-dimethylpiperidin-1-yl)-2,6-dimethyl-5-(1-oxoisoindolin-5-yl)pyridin-3-yl)acetate (60 mg) in THF (2 mL) was added NaH (9.20 mg) at 0° C. The mixture was stirred for 30 minutes at 0° C., before 1-(bromomethyl)-4-fluorobenzene (43.5 mg) was added. The mixture was stirred at 0° C. for 1 hour and then at room temperature for 6 hours. The reaction was quenched with MeOH, diluted with EtOAc (10 mL) and washed with brine (10 mL). The organic layer was dried over MgSO$_4$ and concentrated under vaccum. The residue was purified by the preparative HPLC system to afford isopropyl (S)-2-(tert-butoxy)-2-(4-(4,4-dimethylpiperidin-1-yl)-5-(2-(4-fluorobenzyl)-1-oxoisoindolin-5-yl)-2,6-dimethylpyridin-3-yl)acetate. LCMS (M+H)=630.4.

Step 3: To a solution of a mixture (S)-isopropyl 2-(tert-butoxy)-2-(4-(4,4-dimethylpiperidin-1-yl)-5-(2-(4-fluorobenzyl)-1-oxoisoindolin-5-yl)-2,6-dimethylpyridin-3-yl) acetate (37 mg) in MeOH (1 mL)/THF (1 mL) was added sodium hydroxide (0.587 mL, 1N). The mixture was stirred at 80° C. for 12 hours, before KOH (50 mg) and 1 mL of EtOH were added. The resulting mixture was heated at 80° C. for another 4 hours. The mixture was acidified by 1N HCl to pH~4. The solvent was removed under vacuum to give a residue which was purified by the preparative HPLC system to afford (S)-2-(tert-butoxy)-2-(4-(4,4-dimethylpiperidin-1-yl)-5-(2-(4-fluorobenzyl)-1-oxoisoindolin-5-yl)-2,6-dimethylpyridin-3-yl)acetic acid. LCMS (M+H)=588.3.

Example 14

Preparation of (S)-2-(tert-butoxy)-2-(4-(4,4-dimethylpiperidin-1-yl)-5-(2-(4-fluorobenzyl)-1-oxo-1,2,3,4-tetrahydroisoquinolin-6-yl)-2,6-dimethylpyridin-3-yl)acetic acid

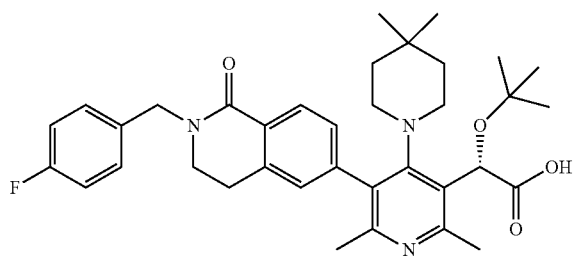 [SMILES: Cc1nc(C)c([C@H](OC(C)(C)C)C(=O)O)c(N2CCC(C)(C)CC2)c1-c1ccc2c(c1)CCN(Cc1ccc(F)cc1)C2=O]

Preparation of (S)-2-(tert-butoxy)-2-(4-(4,4-dimethylpiperidin-1-yl)-5-(2-(4-fluorobenzyl)-1-oxo-1,2,3,4-tetrahydroisoquinolin-6-yl)-2,6-dimethylpyridin-3-yl)acetic acid was prepared following the same process of syntheszing (S)-2-(tert-butoxy)-2-(4-(4,4-dimethylpiperidin-1-yl)-5-(2-(4-fluorobenzyl)-1-oxoisoindolin-5-yl)-2,6-dimethylpyridin-3-yl)acetic acid, by using 6-(4,4,5,5-tetramethyl-1,3,2-dioxaborolan-2-yl)-3,4-dihydroisoquinolin-1(2H)-one instead of 5-(4,4,5,5-tetramethyl-1,3,2-dioxaborolan-2-yl)isoindolin-1-one, in the step 1. LCMS (M+H)=602.4.

Example 15

Preparation of (S)-2-(tert-butoxy)-2-(4-(4,4-dimethylpiperidin-1-yl)-2,6-dimethyl-5-(1-oxo-2-(thiazol-2-ylmethyl)-1,2,3,4-tetrahydroisoquinolin-6-yl)pyridin-3-yl)acetic acid

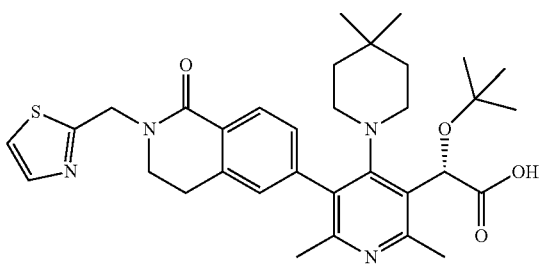 [SMILES: Cc1nc(C)c([C@H](OC(C)(C)C)C(=O)O)c(N2CCC(C)(C)CC2)c1-c1ccc2c(c1)CCN(Cc1nccs1)C2=O]

Preparation of (S)-2-(tert-butoxy)-2-(4-(4,4-dimethylpiperidin-1-yl)-2,6-dimethyl-5-(1-oxo-2-(thiazol-2-ylmethyl)-1,2,3,4-tetrahydroisoquinolin-6-yl)pyridin-3-yl)acetic acid was prepared following the same process of syntheszing (S)-2-(tert-butoxy)-2-(4-(4,4-dimethylpiperidin-1-yl)-5-(2-(4-fluorobenzyl)-1-oxo-1,2,3,4-tetrahydroisoquinolin-6-yl)-2,6-dimethylpyridin-3-yl)acetic acid, by using 2-(bromomethyl)thiazole instead of 1-(bromomethyl)-4-fluorobenzene, in the step 2. LCMS (M+H)=591.3.

Example 16

Preparation of (S)-2-(tert-butoxy)-2-(4-(4,4-dimethylpiperidin-1-yl)-2,6-dimethyl-5-(2-((4-methylthiazol-5-yl)methyl)-1-oxo-1,2,3,4-tetrahydroisoquinolin-6-yl)pyridin-3-yl)acetic acid

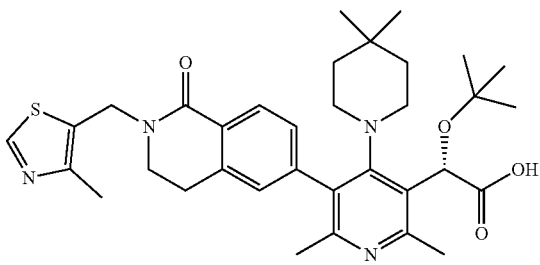 [SMILES: Cc1ncsc1CN1CCc2cc(-c3c(C)nc(C)c([C@H](OC(C)(C)C)C(=O)O)c3N3CCC(C)(C)CC3)ccc2C1=O]

Preparation of (S)-2-(tert-butoxy)-2-(4-(4,4-dimethylpiperidin-1-yl)-2,6-dimethyl-5-(2-((4-methylthiazol-5-yl)methyl)-1-oxo-1,2,3,4-tetrahydroisoquinolin-6-yl)pyridin-3-yl)acetic acid was prepared following the same process of syntheszing (S)-2-(tert-butoxy)-2-(4-(4,4-dimethylpiperidin-1-yl)-5-(2-(4-fluorobenzyl)-1-oxo-1,2,3,4-tetrahydroisoquinolin-6-yl)-2,6-dimethylpyridin-3-yl)acetic acid, by using 5-(chloromethyl)-4-methylthiazole instead of 1-(bromomethyl)-4-fluorobenzene, in the step 2. LCMS (M+H)=605.3.

Example 17

Preparation of (S)-2-(tert-butoxy)-2-(4-(4,4-dimethylpiperidin-1-yl)-2,6-dimethyl-5-(1-oxo-2-(thiazol-4-ylmethyl)-1,2,3,4-tetrahydroisoquinolin-6-yl)pyridin-3-yl)acetic acid

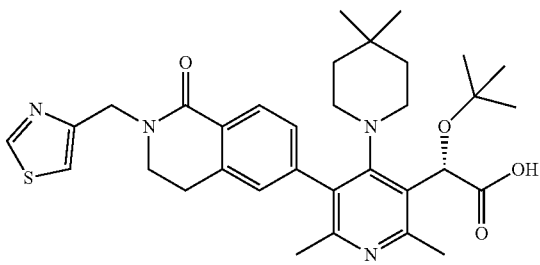 [SMILES: Cc1nc(C)c([C@H](OC(C)(C)C)C(=O)O)c(N2CCC(C)(C)CC2)c1-c1ccc2c(c1)CCN(Cc1cscn1)C2=O]

Preparation of (S)-2-(tert-butoxy)-2-(4-(4,4-dimethylpiperidin-1-yl)-2,6-dimethyl-5-(1-oxo-2-(thiazol-4-ylmethyl)-1,2,3,4-tetrahydroisoquinolin-6-yl)pyridin-3-yl)acetic acid was prepared following the same process of syntheszing (S)-2-(tert-butoxy)-2-(4-(4,4-dimethylpiperidin-1-yl)-5-(2-(4-fluorobenzyl)-1-oxo-1,2,3,4-tetrahydroisoquinolin-6-yl)-2,6-dimethylpyridin-3-yl)acetic acid, by using 4-(chloromethyl)thiazole instead of 1-(bromomethyl)-4-fluorobenzene, in the step 2. LCMS (M+H)=591.3.

Example 18 and 19

Preparation of (S)-2-(tert-butoxy)-2-(4-(4,4-dimethylpiperidin-1-yl)-5-(4-((4-fluorobenzyl)oxy)-2-oxo-1,2-dihydroquinolin-6-yl)-2,6-dimethylpyridin-3-yl) acetic acid, and, (S)-2-(5-(3,3-bis(4-fluorobenzyl)-2,4-dioxo-1,2,3,4-tetrahydroquinolin-6-yl)-4-(4,4-dimethylpiperidin-1-yl)-2,6-dimethylpyridin-3-yl)-2-(tert-butoxy)acetic acid

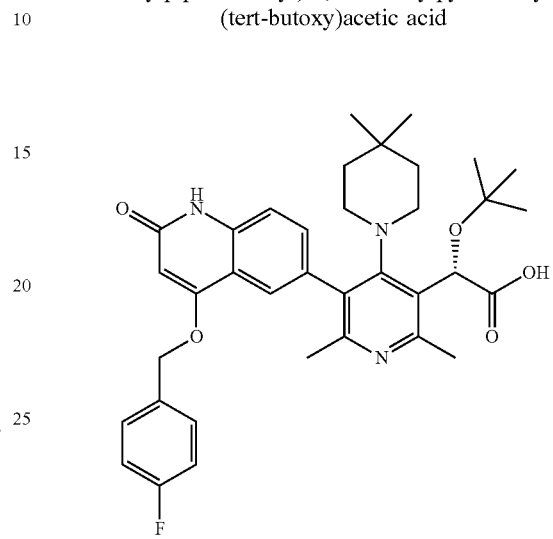

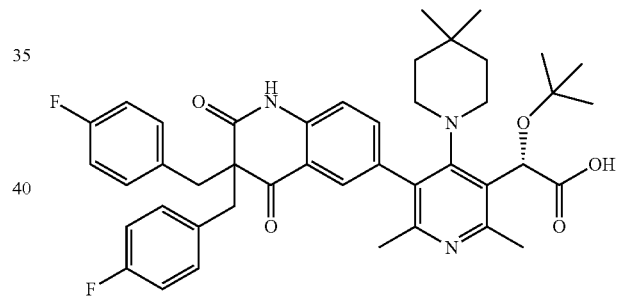

Preparation of (S)-2-(tert-butoxy)-2-(4-(4,4-dimethylpiperidin-1-yl)-5-(4-((4-fluorobenzyl)oxy)-2-oxo-1,2-dihydroquinolin-6-yl)-2,6-dimethylpyridin-3-yl)acetic acid and (S)-2-(5-(3,3-bis(4-fluorobenzyl)-2,4-dioxo-1,2,3,4-tetrahydroquinolin-6-yl)-4-(4,4-dimethylpiperidin-1-yl)-2,6-dimethylpyridin-3-yl)-2-(tert-butoxy)acetic acid were prepared following the same process of syntheszing (S)-2-(tert-butoxy)-2-(4-(4,4-dimethylpiperidin-1-yl)-5-(2-(4-fluorobenzyl)-1-oxoisoindolin-5-yl)-2,6-dimethylpyridin-3-yl)acetic acid, by using (4-hydroxy-2-oxo-1,2-dihydroquinolin-6-yl)boronic acid instead of 5-(4,4,5,5-tetramethyl-1,3,2-dioxaborolan-2-yl)isoindolin-1-one, in the step 1. (S)-2-(tert-butoxy)-2-(4-(4,4-dimethylpiperidin-1-yl)-5-(4-((4-fluorobenzyl)oxy)-2-oxo-1,2-dihydroquinolin-6-yl)-2,6-dimethylpyridin-3-yl)acetic acid, LCMS (M+H)=616.3. (S)-2-(5-(3,3-bis(4-fluorobenzyl)-2,4-dioxo-1,2,3,4-tetrahydroquinolin-6-yl)-4-(4,4-dimethylpiperidin-1-yl)-2,6-dimethylpyridin-3-yl)-2-(tert-butoxy)acetic acid, LCMS (M+H)=724.4.

Example 20

Preparation of (S)-2-(tert-butoxy)-2-(4-(4,4-dimethylpiperidin-1-yl)-5-(4-((4-fluorobenzyl)oxy)-1-methyl-2-oxo-1,2-dihydroquinolin-6-yl)-2,6-dimethylpyridin-3-yl)acetic acid

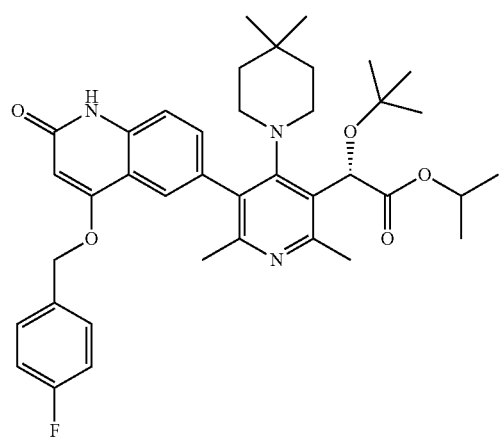

To a solution of a mixture (S)-isopropyl 2-(tert-butoxy)-2-(4-(4,4-dimethylpiperidin-1-yl)-5-(4-((4-fluorobenzyl)oxy)-2-oxo-1,2-dihydroquinolin-6-yl)-2,6-dimethylpyridin-3-yl)acetate (18 mg) in 1,4-dioxane (3 mL)/water (1 mL) was added iodomethane (3.88 mg) and KOH (12.28 mg). The mixture was stirred at 80° C. for 2 hours, before 3 mL of EtOH and KOH (250 mg) were added. The mixture was heated at 80° C. for another 6 hours. The mixture was acidified by 1N HCl to pH~4. The solvent was removed under vacuum to give a residue which was purified by the preparative HPLC system, to afford (S)-2-(tert-butoxy)-2-(4-(4,4-dimethylpiperidin-1-yl)-5-(4-((4-fluorobenzyl)oxy)-1-methyl-2-oxo-1,2-dihydroquinolin-6-yl)-2,6-dimethylpyridin-3-yl)acetic acid. LCMS (M+H)=630.3.

Example 21

Preparation of (S)-2-(tert-butoxy)-2-(4-(4,4-dimethylpiperidin-1-yl)-5-(2-(4-fluorobenzyl)isoindolin-5-yl)-2,6-dimethylpyridin-3-yl)acetic acid

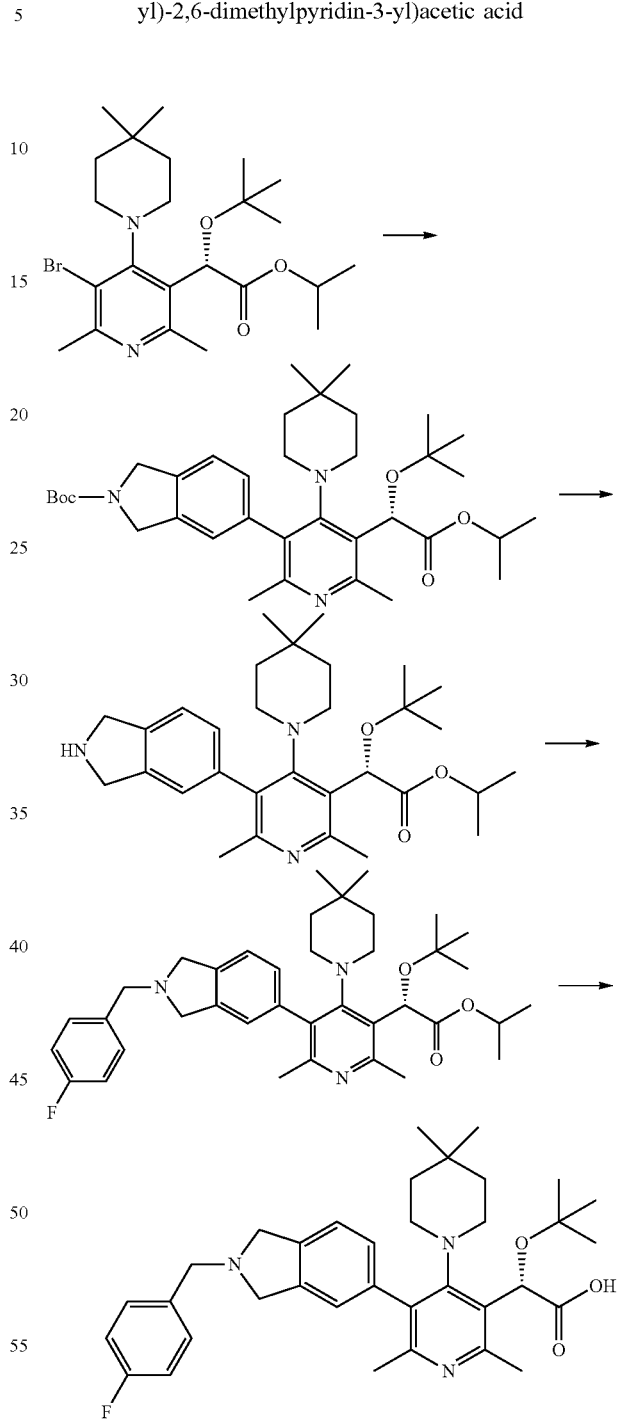

Step 1: To a mixture of (S)-isopropyl 2-(5-bromo-4-(4,4-dimethylpiperidin-1-yl)-2,6-dimethylpyridin-3-yl)-2-(tert-butoxy)acetate (280 mg), (2-(tert-butoxycarbonyl)isoindolin-5-yl)boronic acid (157 mg) and Cs$_2$CO$_3$ (389 mg) in 1,4-dioxane (25 mL)/water (5 mL) was added Pd(PPh$_3$)$_4$ (68.9 mg). The mixture was flushed with nitrogen and then heated at 85° C. for 4 hours. The mixture was diluted with water and then extracted with EtOAc (2×30 mL). The organic layers were combined, washed with brine and concentrated under vaccum. The residue was purified by the preparative HPLC to give (S)-tert-butyl 5-(5-(1-(tert-butoxy)-2-isopropoxy-2-oxoethyl)-4-(4,4-dimethylpiperidin-1-yl)-2,6-dimethylpyridin-3-yl)isoindoline-2-carboxylate. LCMS (M+H)=608.4.

Step 2: To a solution of (S)-tert-butyl 5-(5-(1-(tert-butoxy)-2-isopropoxy-2-oxoethyl)-4-(4,4-dimethylpiperidin-1-yl)-2,6-dimethylpyridin-3-yl)isoindoline-2-carboxylate (280 mg) in DCM (2 mL) was added TFA (0.5 mL). The mixture was stirred at room temperature for 3 hours. All the solvents were removed under vacuum to give (S)-isopropyl 2-(tert-butoxy)-2-(4-(4,4-dimethylpiperidin-1-yl)-5-(isoindolin-5-yl)-2,6-dimethylpyridin-3-yl)acetate, which was used in the next step without further purification. LCMS (M+H)=508.3.

Step 3: To a solutin of (S)-isopropyl 2-(tert-butoxy)-2-(4-(4,4-dimethylpiperidin-1-yl)-5-(isoindolin-5-yl)-2,6-dimethylpyridin-3-yl)acetate (50 mg) in acetonitrile (3 mL) was added K$_2$CO$_3$ (27.2 mg) and 4-fluorobenzyl bromide (27.9 mg). The mixture was stirred at room temperature for 6 hours, before being diluted with water (10 mL) and extracted with EtOAc (3×10 mL). The organic layer was dried over MgSO$_4$ and concentrated under vaccum. The residue was purified by the preparative HPLC to give (S)-isopropyl 2-(tert-butoxy)-2-(4-(4,4-dimethylpiperidin-1-yl)-5-(2-(4-fluorobenzyl)isoindolin-5-yl)-2,6-dimethylpyridin-3-yl)acetate. LCMS (M+H)=616.3.

Step 4: To a solution of (S)-isopropyl 2-(tert-butoxy)-2-(4-(4,4-dimethylpiperidin-1-yl)-5-(2-(4-fluorobenzyl)isoindolin-5-yl)-2,6-dimethylpyridin-3-yl)acetate (20 mg) in ethanol (2 mL) was aded KOH (18.22 mg) and water (0.4 mL). The mixture was heated at 85° C. for 6 hours, before being acidified by 1N HCl to pH=4. All the solvents were removed under vacuum to give a residue which was purified by the preparative HPLC system to afford (S)-2-(tert-butoxy)-2-(4-(4,4-dimethylpiperidin-1-yl)-5-(2-(4-fluorobenzyl)isoindolin-5-yl)-2,6-dimethylpyridin-3-yl)acetic acid. LCMS (M+H)=574.7.

Example 22

Preparation of (S)-2-(tert-butoxy)-2-(4-(4,4-dimethylpiperidin-1-yl)-5-(2-(4-fluorobenzoyl)isoindolin-5-yl)-2,6-dimethylpyridin-3-yl)acetic acid

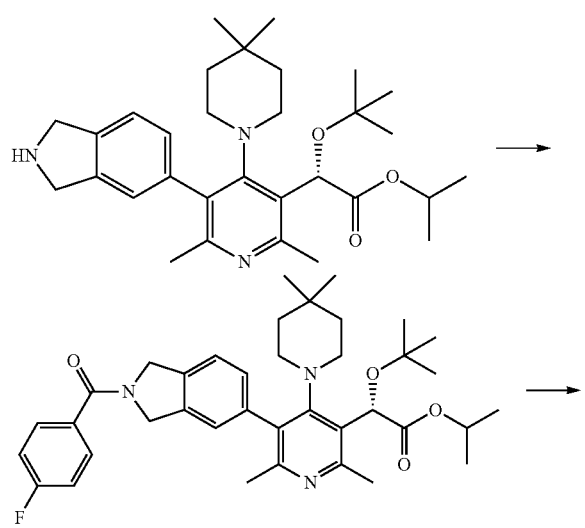

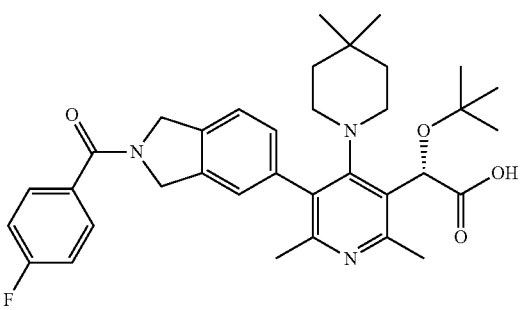

Step 1: To a solutin of (S)-isopropyl 2-(tert-butoxy)-2-(4-(4,4-dimethylpiperidin-1-yl)-5-(isoindolin-5-yl)-2,6-dimethylpyridin-3-yl)acetate (40 mg) and HATU (44.9 mg) in DMF (1.5 mL) was added 4-fluorobenzoic acid (16.56 mg) and DIPEA (0.055 mL). The mixture was stirred at room temperature for 2 hours. The desired product was isolated by using the preparative HPLC system. LCMS (M+H)=630.4.

Step 2: To a solution of (S)-isopropyl 2-(tert-butoxy)-2-(4-(4,4-dimethylpiperidin-1-yl)-5-(2-(4-fluorobenzoyl)isoindolin-5-yl)-2,6-dimethylpyridin-3-yl)acetate (19 mg) in ethanol (2 mL) was aded KOH (16.93 mg) and water (0.4 mL). The mixture was heated at 85° C. for 6 hours. The mixture was acidified by 1N HCl to pH=4. All the solvents were removed under vacuum to give a residue which purified by the preparative HPLC to afford (S)-2-(tert-butoxy)-2-(4-(4,4-dimethylpiperidin-1-yl)-5-(2-(4-fluorobenzoyl)isoindolin-5-yl)-2,6-dimethylpyridin-3-yl)acetic acid. LCMS (M+H)=588.3.

Example 23

Preparation of (S)-2-(tert-butoxy)-2-(4-(4,4-dimethylpiperidin-1-yl)-5-(2-((4-ethoxyphenyl)sulfonyl)isoindolin-5-yl)-2,6-dimethylpyridin-3-yl)acetic acid

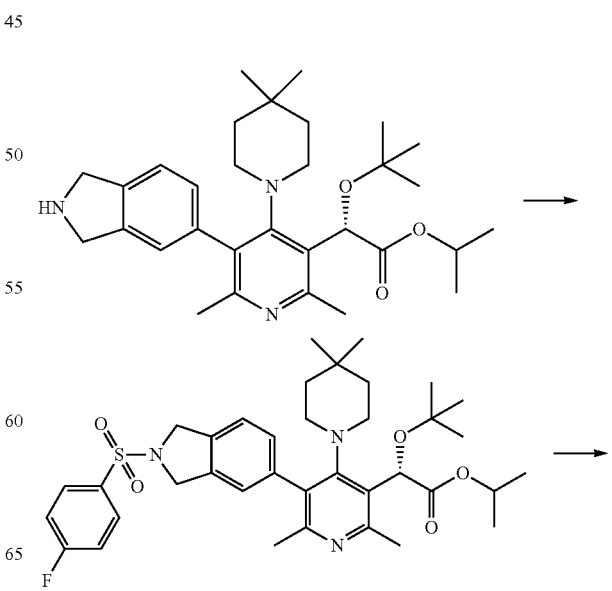

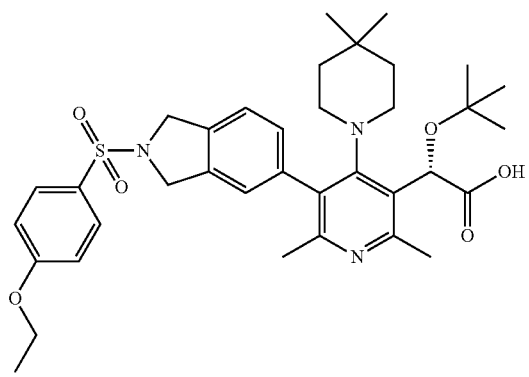

Step 1: To a solutin of (S)-isopropyl 2-(tert-butoxy)-2-(4-(4,4-dimethylpiperidin-1-yl)-5-(isoindolin-5-yl)-2,6-dimethylpyridin-3-yl)acetate (50 mg) in CH$_2$Cl$_2$ (5 mL) was added 4-fluorobenzene-1-sulfonyl chloride (28.7 mg) and iPr$_2$NEt (0.069 mL). The mixture was stirred at room temperature for 3 hours, before being diluted with 5% NaHCO$_3$ (10 mL) and extracted with CH$_2$Cl$_2$ (3×10 mL). The organic layer was washed brine, dried over MgSO$_4$ and concentrated under vaccum to give a residue which was purified by the preparative HPLC system. LCMS (M+H)=666.3.

Step 2: To a solution of (S)-isopropyl 2-(tert-butoxy)-2-(4-(4,4-dimethylpiperidin-1-yl)-5-(2-((4-fluorophenyl)sulfonyl)isoindolin-5-yl)-2,6-dimethylpyridin-3-yl)acetate (30 mg) in ethanol (2 mL) was aded KOH (20.22 mg) and water (0.4 mL). The mixture was heated at 85° C. for 6 hours, before being acidified by 1N HCl to pH=4. All the solvents were removed under vacuum to give a residue which was purified by the preparative HPLC system (S)-2-(tert-butoxy)-2-(4-(4,4-dimethylpiperidin-1-yl)-5-(2-((4-ethoxyphenyl)sulfonyl)isoindolin-5-yl)-2,6-dimethylpyridin-3-yl)acetic acid. LCMS (M+H)=650.3.

Example 24

Preparation of (S)-2-(tert-butoxy)-2-(4-(4,4-dimethylpiperidin-1-yl)-5-(2-((4-methoxyphenyl)sulfonyl)isoindolin-5-yl)-2,6-dimethylpyridin-3-yl)acetic acid

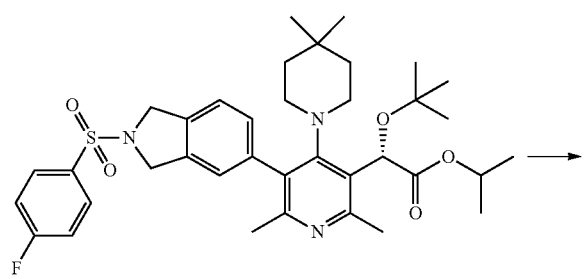

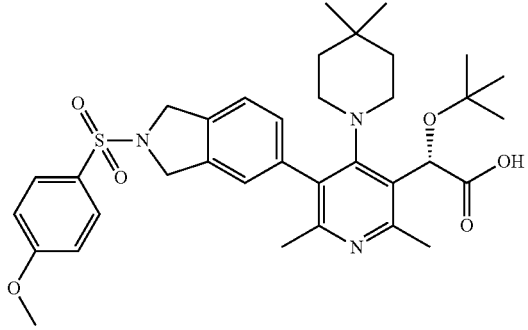

To a solution of (S)-isopropyl 2-(tert-butoxy)-2-(4-(4,4-dimethylpiperidin-1-yl)-5-(2-((4-fluorophenyl)sulfonyl)isoindolin-5-yl)-2,6-dimethylpyridin-3-yl)acetate (20 mg) in MeOH (2 mL) was aded NaOH (0.2 mL). The mixture was heated at 85° C. for 6 hours, before being acidified by 1N HCl to pH=4. All the solvents were removed under vacuum to give a residue which was purified by the preparative HPLC system (S)-2-(tert-butoxy)-2-(4-(4,4-dimethylpiperidin-1-yl)-5-(2-((4-methoxyphenyl)sulfonyl)isoindolin-5-yl)-2,6-dimethylpyridin-3-yl)acetic acid. LCMS (M+H)=636.2.

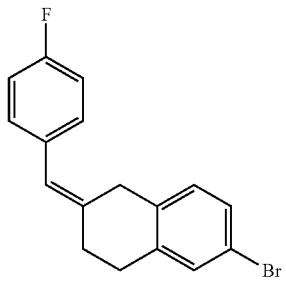 [SMILES: Fc1ccc(/C=C2/CCc3cc(Br)ccc3C2)cc1]

(Z)-6-Bromo-2-(4-fluorobenzylidene)-1,2,3,4-tetrahydronaphthalene

To a solution of (4-fluorobenzyl)triphenylphosphonium, bromide salt (1805 mg, 4.00 mmol) in DMSO (25 mL) was added 60% NaH (160 mg, 4.00 mmol) and the resulting mixture was stirred at room temperature for 30 min, and the at 50° C. for further 30 min. A solution of 6-bromo-3,4-dihydronaphthalen-2(1H)-one (900 mg, 4.00 mmol) in DMSO (5 mL) was added and the mixture was heated at 50° C. for 16 h. Mixture was then cooled to room temperature, quenched with water and extracted with ethyl acetate, washed with brine, dried (Na$_2$SO$_4$), filtered and concentrated. The residue was purified by Biotage (0-10% EtOAc/hexane) to afford (Z)-6-bromo-2-(4-fluorobenzylidene)-1,2,3,4-tetrahydronaphthalene (230 mg, 0.725 mmol, 18.13% yield) as viscous oil. $^1$H NMR (500 MHz, CDCl$_3$) δ 7.29-7.25 (m, 1H), 7.25-7.16 (m, 3H), 7.04-6.99 (m, 2H), 6.87 (d, J=8.0 Hz, 1H), 6.20 (s, 1H), 3.48 (s, 2H), 2.77 (t, J=8.2 Hz, 2H), 2.19 (t, J=8.1 Hz, 2H).

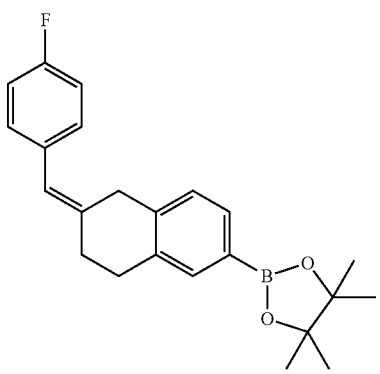 [SMILES: CC1(C)OB(c2ccc3c(c2)CC/C(=C/c2ccc(F)cc2)C3)OC1(C)C]

2-(6-(4-Fluorobenzylidene)-5,6,7,8-tetrahydronaphthalen-2-yl)-4,4,5,5-tetramethyl-1,3,2-dioxaborolane To a solution of 6-bromo-2-(4-fluorobenzylidene)-1,2,3,4-tetrahydronaphthalene (230 mg, 0.725 mmol) in anhydrous 1,4-dioxane (10 mL) was added bis(pinacolato)diborane (221 mg, 0.870 mmol) and potassium acetate (213 mg, 2.175 mmol), and the mixture was degassed for 15 min. To the degassed solution was added PdCl$_2$(dppf)-CH$_2$Cl$_2$ adduct (59.2 mg, 0.073 mmol) and degassing continued for a further 5 min, after which the reaction was heated at 90° C. for 16 h. At this point LCMS indicated completion of reaction and appearance of desired product. After cooling to room temperature, water (5 mL) was added and the mixture was extracted with ethyl ether (25 mL), washed with brine (10 mL), dried (Na$_2$SO$_4$), filtered and concentrated. Crude was then purified by Biotage using 0-20% EtOAc/hexane to afford inseparable mixture of 2-(6-(4-fluorobenzylidene)-5,6,7,8-tetrahydronaphthalen-2-yl)-4,4,5,5-tetramethyl-1,3,2-dioxaborolane isomers (130 mg, 0.357 mmol, 49.2% yield) as thick paste. $^1$H NMR (500 MHz, CDCl$_3$) δ 7.61 (d, J=7.4 Hz, 1H), 7.55 (s, 1H), 7.21 (dd, J=8.3, 5.6 Hz, 2H), 7.07-6.92 (m, 3H), 6.26 (s, 1H), 3.50 (s, 2H), 2.80 (t, J=8.1 Hz, 2H), 2.21 (t, J=8.1 Hz, 2H), 1.36 (s, 12H). LCMS (M+H)=365.4.

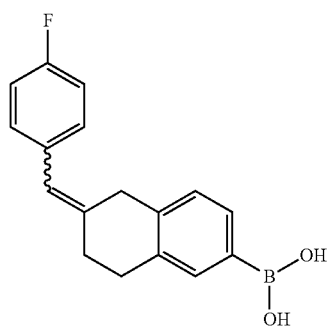 [SMILES: OB(O)c1ccc2c(c1)CCC(=Cc1ccc(F)cc1)C2]

(6-(4-Fluorobenzylidene)-5,6,7,8-tetrahydronaphthalen-2-yl)boronic acid

To a solution of 2-(6-(4-fluorobenzylidene)-5,6,7,8-tetrahydronaphthalen-2-yl)-4,4,5,5-tetramethyl-1,3,2-dioxaborolane (130 mg, 0.357 mmol) in acetone (3 mL)/water (1.500 mL) was added NaIO$_4$ (305 mg, 1.428 mmol) and NH$_4$OAc (110 mg, 1.428 mmol) and the resulting mixture was stirred at room temperature for 16 h. Then, 1N HCl (1 mL) was added and the mixture was stirred for 1 h. The mixture was then diluted with EtOAc (50 mL) and washed with brine (10 mL), dried (Na$_2$SO$_4$), filtered and concentrated to afford (6-(4-fluorobenzylidene)-5,6,7,8-tetrahydronaphthalen-2-yl)boronic acid (80 mg, 0.284 mmol, 79% yield) as off-white solid. LCMS (M+H)=283.4. Used as is in the next step.

Example 25

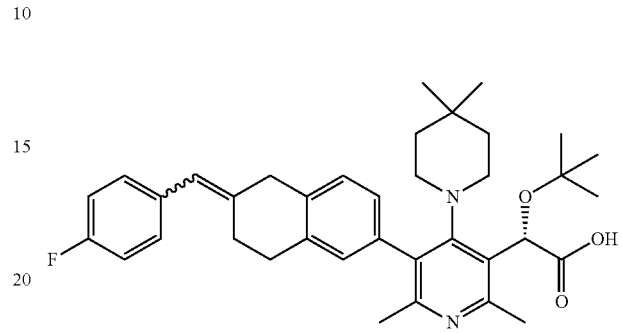

(S,E)-2-(tert-Butoxy)-2-(4-(4,4-dimethylpiperidin-1-yl)-5-(6-(4-fluorobenzylidene)-5,6,7,8-tetrahydronaphthalen-2-yl)-2,6-dimethylpyridin-3-yl)acetic acid A mixture of (S)-isopropyl 2-(5-bromo-4-(4,4-dimethylpiperidin-1-yl)-2,6-dimethylpyridin-3-yl)-2-(tert-butoxy)acetate (90 mg, 0.192 mmol), (Z)-(6-(4-fluorobenzylidene)-5,6,7,8-tetrahydronaphthalen-2-yl)boronic acid (81 mg, 0.288 mmol) and 2M Na$_2$CO$_3$ (0.240 mL, 0.479 mmol) in 1,4-dioxane (3 mL) was degassed for 10 min. Then, Pd(Ph$_3$P)$_4$ (11.08 mg, 9.59 μmol) was added, degassed for 5 min and placed in a pre-heated oil bath at 90° C. After 16 h, cooled, diluted with ether (50 mL), washed with water (10 mL), brine (25 mL), dried (Na$_2$SO$_4$), filtered and concentrated. The residue was then treated with 1N NaOH (0.959 mL, 0.959 mmol) in ethanol (2 mL) at 80° C. for 3 h. Mixture was then cooled and purified by prep HPLC to afford (S)-2-(tert-butoxy)-2-(4-(4,4-dimethylpiperidin-1-yl)-5-(6-(4-fluorobenzylidene)-5,6,7,8-tetrahydronaphthalen-2-yl)-2,6-dimethylpyridin-3-yl)acetic acid (60 mg, 0.097 mmol, 50.8% yield) as white solid. $^1$H NMR (500 MHz, DMSO-d$_6$) δ 7.31 (br. s., 2H), 7.19-7.01 (m, 3H), 6.95-6.80 (m, 1H), 6.33 (d, J=6.2 Hz, 1H), 5.85 (d, J=8.8 Hz, 1H), 3.52 (br. s., 2H), 3.37-3.18 (m, 3H), 2.88-2.68 (m, 3H), 2.43 (s, 3H), 2.25-2.14 (m, 2H), 2.11 (s, 3H), 1.95-1.79 (m, 1H), 1.48 (br. s., 1H), 1.33-1.23 (m, 1H), 1.18 (br. s., 1H), 1.12 (s, 9H), 1.05-0.95 (m, 1H), 0.84 (br. s., 3H), 0.64-0.54 (m, 3H). LCMS (M+H)=585.7.

Example 26

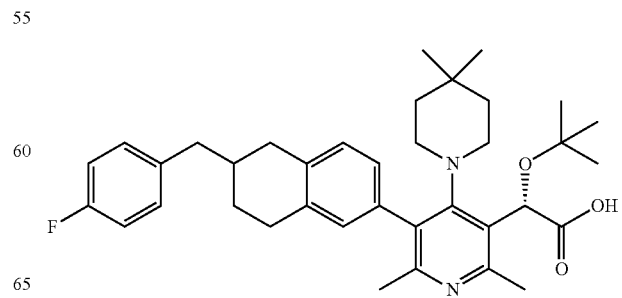

(2S)-2-(tert-Butoxy)-2-(4-(4,4-dimethylpiperidin-1-yl)-5-(6-(4-fluorobenzyl)-5,6,7,8-tetrahydronaphtha-len-2-yl)-2,6-dimethylpyridin-3-yl)acetic acid To a solution of (S)-2-(tert-butoxy)-2-(4-(4,4-dimethylpiperidin-1-yl)-5-(6-(4-fluorobenzylidene)-5,6,7,8-tetrahydronaphthalen-2-yl)-2,6-dimethylpyridin-3-yl)acetic acid (60 mg, 0.103 mmol) in MeOH (2 mL) was added 10% Pd—C (10.92 mg, 10.26 µmol) and the resulting mixture was stirred under balloon hydrogen atmosphere for 16 h. Mixture was then filtered through a pad of celite and purified by prep HPLC to afford (2S)-2-(tert-butoxy)-2-(4-(4,4-dimethylpiperidin-1-yl)-5-(6-(4-fluorobenzyl)-5,6,7,8-tetrahydronaphthalen-2-yl)-2,6-dimethylpyridin-3-yl)acetic acid (25 mg, 0.043 mmol, 41.5% yield) as inseparable mixture of diastereomers. $^1$H NMR (500 MHz, DMSO-$d_6$) δ 7.33-7.20 (m, 2H), 7.18-7.06 (m, 3H), 7.04-6.93 (m, 1H), 6.85 (br. s., 1H), 5.87 (d, J=9.5 Hz, 1H), 3.36 (br. s., 1H), 3.31 (br. s., 1H), 3.25 (br. s., 1H), 2.84 (br. s., 1H), 2.79 (br. s., 2H), 2.70-2.58 (m, 2H), 2.47 (br. s., 2H), 2.43 (s, 3H), 2.11 (s, 3H), 1.90 (d, J=18.0 Hz, 2H), 1.55-1.34 (m, 2H), 1.24 (br. s., 2H), 1.13 (s, 9H), 1.00 (br. s., 1H), 0.84 (br. s., 3H), 0.60 (d, J=9.9 Hz, 3H). LCMS (M+H)=587.2.

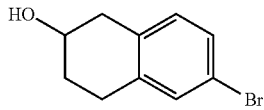

6-Bromo-1,2,3,4-tetrahydronaphthalen-2-ol

To a solution of 6-bromo-3,4-dihydronaphthalen-2(1H)-one (1 g, 4.44 mmol) in methanol (20 mL)/THF (6 mL) was added NaBH$_4$ (0.504 g, 13.33 mmol) and the resulting mixture was stirred at room temperature for 2 h. Mixture was concentrated and the residue was purified by Biotage (5-100%) EtOAc/hexane) to afford 6-bromo-1,2,3,4-tetrahydronaphthalen-2-ol (700 mg, 3.08 mmol, 69.4% yield) as off-white solid. $^1$H NMR (500 MHz, CDCl$_3$) δ 7.28-7.22 (m, 2H), 6.97 (d, J=7.9 Hz, 1H), 4.19 (dt, J=7.6, 3.8 Hz, 1H), 3.05 (dd, J=16.4, 4.7 Hz, 1H), 2.96 (dt, J=17.2, 5.9 Hz, 1H), 2.91-2.78 (m, 1H), 2.73 (dd, J=16.4, 7.6 Hz, 1H), 2.11-1.98 (m, 1H), 1.92-1.76 (m, 1H), 1.60 (d, J=3.9 Hz, 1H).

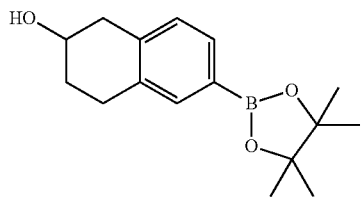 [SMILES: CC1(C)OB(c2ccc3c(c2)CCC(O)C3)OC1(C)C]

6-(4,4,5,5-Tetramethyl-1,3,2-dioxaborolan-2-yl)-1,2,3,4-tetrahydronaphthalen-2-ol To a solution of 6-bromo-1,2,3,4-tetrahydronaphthalen-2-ol (800 mg, 3.52 mmol) in anhydrous 1,4-dioxane (15 mL) was added bis(pinacolato)diborane (1073 mg, 4.23 mmol) and potassium acetate (1037 mg, 10.57 mmol), and the mixture was degassed for 15 min. To the degassed solution was added PdCl$_2$(dppf)-CH$_2$Cl$_2$ adduct (288 mg, 0.352 mmol) and degassing continued for a further 5 min, after which the reaction was heated at 90° C. for 16 h. After cooling to room temperature, water (5 mL) was added and the mixture was extracted with ethyl ether (25 mL), washed with brine (10 mL), dried (Na$_2$SO$_4$), filtered and concentrated. Crude was then purified by Biotage using 10-80% EtOAc/hexane to afford 6-(4,4,5,5-tetramethyl-1,3,2-dioxaborolan-2-yl)-1,2,3,4-tetrahydronaphthalen-2-ol as white solid. $^1$H NMR (500 MHz, CDCl$_3$) δ 7.61-7.55 (m, 2H), 7.12 (d, J=7.4 Hz, 1H), 4.22-4.15 (m, 1H), 3.13 (dd, J=16.6, 4.7 Hz, 1H), 3.05-2.93 (m, 1H), 2.93-2.74 (m, 2H), 2.11-2.05 (m, 1H), 1.89-1.78 (m, 1H), 1.36 (s, 12H).

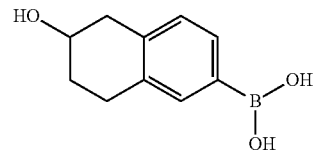

(6-Hydroxy-5,6,7,8-tetrahydronaphthalen-2-yl)boronic acid

To a solution of 6-(4,4,5,5-tetramethyl-1,3,2-dioxaborolan-2-yl)-1,2,3,4-tetrahydronaphthalen-2-ol (430 mg, 1.568 mmol) in acetone (12 mL)/water (6.00 mL) was added NaIO$_4$ (1342 mg, 6.27 mmol) and NH$_4$OAc (484 mg, 6.27 mmol) and the resulting mixture was stirred at room temperature for 16 h. 1N HCl (1 mL) was added and the mixture was stirred for 1 h. The mixture was then diluted with EtOAc (50 mL) and washed with brine (10 mL), dried (Na$_2$SO$_4$), filtered and concentrated to afford (6-hydroxy-5,6,7,8-tetrahydronaphthalen-2-yl)boronic acid as off-white solid. Used as is in the next step. $^1$H NMR (500 MHz, METHANOL-$d_4$) δ 7.39-7.28 (m, 2H), 7.10-7.03 (m, 1H), 4.06 (d, J=3.6 Hz, 1H), 3.05 (dd, J=16.5, 4.5 Hz, 1H), 3.00-2.92 (m, 1H), 2.88-2.78 (m, 1H), 2.72 (dd, J=16.4, 8.0 Hz, 1H), 2.10-2.02 (m, 1H), 1.83-1.70 (m, 1H).

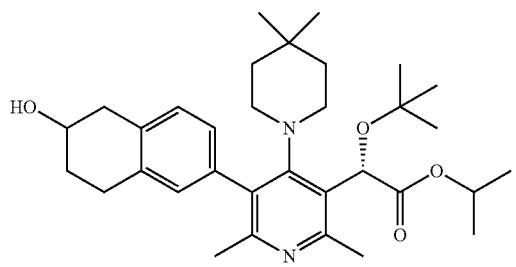 [SMILES: Cc1nc(C)c([C@H](OC(C)(C)C)C(=O)OC(C)C)c(N2CCC(C)(C)CC2)c1-c1ccc2c(c1)CCC(O)C2]

(2S)-Isopropyl 2-(tert-butoxy)-2-(4-(4,4-dimethylpiperidin-1-yl)-5-(6-hydroxy-5,6,7,8-tetrahydronaphthalen-2-yl)-2,6-dimethylpyridin-3-yl)acetate A mixture of (S)-isopropyl 2-(5-bromo-4-(4,4-dimethylpiperidin-1-yl)-2,6-dimethylpyridin-3-yl)-2-(tert-butoxy)acetate (350 mg, 0.746 mmol), (6-hydroxy-5,6,7,8-tetrahydronaphthalen-2-yl)boronic acid (215 mg, 1.118 mmol) and 2M Na$_2$CO$_3$ (0.932 mL, 1.864 mmol) in 1,4-dioxane (10 mL) was degassed for 10 min. Then, Pd(Ph$_3$P)$_4$ (43.1 mg, 0.037 mmol) was added, degassed for 5 min and placed in a pre-heated oil bath at 90° C. After 16 h, cooled, diluted with ether (50 mL), washed with water (10 mL), brine (25 mL), dried (Na$_2$SO$_4$), filtered, concentrated. The residue was then purified by Biotage (5-70% EtOAc/hexane) to afford (2S)-isopropyl 2-(tert-butoxy)-2-(4-(4,4-dimethylpiperidin-1-yl)-5-(6-hydroxy-5,6,7,8-tetrahydronaphthalen-2-yl)-2,6-dimethylpyridin-3-yl)acetate (270 mg, 0.503 mmol, 67.5% yield) as off-white solid. $^1$H NMR (500 MHz, CDCl$_3$) δ 7.19-7.11 (m, 1H), 7.05-6.98 (m, 1H), 6.92 (br. s., 1H), 6.06 (br. s., 1H), 5.10 (dq, J=11.7, 5.9 Hz, 1H), 4.25 (br. s., 1H), 3.28-3.13 (m, 2H), 3.08-2.96 (m, 1H), 2.95-2.81 (m, 3H), 2.60 (s, 3H), 2.25 (s, 2H), 2.22 (d, J=3.6 Hz, 2H), 2.17-2.02 (m, 2H), 1.96-1.79 (m, 2H), 1.63 (br. s., 1H), 1.60-1.50 (m, 1H), 1.42-1.32 (m, 1H), 1.28-1.22 (m, 6H), 1.20 (d, J=4.4 Hz, 9H), 0.91 (s, 3H), 0.64 (br. s., 3H). LCMS (M+H)=537.4.

Example 27

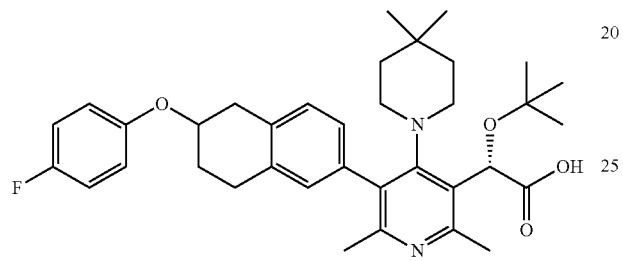

(2S)-2-(tert-Butoxy)-2-(4-(4,4-dimethylpiperidin-1-yl)-5-(6-(4-fluorophenoxy)-5,6,7,8-tetrahydronaphthalen-2-yl)-2,6-dimethylpyridin-3-yl)acetic acid To a stirred solution of (2S)-isopropyl 2-(tert-butoxy)-2-(4-(4,4-dimethylpiperidin-1-yl)-5-(6-hydroxy-5,6,7,8-tetrahydronaphthalen-2-yl)-2,6-dimethylpyridin-3-yl)acetate (50 mg, 0.093 mmol), 4-fluorophenol (20.89 mg, 0.186 mmol) and Ph$_3$P (48.9 mg, 0.186 mmol) in THF (2 mL) at 0° C. was added was added di-tert-butyl azodicarboxylate (42.9 mg, 0.186 mmol) in THF (0.5 mL) and the resulting mixture was stirred at room temperature for 16 h. Mixture was then concentrated and treated with 10N NaOH (0.093 mL, 0.932 mmol) in ethanol (1 mL) at 80° C. for 5 h. Mixture was then cooled and purified by HPLC to afford (2S)-2-(tert-butoxy)-2-(4-(4,4-dimethylpiperidin-1-yl)-5-(6-(4-fluorophenoxy)-5,6,7,8-tetrahydronaphthalen-2-yl)-2,6-dimethylpyridin-3-yl)acetic acid (3.4 mg, 5.77 μmol, 6.20% yield) as a inseparable mixture of diastereomers. $^1$H NMR (500 MHz, DMSO-d$_6$) δ 7.24-7.09 (m, 3H), 7.08-7.01 (m, 2H), 7.00-6.93 (m, 1H), 6.89-6.75 (m, 1H), 5.64 (br. s., 1H), 4.90 (br. s., 1H), 3.63 (br. s., 1H), 3.24-3.11 (m, 1H), 2.93 (d, J=17.6 Hz, 2H), 2.87-2.74 (m, 2H), 2.43 (s, 3H), 2.11 (s, 3H), 2.07 (s, 2H), 2.02-1.92 (m, 1H), 1.81 (t, J=12.3 Hz, 1H), 1.49 (d, J=9.2 Hz, 1H), 1.40-1.22 (m, 1H), 1.17 (d, J=12.8 Hz, 1H), 1.10 (s, 9H), 0.99 (d, J=12.1 Hz, 1H), 0.85 (br. s., 3H), 0.71-0.55 (m, 3H). LCMS (M+H)=589.2.

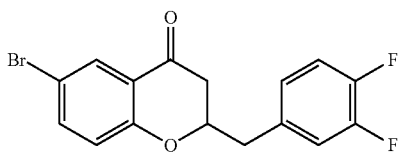 [SMILES: O=C1CC(Cc2ccc(F)c(F)c2)Oc2ccc(Br)cc21]

6-Bromo-2-(3,4-difluorobenzyl)chroman-4-one

To a mixture of 1-(5-bromo-2-hydroxyphenyl)ethanone (0.876 g, 4.08 mmol) in toluene (10 mL) was added acetic acid (0.350 mL, 6.11 mmol) and pyrrolidine (0.337 mL, 4.08 mmol). It was then stirred at rt for 10 min, then 2-(3,4-difluorophenyl)acetaldehyde (0.7 g, 4.48 mmol) was added. The mixture was heated to 70° C. for 30 hours. The reaction mixture was concentrated in vacuo. The mixture was diluted with diethyl ether and 1N aqueous NaOH. The phases were separated, and the organic was washed with more water. The combined organic phases were dried with MgSO$_4$, filtered and concentrated. The residue was purified by biotage silica gel chromatography, eluting with 10% EtOAc/hexane to give 6-bromo-2-(3,4-difluorobenzyl)chroman-4-one (300 mg, 0.849 mmol, 20.84% yield) as a yellow solid. $^1$H NMR (400 MHz, CDCl$_3$) δ 8.00 (s, 1H), 7.57 (d, J=8.6 Hz, 1H), 7.18-7.06 (m, 2H), 7.00 (br. s., 1H), 6.90 (d, J=8.6 Hz, 1H), 4.74-4.58 (m, 1H), 3.20-2.99 (m, 2H), 2.73-2.67 (m, 2H).

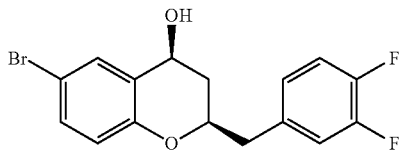 [SMILES: O[C@H]1C[C@@H](Cc2ccc(F)c(F)c2)Oc2ccc(Br)cc21]

(2R,4S)-6-Bromo-2-(3,4-difluorobenzyl)chroman-4-ol

To a mixture of 6-bromo-2-(3,4-difluorobenzyl)chroman-4-one (300 mg, 0.849 mmol) in MeOH (10 mL) was added NaBH$_4$ (32.1 mg, 0.849 mmol) and stirred at rt for 1 h. It was then quenched with water, extracted with EtOAc. The organic was dried over MgSO$_4$, filtered and concentrated to obtain an white solid. The isomers were separated by SFC with a chiralcel OJ-H preparative column (30×250 mm, 5 μm), eluting with 10% MeOH in CO$_2$, 150 bar (flow rate was 70.0 mL/min. for 20 min.) to isolate two isomers. The first peak RT=12.08 min. $^1$H NMR (400 MHz, CDCl$_3$) δ 7.59 (d, J=2.5 Hz, 1H), 7.33-7.25 (m, 1H), 7.21-7.08 (m, 2H), 7.01 (br. s., 1H), 6.71 (d, J=8.8 Hz, 1H), 4.99-4.86 (m, 1H), 4.41-4.28 (m, 1H), 3.13-2.92 (m, 2H), 2.37-2.25 (m, 1H), 1.82-1.73 (m, 2H).

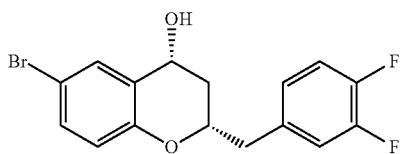 [SMILES: O[C@@H]1C[C@H](Cc2ccc(F)c(F)c2)Oc2ccc(Br)cc21]

(2S,4R)-6-Bromo-2-(3,4-difluorobenzyl)chroman-4-ol

To a mixture of 6-bromo-2-(3,4-difluorobenzyl)chroman-4-one (300 mg, 0.849 mmol) in MeOH (10 mL) was added NaBH$_4$ (32.1 mg, 0.849 mmol) and stirred at rt for 1 h. It was then quenched with water, extracted with EtOAc. The organic was dried over MgSO$_4$, filtered and concentrated to obtain an white solid. The isomers were separated by a SFC column with a chiralcel OJ-H preparative column (30×250 mm, 5 μm), eluting with 10% MeOH in CO$_2$, 150 bar (flow rate was 70.0 mL/min. for 20 min.) to isolate two isomers. The second peak RT=15.51 min. ¹H NMR (400 MHz, CDCl₃) δ 7.59 (s, 1H), 7.29-7.25 (m, 1H), 7.17-7.07 (m, 2H), 7.00 (br. s., 1H), 6.70 (d, J=8.6 Hz, 1H), 4.90 (d, J=9.0 Hz, 1H), 4.32 (dt, J=11.4, 5.8 Hz, 1H), 3.12-3.01 (m, 1H), 3.00-2.91 (m, 1H), 2.29 (dd, J=13.0, 6.1 Hz, 1H), 1.84-1.69 (m, 2H).

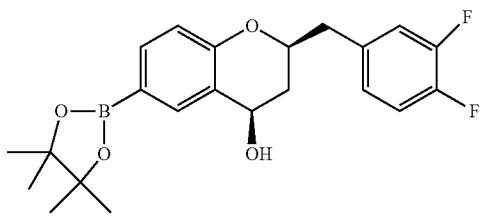 [SMILES: CC1(C)OB(c2ccc3c(c2)[C@H](O)C[C@H](Cc2ccc(F)c(F)c2)O3)OC1(C)C]

(2S,4R)-2-(3,4-Difluorobenzyl)-6-(4,4,5,5-tetramethyl-1,3,2-dioxaborolan-2-yl)chroman-4-ol A mixture of (2S,4R)-6-bromo-2-(3,4-difluorobenzyl)chroman-4-ol (100 mg, 0.282 mmol), 4,4,4',4',5,5,5',5'-octamethyl-2,2'-bi(1,3,2-dioxaborolane) (107 mg, 0.422 mmol), potassium acetate (83 mg, 0.845 mmol) in dioxane (3 mL) was degassed three times and then filled with N₂. It was then added 1,1'-bis(diphenylphosphino)ferrocene-palladium(ii)dichloride dichloromethane complex (22.99 mg, 0.028 mmol) and heated at 90° C. for 16 h. It was then quenched with water, extracted with EtOAc. The organic layer was dried over MgSO₄, filtered and concentrated. The residue was then purified by biotage, eluting with 50% EtOAc/hexane to obtain (2S,4R)-2-(3,4-difluorobenzyl)-6-(4,4,5,5-tetramethyl-1,3,2-dioxaborolan-2-yl)chroman-4-ol (100 mg, 88% yield) as a white solid. ¹H NMR (400 MHz, CDCl₃) δ 7.92 (s, 1H), 7.65 (d, J=8.1 Hz, 1H), 7.17-7.05 (m, 2H), 7.04-6.95 (m, 1H), 6.86-6.77 (m, 1H), 5.04-4.84 (m, 1H), 4.45-4.29 (m, 1H), 3.14-3.02 (m, 1H), 3.02-2.88 (m, 1H), 2.31 (ddd, J=13.1, 6.2, 2.0 Hz, 1H), 1.90-1.69 (m, 2H), 1.35 (s, 12H).

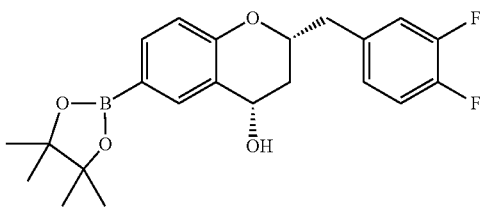 [SMILES: CC1(C)OB(c2ccc3c(c2)[C@@H](O)C[C@@H](Cc2ccc(F)c(F)c2)O3)OC1(C)C]

(2R,4S)-2-(3,4-Difluorobenzyl)-6-(4,4,5,5-tetramethyl-1,3,2-dioxaborolan-2-yl)chroman-4-ol A mixture of (2R,4S)-6-bromo-2-(3,4-difluorobenzyl)chroman-4-ol (100 mg, 0.282 mmol), 4,4,4',4',5,5,5',5'-octamethyl-2,2'-bi(1,3,2-dioxaborolane) (107 mg, 0.422 mmol) and potassium acetate (83 mg, 0.845 mmol) in dioxane (3 mL) was degassed three times and then filled with N₂. It was then added 1,1'-bis(diphenylphosphino)ferrocene-palladium(II)dichloride dichloromethane complex (22.99 mg, 0.028 mmol) and heated at 90° C. for 16 h. It was then quenched with water, extracted with EtOAc. The organic layer was dried over MgSO₄, filtered and concentrated. It was then purified by biotage, eluting with 50% EtOAc/hexane to obtain (2R,4S)-2-(3,4-difluorobenzyl)-6-(4,4,5,5-tetramethyl-1,3,2-dioxaborolan-2-yl)chroman-4-ol (90 mg, 79% yield) as a white solid. ¹H NMR (400 MHz, CDCl₃) δ 7.92 (s, 1H), 7.71-7.62 (m, 1H), 7.17-7.08 (m, 2H), 7.06-6.95 (m, 1H), 6.86-6.77 (m, 1H), 5.05-4.86 (m, 1H), 4.36 (dtd, J=10.7, 6.3, 2.0 Hz, 1H), 3.14-3.02 (m, 1H), 3.02-2.90 (m, 1H), 2.30 (ddd, J=13.1, 6.1, 2.1 Hz, 1H), 1.93-1.70 (m, 2H), 1.35 (s, 12H).

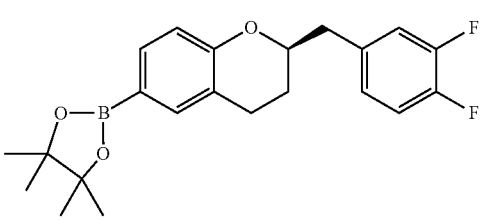 [SMILES: CC1(C)OB(c2ccc3c(c2)CC[C@H](Cc2ccc(F)c(F)c2)O3)OC1(C)C]

(R)-2-(2-(3,4-Difluorobenzyl)chroman-6-yl)-4,4,5,5-tetramethyl-1,3,2-dioxaborolane A mixture of (2S,4R)-2-(3,4-difluorobenzyl)-6-(4,4,5,5-tetramethyl-1,3,2-dioxaborolan-2-yl)chroman-4-ol (90 mg, 0.224 mmol) in DCM (2 mL) was added triethylsilane (0.286 mL, 1.790 mmol) and TFA (0.552 mL, 7.16 mmol) and stirred at rt for 3 h. It was then diluted with EtOAc, washed with NaHCO₃, water. The organic layer was dried over MgSO₄, filtered and concentrated to obtain an oil, which was puried by biotage, eluting with 10% EtOAc/hexane to obtain (R)-2-(2-(3,4-difluorobenzyl)chroman-6-yl)-4,4,5,5-tetramethyl-1,3,2-dioxaborolane (60 mg, 0.155 mmol, 69.4% yield) as a white solid. ¹H NMR (400 MHz, CDCl₃) δ 7.61-7.52 (m, 2H), 7.19-7.06 (m, 2H), 7.04-6.95 (m, 1H), 6.81 (d, J=8.1 Hz, 1H), 4.29-4.16 (m, 1H), 3.05 (dd, J=14.1, 6.7 Hz, 1H), 2.93-2.71 (m, 3H), 2.05-1.95 (m, 1H), 1.81-1.64 (m, 1H), 1.35 (s, 12H).

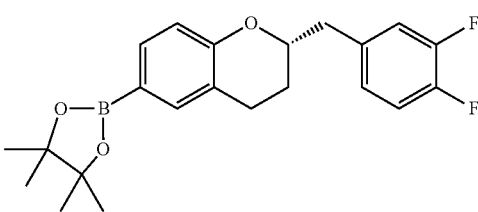 [SMILES: CC1(C)OB(c2ccc3c(c2)CC[C@@H](Cc2ccc(F)c(F)c2)O3)OC1(C)C]

(S)-2-(2-(3,4-Difluorobenzyl)chroman-6-yl)-4,4,5,5-tetramethyl-1,3,2-dioxaborolane A mixture of (2R,4S)-2-(4-fluorobenzyl)-6-(4,4,5,5-tetramethyl-1,3,2-dioxaborolan-2-yl)chroman-4-ol (140 mg, 0.364 mmol) in DCM (10 mL) was added triethylsilane (0.466 mL, 2.91 mmol), TFA (0.898 mL, 11.66 mmol) and stirred at rt for 3 h. It was then diluted with EtOAc, washed with NaHCO₃ and water. The organic layer was dried over MgSO₄, filtered and concentrated to obtain (S)-2-(2-(4-fluorobenzyl)chroman-6-yl)-4,4,5,5-tetramethyl-1,3,2-dioxaborolane (100 mg, 0.272 mmol, 74.5%, yield) as a white solid. ¹H NMR (400 MHz, CDCl₃) δ 7.64-7.50 (m, 2H), 7.25 (dd, J=8.7, 5.3 Hz, 2H), 7.05-6.96 (m, 2H), 6.81 (d, J=8.1 Hz, 1H), 4.29-4.14 (m, 1H), 3.14-3.05 (m, 1H), 2.94-2.76 (m, 3H), 2.08-1.96 (m, 1H), 1.39-1.31 (m, 12H).

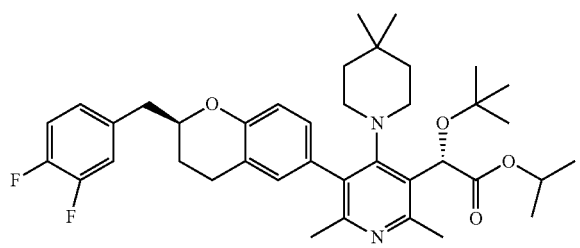 [SMILES: Cc1nc(C)c([C@H](OC(C)(C)C)C(=O)OC(C)C)c(N2CCC(C)(C)CC2)c1-c1ccc2c(c1)CC[C@@H](Cc1ccc(F)c(F)c1)O2]

(S)-Isopropyl 2-tert-butoxy-2-(5-((S)-2-(3,4-difluorobenzyl)chroman-6-yl)-4-(4,4-dimethylpiperidin-1-yl)-2,6-dimethylpyridin-3-yl)acetate A mixture of (R)-2-(2-(3,4-difluorobenzyl)chroman-6-yl)-4,4,5,5-tetramethyl-1,3,2-dioxaborolane (42.8 mg, 0.111 mmol), (S)-isopropyl 2-(5-bromo-4-(4,4-dimethylpiperidin-1-yl)-2,6-dimethylpyridin-3-yl)-2-(tert-butoxy)acetate (40 mg, 0.085 mmol), potassium phosphate (136 mg, 0.639 mmol) in dioxane (3 mL) and water (0.3 mL) was vacuum, back-filled with $N_2$ for 3 times. It was then added Pd(Ph3P)4 (19.69 mg, 0.017 mmol) and heated at 85° C. for 16 h. It was then diluted with EtOAc, washed with water. The organic layer was dried over $MgSO_4$, filtered and concentrated to obtain 50 mg of an oil, which was then purified by biotage, eluting with 25% EtOAc/hexane to isolate (S)-isopropyl 2-(tert-butoxy)-2-(5-((S)-2-(3,4-difluorobenzyl)chroman-6-yl)-4-(4,4-dimethylpiperidin-1-yl)-2,6-dimethylpyridin-3-yl)acetate (25 mg, 0.039 mmol, 45.2% yield) as a white solid. LCMS (M+H)=649.4.

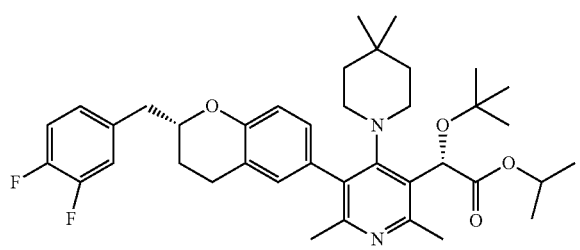 [SMILES: Cc1nc(C)c([C@H](OC(C)(C)C)C(=O)OC(C)C)c(N2CCC(C)(C)CC2)c1-c1ccc2c(c1)CC[C@H](Cc1ccc(F)c(F)c1)O2]

(S)-Isopropyl 2-tert-butoxy-2-(5-((R)-2-(3,4-difluorobenzyl) chroman-6-yl)-4-(4,4-dimethylpiperidin-1-yl)-2,6-dimethylpyridin-3-yl)acetate A mixture of (S)-2-(2-(3,4-difluorobenzyl)chroman-6-yl)-4,4,5,5-tetramethyl-1,3,2-dioxaborolane (42.8 mg, 0.111 mmol), (S)-isopropyl 2-(5-bromo-4-(4,4-dimethylpiperidin-1-yl)-2,6-dimethylpyridin-3-yl)-2-(tert-butoxy)acetate (40 mg, 0.085 mmol) and potassium phosphate (136 mg, 0.639 mmol) in dioxane (3 mL) and water (0.3 mL) was vacuum, back-filled with $N_2$ for 3 times. It was then added Pd(Ph3P)4 (19.69 mg, 0.017 mmol) and heated at 85° C. for 16 h. It was then diluted with EtOAc, washed with water. The organic was dried over $MgSO_4$, filtered and concentrated to obtain 50 mg of an oil, which was then purified by biotage, eluting with 25% EtOAc/hexane to isolate (S)-isopropyl 2-(tert-butoxy)-2-(5-((R)-2-(3,4-difluorobenzyl)chroman-6-yl)-4-(4,4-dimethylpiperidin-1-yl)-2,6-dimethylpyridin-3-yl)acetate (25 mg, 0.039 mmol, 45.2% yield) as a white solid. LCMS (M+H)=649.5.

Example 28

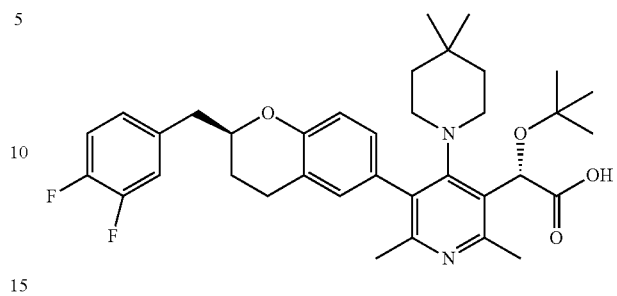

(S)-2-tert-Butoxy-2-(5-((S)-2-(3,4-difluorobenzyl) chroman-6-yl)-4-(4,4-dimethylpiperidin-1-yl)-2,6-dimethylpyridin-3-yl)acetic acid A mixture of (S)-isopropyl 2-(tert-butoxy)-2-(5-((S)-2-(3,4-difluorobenzyl)chroman-6-yl)-4-(4,4-dimethylpiperidin-1-yl)-2,6-dimethylpyridin-3-yl)acetate (25 mg, 0.039 mmol), KOH (2.162 mg, 0.039 mmol) in ethanol (2 mL), water (0.2 mL) was refluxed for 16 h. It was then filtered and purified by prep HPLC to obtain (S)-2-(tert-butoxy)-2-(5-((S)-2-(3,4-difluorobenzyl)chroman-6-yl)-4-(4,4-dimethylpiperidin-1-yl)-2,6-dimethylpyridin-3-yl)acetic acid (10.5 mg, 0.017 mmol, 44.9% yield) as a white solid. LCMS (M+H)=607.5.

Example 29

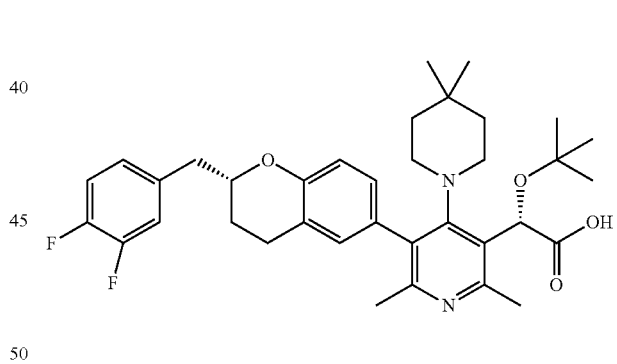

(S)-2-tert-Butoxy-2-(5-((R)-2-(3,4-difluorobenzyl) chroman-6-yl)-4-(4,4-dimethylpiperidin-1-yl)-2,6-dimethylpyridin-3-yl)acetic acid A mixture of (S)-isopropyl 2-(tert-butoxy)-2-(5-((R)-2-(3,4-difluorobenzyl)chroman-6-yl)-4-(4,4-dimethylpiperidin-1-yl)-2,6-dimethylpyridin-3-yl)acetate (25 mg, 0.039 mmol), KOH (2.162 mg, 0.039 mmol) in ethanol (2 mL) and water (0.2 mL) was refluxed for 16 h. It was then filtered and purified by pre HPLC to obtain (S)-2-(tert-butoxy)-2-(5-((R)-2-(3,4-difluorobenzyl)chroman-6-yl)-4-(4,4-dimethylpiperidin-1-yl)-2,6-dimethylpyridin-3-yl)acetic acid (19.3 mg, 0.032 mmol, 83% yield) as a white solid. LCMS (M+H)=607.2.

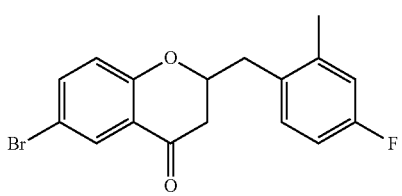 [SMILES: Cc1cc(F)ccc1CC1CC(=O)c2cc(Br)ccc2O1]

6-Bromo-2-(4-fluoro-2-methylbenzyl)chroman-4-one

To a mixture of 1-(5-bromo-2-hydroxyphenyl)ethanone (1.413 g, 6.57 mmol) in toluene (10 mL), was added acetic acid (0.564 mL, 9.86 mmol), pyrrolidine (0.543 mL, 6.57 mmol). It was then stirred at rt for 10 min, then 2-(4-fluoro-2-methylphenyl)acetaldehyde (1 g, 6.57 mmol) was added. The mixture was heated to 70° C. for 30 hours. The reaction mixture was concentrated in vacuo. The mixture was diluted with EtOAc and 1N aqueous NaOH. The phases were separated, and the organic was washed with more water. The combined organic phases were dried (MgSO$_4$), filtered and concentrated. The concentrate was purified by biotage silica gel chromatography, eluting with 10% EtOAc/hexanes to isolate 6-bromo-2-(4-fluoro-2-methylbenzyl)chroman-4-one (150 mg, 0.430 mmol, 6.54% yield). $^1$H NMR (400 MHz, CDCl$_3$) δ 8.08-7.90 (m, 1H), 7.56 (d, J=8.8 Hz, 1H), 7.22-7.11 (m, 1H), 6.96-6.82 (m, 3H), 4.74-4.52 (m, 1H), 3.21 (dd, J=14.4, 6.8 Hz, 1H), 3.03 (dd, J=14.3, 6.2 Hz, 1H), 2.80-2.60 (m, 2H), 2.37 (s, 3H).

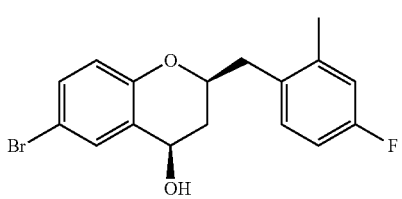 [SMILES: Cc1cc(F)ccc1C[C@H]1C[C@@H](O)c2cc(Br)ccc2O1]

(2S,4R)-6-Bromo-2-(4-fluoro-2-methylbenzyl)chroman-4-ol

A mixture of 6-bromo-2-(4-fluoro-2-methylbenzyl)chroman-4-one (150 mg, 0.430 mmol) and NaBH$_4$ (16.25 mg, 0.430 mmol) in MeOH (3 mL) and stirred at rt for 1 h. It was then quenched with NH$_4$Cl and extracted with EtOAc. The organic layer was dried over MgSO$_4$, filtered and concentrated. The isomers were separated by a SFC with a chiralcel OJ-H preparative column (30×250 mm, 5 μm), eluting with 10% MeOH in CO$_2$, 150 bar (flow rate was 70.0 mL/min. for 20 min.) to isolate isomer one as a white solid. $^1$H NMR (400 MHz, CDCl$_3$) δ 7.59 (dd, J=2.4, 0.7 Hz, 1H), 7.28-7.23 (m, 1H), 7.18 (dd, J=8.3, 5.9 Hz, 1H), 6.95-6.81 (m, 2H), 6.69 (d, J=8.8 Hz, 1H), 4.93-4.82 (m, 1H), 4.30 (dtd, J=11.3, 6.5, 1.8 Hz, 1H), 3.14 (dd, J=14.2, 6.4 Hz, 1H), 2.93 (dd, J=14.2, 6.6 Hz, 1H), 2.38 (s, 3H), 2.31 (ddd, J=13.0, 6.2, 1.8 Hz, 1H), 1.84-1.72 (m, 2H).

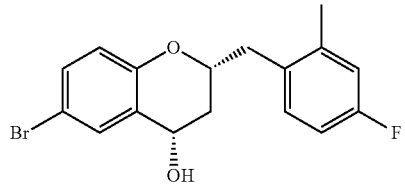 [SMILES: Cc1cc(F)ccc1C[C@@H]1C[C@H](O)c2cc(Br)ccc2O1]

(2R,4S)-6-Bromo-2-(4-fluoro-2-methylbenzyl)chroman-4-ol

A mixture of 6-bromo-2-(4-fluoro-2-methylbenzyl)chroman-4-one (150 mg, 0.430 mmol) and NaBH$_4$ (16.25 mg, 0.430 mmol) in MeOH (3 mL) and stirred at rt for 1 h. It was then quenched with NH$_4$Cl and extracted with EtOAc. The organic layer was dried over MgSO$_4$, filtered and concentrated. The isomers were separated by SFC with a chiralcel OJ-H preparative column (30×250 mm, 5 μm), eluting with 10% MeOH in CO$_2$, 150 bar (flow rate was 70.0 mL/min. for 20 min.) to isolate isomer two as a white solid. $^1$H NMR (400 MHz, CDCl$_3$) δ 7.59 (s, 1H), 7.28-7.24 (m., 1H), 7.22-7.12 (m, 1H), 6.98-6.84 (m, 2H), 6.69 (d, J=8.6 Hz, 1H), 4.95-4.77 (m, 1H), 4.30 (dt, J=12.2, 6.1 Hz, 1H), 3.14 (dd, J=13.9, 6.6 Hz, 1H), 2.93 (dd, J=14.3, 6.7 Hz, 1H), 2.38 (s, 3H), 2.31 (dd, J=13.3, 5.7 Hz, 2H), 1.85-1.72 (m, 3H).

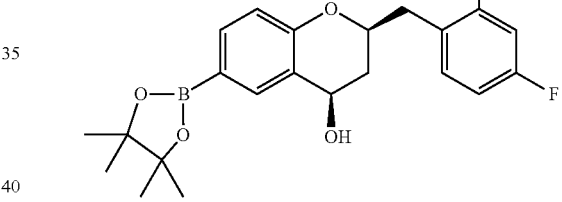

(2S,4R)-2-(4-Fluoro-2-methylbenzyl)-6-(4,4,5,5-tetramethyl-1,3,2-dioxaborolan-2-yl)chroman-4-ol A mixture of 4,4,4',4',5,5,5',5'-octamethyl-2,2'-bi(1,3,2-dioxaborolane) (76 mg, 0.299 mmol), (2S,4R)-6-bromo-2-(4-fluoro-2-methylbenzyl)chroman-4-ol (70 mg, 0.199 mmol), potassium acetate (58.7 mg, 0.598 mmol) in dioxane (3 mL) was degassed three times and then filled with N$_2$. It was then added 1,1'-bis(diphenylphosphino)ferrocene-palladium(II)dichloride dichloromethane complex (16.28 mg, 0.020 mmol) and heated at 90° C. for 16 h. It was then quenched with water, extracted with EtOAc. The organic layer was dried over MgSO$_4$, filtered and concentrated. It was then purified by biotage, eluting with 50% EtOAc/hexane to obtain (2S,4R)-2-(4-fluoro-2-methylbenzyl)-6-(4,5,5-tetramethyl-1,3,2-dioxaborolan-2-yl)chroman-4-ol (70 mg, 0.176 mmol, 88% yield) as a white solid. $^1$H NMR (400 MHz, CDCl$_3$) δ 7.93 (s, 1H), 7.72-7.61 (m, 1H), 7.25-7.14 (m, 1H), 6.93-6.84 (m, 2H), 6.80 (d, J=8.1 Hz, 1H), 4.91 (dd, J=10.0, 6.1 Hz, 1H), 4.33 (dtd, J=11.0, 6.6, 2.0 Hz, 1H), 3.16 (dd, J=13.9, 6.4 Hz, 1H), 2.99-2.87 (m, 1H), 2.38 (s, 3H), 2.32 (ddd, J=13.0, 6.1, 2.0 Hz, 1H), 1.82 (dt, J=12.9, 10.7 Hz, 2H), 1.35 (s, 12H).

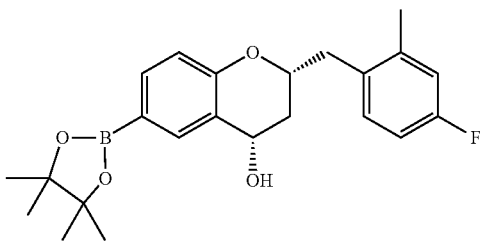 [SMILES: Cc1cc(F)ccc1C[C@@H]1C[C@H](O)c2cc(B3OC(C)(C)C(C)(C)O3)ccc2O1]

(2R,4S)-2-(4-Fluoro-2-methylbenzyl)-6-(4,4,5,5-tetramethyl-1,3,2-dioxaborolan-2-yl)chroman-4-ol A mixture of 4,4,4',4',5,5,5',5'-octamethyl-2,2'-bi(1,3,2-dioxaborolane) (76 mg, 0.299 mmol), (2R,4S)-6-bromo-2-(4-fluoro-2-methylbenzyl)chroman-4-ol (70 mg, 0.199 mmol). potassium acetate (58.7 mg, 0.598 mmol) in dioxane (3 mL) was degassed three times and then filled with N$_2$. It was then added 1,1'-bis(diphenylphosphino)ferrocene-palladium(II)dichloride dichloromethane complex (16.28 mg, 0.020 mmol) and heated at 90° C. for 16 h. It was then quenched with water, extracted with EtOAc. The organic layer was dried over MgSO$_4$, filtered and concentrated. It was then purified by biotage, eluting with 50% EtOAc/hexane to obtain (2R,4S)-2-(4-fluoro-2-methylbenzyl)-6-(4,4,5,5-tetramethyl-1,3,2-dioxaborolan-2-yl)chroman-4-ol (70 mg, 88%) as a white solid. $^1$H NMR (400 MHz, CDCl$_3$) δ 8.00-7.89 (m, 1H), 7.64 (dd, J=8.3, 1.2 Hz, 1H), 7.19 (dd, J=8.3, 5.9 Hz, 1H), 6.93-6.83 (m, 2H), 6.83-6.76 (m, 1H), 4.91 (dt, J=10.0, 6.9 Hz, 1H), 4.33 (dtd, J=11.0, 6.6, 2.0 Hz, 1H), 3.30-3.07 (m, 1H), 3.02-2.83 (m, 1H), 2.38 (s, 3H), 2.33 (ddd, J=13.1, 6.2, 2.0 Hz, 1H), 1.90-1.75 (m, 2H), 1.35 (s, 12H).

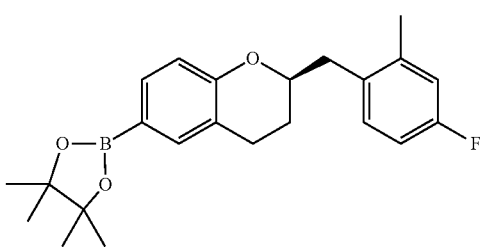 [SMILES: Cc1cc(F)ccc1C[C@H]1CCc2cc(B3OC(C)(C)C(C)(C)O3)ccc2O1]

(R)-2-(2-(4-Fluoro-2-methylbenzyl)chroman-6-yl)-4,4,5,5-tetramethyl-1,3,2-dioxaborolane A mixture of (2S,4R)-2-(4-fluoro-2-methylbenzyl)-6-(4,4,5,5-tetramethyl-1,3,2-dioxaborolan-2-yl)chroman-4-ol (70 mg, 0.176 mmol), triethylsilane (0.225 mL, 1.406 mmol), TFA (0.433 mL, 5.62 mmol) in DCM (2 mL) was stirred at rt for 3 h. It was then diluted with EtOAc, washed with NaHCO$_3$, water, dried over MgSO$_4$, filtered and concentrated to yield (R)-2-(2-(4-fluoro-2-methylbenzyl)chroman-6-yl)-4,4,5,5-tetramethyl-1,3,2-dioxaborolane (50 mg, 0.131 mmol, 74.4% yield) as a white solid. $^1$H NMR (400 MHz, CDCl$_3$) δ 7.67-7.50 (m, 2H), 7.23-7.13 (m, 1H), 6.98-6.65 (m, 3H), 4.21 (q, J=6.9 Hz, 1H), 3.12 (dd, J=14.2, 6.4 Hz, 1H), 2.91-2.66 (m, 3H), 2.38 (s, 3H), 2.02 (d, J=13.2 Hz, 1H), 1.88-1.67 (m, 1H), 1.44-1.22 (m, 12H).

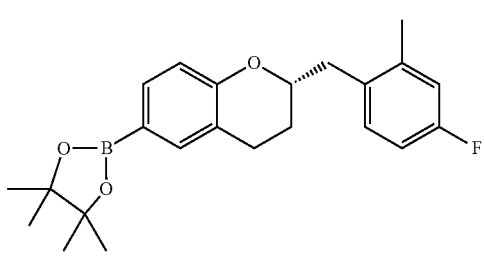 [SMILES: Cc1cc(F)ccc1C[C@@H]1CCc2cc(B3OC(C)(C)C(C)(C)O3)ccc2O1]

(S)-2-(2-(4-Fluoro-2-methylbenzyl)chroman-6-yl)-4,4,5,5-tetramethyl-1,3,2-dioxaborolane A mixture of (2R,4S)-2-(3,4-difluorobenzyl)-6-(4,4,5,5-tetramethyl-1,3,2-dioxaborolan-2-yl)chroman-4-ol (70 mg, 0.174 mmol), triethylsilane (0.222 mL, 1.392 mmol), TFA (0.429 mL, 5.57 mmol) in DCM (2 mL) was stirred at rt for 3 h. It was then diluted with EtOAc, washed with NaHCO$_3$, water, dried over MgSO$_4$, filtered and concentrated to yield (S)-2-(2-(3,4-difluorobenzyl)chroman-6-yl)-4,4,5,5-tetramethyl-1,3,2-dioxaborolane (50 mg, 0.129 mmol, 74.4% yield) as a white solid. $^1$H NMR (400 MHz, CDCl$_3$) δ 7.77-7.47 (m, 2H), 7.27-7.12 (m, 1H), 6.98-6.70 (m, 3H), 4.52-4.05 (m, 1H), 3.28-3.02 (m, 1H), 3.01-2.72 (m, 3H), 2.37 (s, 3H), 2.13-1.91 (m, 1H), 1.90-1.65 (m, 1H), 1.35 (s, 12H).

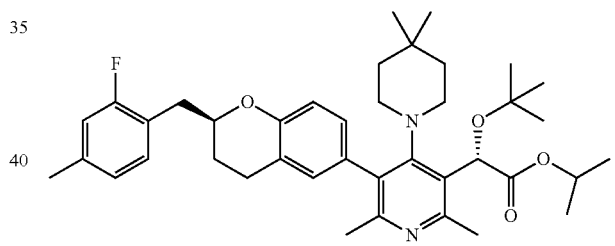

(S)-Isopropyl 2-tert-butoxy-2-(4-(4,4-dimethylpiperidin-1-yl)-5-((S)-2-(2-fluoro-4-methylbenzyl)chroman-6-yl)-2,6-dimethylpyridin-3-yl)acetate A mixture of (R)-2-(2-(4-fluoro-2-methylbenzyl)chroman-6-yl)-4,4,5,5-tetramethyl-1,3,2-dioxaborolane (63.5 mg, 0.166 mmol), (S)-isopropyl 2-(5-bromo-4-(4,4-dimethylpiperidin-1-yl)-2,6-dimethylpyridin-3-yl)-2-(tert-butoxy)acetate (60 mg, 0.128 mmol), potassium phosphate (203 mg, 0.959 mmol) in dioxane (3 mL) and water (0.3 mL) was vacuum, back-filled with N$_2$ for 3 times. It was then added Pd(Ph$_3$P)$_4$ (29.5 mg, 0.026 mmol) and heated at 85° C. for 16 h. It was then diluted with EtOAc, washed with water. The organic was dried over MgSO$_4$, filtered and concentrated to obtain 50 mg of an oil, which was then purified by biotage, eluting with 50% EtOAc/hexane to isolate (S)-isopropyl 2-(tert-butoxy)-2-(4-(4,4-dimethylpiperidin-1-yl)-5-((S)-2-(2-fluoro-4-methylbenzyl)chroman-6-yl)-2,6-dimethylpyridin-3-yl)acetate (31 mg, 0.048 mmol, 37.6% yield) as a white solid. LCMS (MS+H)=645.3.

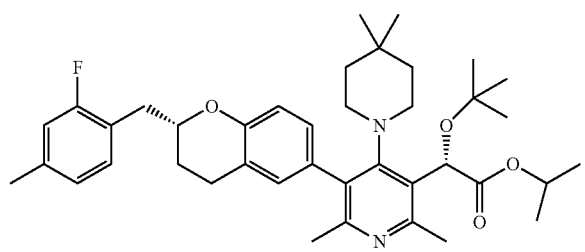 [SMILES: Cc1ccc(C[C@H]2CCc3cc(-c4c(C)nc(C)c([C@H](OC(C)(C)C)C(=O)OC(C)C)c4N4CCC(C)(C)CC4)ccc3O2)c(F)c1]

(S)-Isopropyl 2-tert-butoxy-2-(4-(4,4-dimethylpiperidin-1-yl)-5-((R)-2-(2-fluoro-4-methylbenzyl)chroman-6-yl)-2,6-dimethylpyridin-3-yl)acetate A mixture of (S)-2-(2-(4-fluoro-2-methylbenzyl)chroman-6-yl)-4,4,5,5-tetramethyl-1,3,2-dioxaborolane (85 mg, 0.222 mmol), (S)-isopropyl 2-(5-bromo-4-(4,4-dimethylpiperidin-1-yl)-2,6-dimethylpyridin-3-yl)-2-(tert-butoxy)acetate (80 mg, 0.170 mmol), potassium phosphate (271 mg, 1.278 mmol) in dioxane (3 mL) and water (0.3 mL) was vacuum, back-filled with $N_2$ for 3 times. It was then added and heated at 85° C. for 16 h. It was then diluted with EtOAc, washed with water. The organic was dried over $MgSO_4$, filtered and concentrated to obtain 50 mg of an oil, which was then purified by biotage, eluting with 50% EtOAc/hexane to isolate (S)-isopropyl 2-(tert-butoxy)-2-(4-(4,4-dimethylpiperidin-1-yl)-5-((R)-2-(2-fluoro-4-methylbenzyl)chroman-6-yl)-2,6-dimethylpyridin-3-yl)acetate (40 mg, 0.062 mmol, 36.4% yield) as a white solid. LCMS (M+H)=645.3.

Example 30

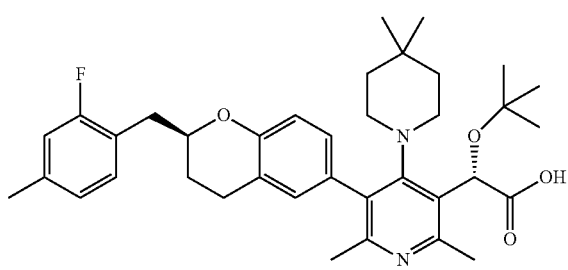 [SMILES: Cc1ccc(C[C@@H]2CCc3cc(-c4c(C)nc(C)c([C@H](OC(C)(C)C)C(=O)O)c4N4CCC(C)(C)CC4)ccc3O2)c(F)c1]

(S)-2-tert-Butoxy-2-(4-(4,4-dimethylpiperidin-1-yl)-5-((S)-2-(2-fluoro-4-methylbenzyl)chroman-6-yl)-2,6-dimethylpyridin-3-yl)acetic acid A mixture of (S)-isopropyl 2-(tert-butoxy)-2-(4-(4,4-dimethylpiperidin-1-yl)-5-((S)-2-(2-fluoro-4-methylbenzyl)chroman-6-yl)-2,6-dimethylpyridin-3-yl)acetate (30 mg, 0.047 mmol) and NaOH (0.093 mL, 0.930 mmol) in EtOH (2 mL) was refluxed for 5 h. It was then cooled to rt, filtered and concentrated. It was then purified by prep HPLC to obtain (S)-2-(tert-butoxy)-2-(4-(4,4-dimethylpiperidin-1-yl)-5-((S)-2-(2-fluoro-4-methylbenzyl)chroman-6-yl)-2,6-dimethylpyridin-3-yl)acetic acid (13 mg, 0.020 mmol, 44.0% yield) as a white solid. LCMS (M+H)=603.2.

Example 31

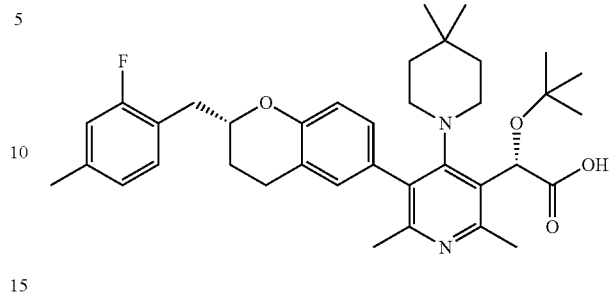

(S)-2-tert-Butoxy-2-(4-(4,4-dimethylpiperidin-1-yl)-5-((R)-2-(2-fluoro-4-methylbenzyl)chroman-6-yl)-2,6-dimethylpyridin-3-yl)acetic acid A mixture of (S)-isopropyl 2-(tert-butoxy)-2-(4-(4,4-dimethylpiperidin-1-yl)-5-((R)-2-(2-fluoro-4-methylbenzyl)chroman-6-yl)-2,6-dimethylpyridin-3-yl)acetate (40 mg, 0.062 mmol), NaOH (0.062 mL, 0.620 mmol) in EtOH (2 mL) was refluxed for 5 h. It was then cooled to rt, filtered and purified by prep HPLC to isolate (S)-2-(tert-butoxy)-2-(4-(4,4-dimethylpiperidin-1-yl)-5-((R)-2-(2-fluoro-4-methylbenzyl)chroman-6-yl)-2,6-dimethylpyridin-3-yl)acetic acid (12 mg, 0.020 mmol, 31.5% yield) as an off-white solid. LCMS (M+H)=603.2.

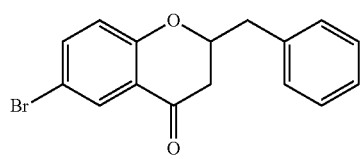 [SMILES: O=C1CC(Cc2ccccc2)Oc2ccc(Br)cc21]

2-Benzyl-6-bromochroman-4-one

To a solution of 6-bromo-4H-chromen-4-one (200 mg, 0.889 mmol) in $CH_2Cl_2$ (1 mL) was added trimethylsilyl trifluoromethane-sulfonate (0.209 mL, 1.155 mmol) at rt. After stirring for 1 h, tetrahydrofuran (7 mL) was added and then cooled to −78° C. To the mixture was added benzylmagnesium bromide (1.284 mL, 1.155 mmol). After stirring for 1 h at −78° C., 1M aqueous $NH_4Cl$ was added and it was warmed to rt and stirred at rt for 2 h. It was then quenched with water. It was then extracted with ether. The organic layer was dried over $MgSO_4$, filtered and concentrated to obtain an oil, which was then purified by biotage, eluting with 10% EtOac/hexane to obtain 2-benzyl-6-bromochroman-4-one (0.86 g, 2.71 mmol, 30.5% yield). $^1H$ NMR (400 MHz, $CDCl_3$) δ 8.00 (d, J=2.4 Hz, 1H), 7.57 (dd, J=8.8, 2.7 Hz, 1H), 7.46-7.18 (m, 4H), 6.95-6.83 (m, 1H), 4.78-4.60 (m, 1H), 3.23 (dd, J=14.1, 6.2 Hz, 1H), 3.06 (dd, J=13.9, 6.4 Hz, 1H), 2.73-2.66 (m, 2H).

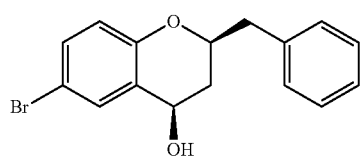 [SMILES: O[C@@H]1C[C@H](Cc2ccccc2)Oc2ccc(Br)cc21]

(2S,4R)-2-Benzyl-6-bromochroman-4-ol

To a mixture of 2-benzyl-6-bromochroman-4-one (500 mg, 1.576 mmol) in MeOH (20 mL) was added NaBH₄ (59.6 mg, 1.576 mmol) at 0° C. and stirred at rt for 1 h. It was then quenched by water, extracted with EtOAc. The organic was dried over MgSO₄, filtered and concentrated to obtain an oil, which was then purified by biotage, eluting with 20% EtOAc/hexane to obtain 2-benzyl-6-bromochroman-4-ol (480 mg, 1.504 mmol, 95% yield). The isomers were separated by a SFC column (chiralCel OJ-H, 21×250 mm, 5 μm), eluting with 10% EtOH/90% CO₂ to obtain one isomer as (2S,4R)-2-benzyl-6-bromochroman-4-ol. LCMS (M+1+Na) =341.0. ¹H NMR (400 MHz, CDCl₃) δ 7.59 (s, 1H), 7.39-7.21 (m, 6H), 6.72 (d, J=8.6 Hz, 1H), 4.95-4.80 (m, 1H), 4.43-4.28 (m, 1H), 3.16 (dd, J=13.7, 6.1 Hz, 1H), 2.96 (dd, J=13.7, 6.8 Hz, 1H), 2.31 (dd, J=13.1, 6.0 Hz, 1H), 1.81-1.67 (m, 2H).

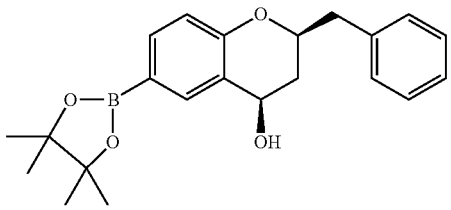 [SMILES: CC1(C)OB(c2ccc3c(c2)[C@H](O)C[C@H](Cc2ccccc2)O3)OC1(C)C]

(2S,4R)-2-Benzyl-6-(4,4,5,5-tetramethyl-1,3,2-dioxaborolan-2-yl)chroman-4-ol A mixture of (2S,4R)-2-benzyl-6-bromochroman-4-ol (150 mg, 0.470 mmol), bis(pinacolato)diboron (179 mg, 0.705 mmol), potassium acetate (138 mg, 1.410 mmol) in dioxane (10 mL) was degassed three times and then filled with N₂. It was then added 1,1'-bis(diphenylphosphino)ferrocene-palladium(ii)dichloride dichloromethane complex (38.4 mg, 0.047 mmol) and heated at 90° C. for 16 h. It was then quenched with water, extracted with EtOAc. The organic layer was dried over MgSO₄, filtered and concentrated. It was then purified by biotage, eluting with 20% EtOAc/hexane to obtain (2S,4R)-2-benzyl-6-(4,4,5,5-tetramethyl-1,3,2-dioxaborolan-2-yl)chroman-4-ol (80 mg, 0.218 mmol, 46.5% yield). ¹H NMR (400 MHz, CDCl₃) δ 7.93 (s, 1H), 7.64 (d, J=8.3 Hz, 1H), 7.37-7.25 (m, 5H), 6.83 (d, J=8.3 Hz, 1H), 4.92 (d, J=4.9 Hz, 1H), 4.38 (dt, J=11.1, 5.7 Hz, 1H), 3.18 (dd, J=13.7, 6.1 Hz, 1H), 2.98 (dd, J=13.6, 6.7 Hz, 1H), 2.33 (dd, J=12.7, 5.9 Hz, 1H), 1.85-1.72 (m, 2H), 1.35 (s, 12H).

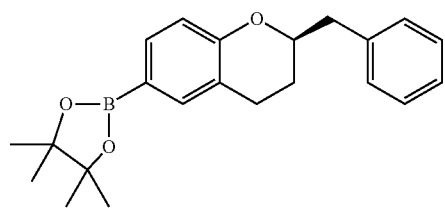 [SMILES: CC1(C)OB(c2ccc3c(c2)CC[C@H](Cc2ccccc2)O3)OC1(C)C]

(R)-2-(2-Benzylchroman-6-yl)-4,4,5,5-tetramethyl-1,3,2-dioxaborolane

A mixture of (2S,4R)-2-benzyl-6-(4,4,5,5-tetramethyl-1,3,2-dioxaborolan-2-yl)chroman-4-ol (140 mg, 0.382 mmol) in CH₂Cl₂ (2 mL) was added triethylsilane (0.488 mL, 3.06 mmol), TFA (0.942 mL, 12.23 mmol) at 0° C. It was then stirred at 0° C. for 0.5 h, then rt for 1 h. It was quenched with NaHCO₃, extracted with EtOAc. The organic was washed with water, dried over MgSO₄, filtered and concentrated to obtain (R)-2-(2-benzylchroman-6-yl)-4,4,5,5-tetramethyl-1,3,2-dioxaborolane (90 mg, 0.257 mmol, 67.2% yield) as an white solid. ¹H NMR (400 MHz, CDCl₃) δ 7.60-7.52 (m, 1H), 7.37-7.23 (m, 5H), 7.14-7.00 (m, 1H), 6.87-6.79 (m, 1H), 4.36-4.19 (m, 1H), 3.22-3.11 (m, 1H), 2.97-2.84 (m, 1H), 2.83-2.75 (m, 2H), 2.01 (d, J=13.4 Hz, 1H), 1.78-1.66 (m, 1H), 1.35 (s, 12H).

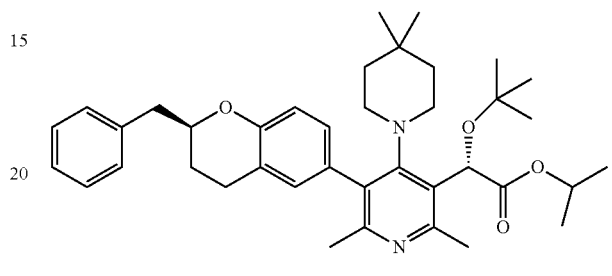

(S)-Isopropyl 2-(5-((S)-2-benzylchroman-6-yl)-4-(4,4-dimethylpiperidin-1-yl)-2,6-dimethylpyridin-3-yl)-2-tert-butoxyacetate A mixture of (R)-2-(2-benzylchroman-6-yl)-4,4,5,5-tetramethyl-1,3,2-dioxaborolane (56.0 mg, 0.160 mmol), (S)-isopropyl 2-(5-bromo-4-(4,4-dimethylpiperidin-1-yl)-6-(hydroxymethyl)-2-methylpyridin-3-yl)-2-(tert-butoxy)acetate (50 mg, 0.103 mmol), potassium phosphate (170 mg, 0.799 mmol) in dioxane (3 mL) and water (0.3 mL) was vacuum, back-filled with N₂ for 3 times. It was then added Pd(Ph₃P)₄ (24.61 mg, 0.021 mmol) and heated at 85° C. for 16 h. It was then diluted with EtOAc, washed with water. The organic was dried over MgSO₄, filtered and concentrated to obtain 50 mg of an oil, which was then purified by biotage, eluting with 25% EtOAc/hexane to isolate (S)-isopropyl 2-(5-((S)-2-benzylchroman-6-yl)-4-(4,4-dimethylpiperidin-1-yl)-2,6-dimethylpyridin-3-yl)-2-(tert-butoxy)acetate (18 mg, 0.029 mmol, 27.6% yield) as a white solid. LCMS (M+H)=613.3.

Example 32

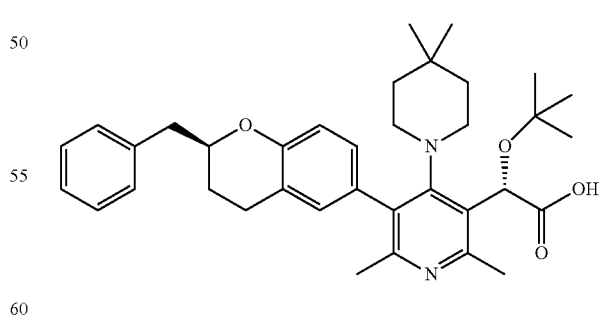

(S)-2-(5-((S)-2-Benzylchroman-6-yl)-4-(4,4-dimethylpiperidin-1-yl)-2,6-dimethylpyridin-3-yl)-2-tert-butoxyacetic acid A mixture of (S)-isopropyl 2-(5-((S)-2-benzylchroman-6-yl)-4-(4,4-dimethylpiperidin-1-yl)-6-(hydroxymethyl)-2- methylpyridin-3-yl)-2-(tert-butoxy)acetate (31 mg, 0.049 mmol), KOH (13.83 mg, 0.246 mmol) in ethanol (2 mL), water (0.2 mL) was refluxed for 16 h. It was then cooled to rt, filtered and purified by perp HPLC to obtain (S)-2-(5-((S)-2-benzylchroman-6-yl)-4-(4,4-dimethylpiperidin-1-yl)-6-(hydroxymethyl)-2-methylpyridin-3-yl)-2-(tert-butoxy)acetic acid (25 mg, 0.043 mmol, 86% yield) as a white solid. LCMS (M+H)=587.5. $^1$H NMR (500 MHz, DMSO-$d_6$) δ 7.36-7.30 (m, 4H), 7.25 (br. s., 1H), 7.00 (d, J=10.6 Hz, 1H), 6.79-6.72 (m, 2H), 5.30 (br. s., 1H), 4.38-4.06 (m, 3H), 4.02-3.86 (m, 1H), 3.45-3.36 (m, 2H), 3.12-3.00 (m, 1H), 2.97-2.86 (m, 1H), 2.84-2.64 (m, 3H), 2.47 (s, 3H), 2.24-2.03 (m, 1H), 1.99 (br. s., 1H), 1.71 (br. s., 1H), 1.51 (br. s., 1H), 1.24 (br. s., 1H), 1.13 (d, J=10.6 Hz, 1H), 1.10-1.03 (m, 9H), 0.97 (d, J=9.9 Hz, 1H), 0.84 (s, 3H), 0.73-0.61 (m, 3H).

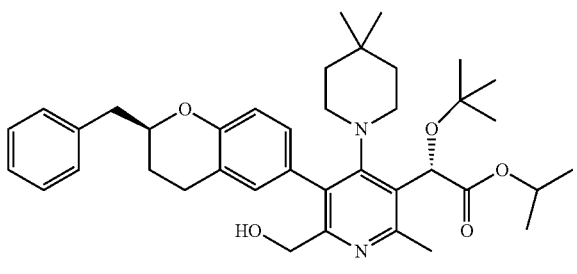 [SMILES: Cc1nc(CO)c(-c2ccc3c(c2)CC[C@@H](Cc2ccccc2)O3)c(N2CCC(C)(C)CC2)c1[C@H](OC(C)(C)C)C(=O)OC(C)C]

(S)-Isopropyl 2-(5-((S)-2-benzylchroman-6-yl)-4-(4, 4-dimethylpiperidin-1-yl)-6-(hydroxymethyl)-2-methylpyridin-3-yl)-2-tert-butoxyacetate A mixture of (R)-2-(2-benzylchroman-6-yl)-4,4,5,5-tetramethyl-1,3,2-dioxaborolane (54.1 mg, 0.154 mmol), (S)-isopropyl 2-(5-bromo-4-(4,4-dimethylpiperidin-1-yl)-6-(hydroxymethyl)-2-methylpyridin-3-yl)-2-(tert-butoxy)acetate (50 mg, 0.103 mmol), potassium phosphate (164 mg, 0.772 mmol) in dioxane (3 mL) and water (0.3 mL) was vacuum, back-filled with $N_2$ for 3 times. It was then added Pd(Ph$_3$P)$_4$ (23.80 mg, 0.021 mmol) and heated at 85° C. for 16 h. It was then diluted with EtOAc, washed with water. The organic was dried over MgSO$_4$, filtered and concentrated to obtain 50 mg of an oil, which was then purified by biotage, eluting with 50% EtOAc/hexane to isolate (S)-isopropyl 2-(5-((S)-2-benzylchroman-6-yl)-4-(4,4-dimethylpiperidin-1-yl)-6-(hydroxymethyl)-2-methylpyridin-3-yl)-2-(tert-butoxy)acetate (31 mg, 0.049 mmol, 47.9% yield) as a white solid. LCMS (M+H)=629.3.

Example 33

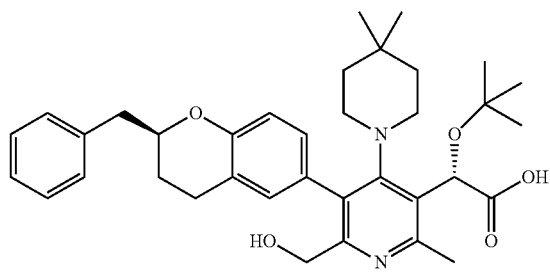 [SMILES: Cc1nc(CO)c(-c2ccc3c(c2)CC[C@@H](Cc2ccccc2)O3)c(N2CCC(C)(C)CC2)c1[C@H](OC(C)(C)C)C(=O)O]

(S)-2-(5-((S)-2-Benzylchroman-6-yl)-4-(4,4-dimethylpiperidin-1-yl)-6-(hydroxymethyl)-2-methylpyridin-3-yl)-2-tert-butoxyacetic acid A mixture of (S)-isopropyl 2-(5-((S)-2-benzylchroman-6-yl)-4-(4,4-dimethylpiperidin-1-yl)-6-(hydroxymethyl)-2-methylpyridin-3-yl)-2-(tert-butoxy)acetate (31 mg, 0.049 mmol), KOH (13.83 mg, 0.246 mmol) in ethanol (2 mL), water (0.2 mL) was refluxed for 16 h. It was then cooled to rt, filtered purified by prep HPLC to obtain (S)-2-(5-((S)-2-benzylchroman-6-yl)-4-(4,4-dimethylpiperidin-1-yl)-6-(hydroxymethyl)-2-methylpyridin-3-yl)-2-(tert-butoxy)acetic acid (25 mg, 0.043 mmol, 86% yield) as a white solid. LCMS (M+H)=587.5. $^1$H NMR (500 MHz, DMSO-$d_6$) δ 7.36-7.30 (m, 4H), 7.25 (br. s., 1H), 7.00 (d, J=10.6 Hz, 1H), 6.79-6.72 (m, 2H), 5.30 (br. s., 1H), 4.38-4.06 (m, 3H), 4.02-3.86 (m, 1H), 3.45-3.36 (m, 2H), 3.12-3.00 (m, 1H), 2.97-2.86 (m, 1H), 2.84-2.64 (m, 3H), 2.47 (s, 3H), 2.24-2.03 (m, 1H), 1.99 (br. s., 1H), 1.71 (br. s., 1H), 1.51 (br. s., 1H), 1.24 (br. s., 1H), 1.13 (d, J=10.6 Hz, 1H), 1.10-1.03 (m, 9H), 0.97 (d, J=9.9 Hz, 1H), 0.84 (s, 3H), 0.73-0.61 (m, 3H).

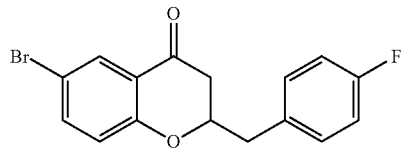 [SMILES: O=C1CC(Cc2ccc(F)cc2)Oc2ccc(Br)cc21]

6-Bromo-2-(4-fluorobenzyl)chroman-4-one

To a mixture of 1-(5-bromo-2-hydroxyphenyl)ethanone (1.3 g, 6.05 mmol) in toluene (5 mL) was added acetic acid (0.346 mL, 6.05 mmol) and pyrrolidine (0.500 mL, 6.05 mmol). It was then stirred at rt for 10 min, then 2-(4-fluorophenyl)acetaldehyde (1.002 g, 7.25 mmol) was added. The mixture was heated to 70° C. for 18 hours. The reaction mixture was concentrated in vacuo. The mixture was diluted with diethyl ether and 1N aqueous NaOH. The phases were separated, and the organic was washed with more water. The combined organic phases were dried (MgSO$_4$), filtered and concentrated. The concentrate was purified by biotage silica gel chromatography, eluting with 10% EtOAc/hexanes to isolate 6-bromo-2-(4-fluorobenzyl)chroman-4-one (500 mg, 1.492 mmol, 24.68% yield). $^1$H NMR (400 MHz, CDCl$_3$) δ 8.00 (d, J=2.2 Hz, 1H), 7.57 (dd, J=8.7, 2.3 Hz, 1H), 7.24 (dd, J=8.2, 5.5 Hz, 2H), 7.05 (t, J=8.6 Hz, 2H), 6.90 (d, J=8.8 Hz, 1H), 4.71-4.60 (m, 1H), 3.22-3.13 (m, 1H), 3.10-3.01 (m, 1H), 2.71-2.66 (m, 2H).

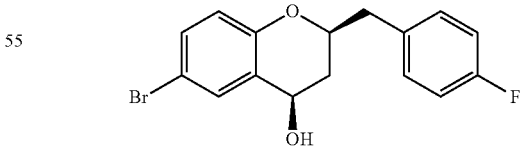

(2S,4R)-6-Bromo-2-(4-fluorobenzyl)chroman-4-ol

A mixture of 6-bromo-2-(4-fluorobenzyl)chroman-4-one (300 mg, 0.895 mmol) in MeOH (10 mL) was added NaBH$_4$ (33.9 mg, 0.895 mmol) and stirred at rt for 1 h. It was then quenched with NH$_4$Cl and extracted with EtOAc. The organic was dried over MgSO₄, filtered and concentrated. The isomers were separated by a SFC column (chiralCel OJ-H, 21×250 mm, 5 μm), eluting with 10% EtOH/90% CO₂ to obtain (2R,4S)-6-bromo-2-(4-fluorobenzyl)chroman-4-ol (100 mg, 0.297 mmol, 33.1% yield) ¹H NMR (400 MHz, CDCl₃) δ 7.59 (d, J=2.2 Hz, 1H), 7.28-7.16 (m, 3H), 7.03 (t, J=8.7 Hz, 2H), 6.70 (d, J=8.6 Hz, 1H), 4.97-4.80 (m, 1H), 4.39-4.24 (m, 1H), 3.18-3.02 (m, 1H), 2.95 (dd, J=13.9, 6.4 Hz, 1H), 2.29 (ddd, J=13.0, 6.3, 1.7 Hz, 1H), 1.80-1.66 (m, 2H).

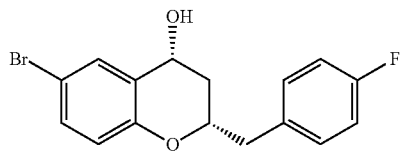 [SMILES: O[C@@H]1C[C@H](Cc2ccc(F)cc2)Oc2ccc(Br)cc21]

(2S,4R)-6-Bromo-2-(4-fluorobenzyl)chroman-4-ol

A mixture of 6-bromo-2-(4-fluorobenzyl)chroman-4-one (300 mg, 0.895 mmol) in MeOH (10 mL) was added NaBH₄ (33.9 mg, 0.895 mmol) and stirred at rt for 1 h. It was then quenched with NH₄Cl and extracted with EtOAc. The organic was dried over MgSO₄, filtered and concentrated. The isomers were separated by a SFC column (chiralCel OJ-H, 21×250 mm, 5 μm), eluting with 10% EtOH/90% CO₂ to (2S,4R)-6-bromo-2-(4-fluorobenzyl)chroman-4-ol (100 mg, 0.297 mmol, 33.1% yield), ¹H NMR (400 MHz, CDCl₃) δ 7.59 (dd, J=2.3, 0.9 Hz, 1H), 7.26-7.18 (m, 2H), 7.10-6.94 (m, 2H), 6.70 (d, J=8.6 Hz, 1H), 4.89 (dd, J=17.1, 7.6 Hz, 1H), 4.32 (dtd, J=11.2, 6.3, 2.0 Hz, 1H), 3.22-3.02 (m, 1H), 3.02-2.83 (m, 1H), 2.29 (ddd, J=13.0, 6.2, 1.8 Hz, 1H), 1.85-1.64 (m, 2H).

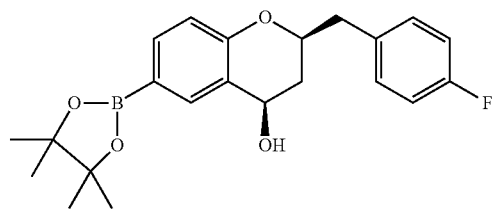 [SMILES: CC1(C)OB(c2ccc3c(c2)[C@H](O)C[C@H](Cc2ccc(F)cc2)O3)OC1(C)C]

(2S,4R)-2-(4-Fluorobenzyl)-6-(4,4,5,5-tetramethyl-1,3,2-dioxaborolan-2-yl)chroman-4-ol A mixture of (2S,4R)-6-bromo-2-(4-fluorobenzyl)chroman-4-ol (130 mg, 0.386 mmol) and potassium acetate (114 mg, 1.157 mmol) in dioxane (3 mL) was degassed three times and then filled with N₂. It was then added 1,1'-bis(diphenylphosphino)-ferrocenepalladium(ii)dichloride dichloromethane complex (31.5 mg, 0.039 mmol) and heated at 90° C. for 16 h. It was then quenched with water, extracted with EtOAc. The organic layer was dried over MgSO₄, filtered and concentrated. It was then purified by biotage, eluting with 50% EtOAc/hexane to obtain (2S,4R)-2-(4-fluorobenzyl)-6-(4,4,5,5-tetramethyl-1,3,2-dioxaborolan-2-yl)chroman-4-ol (140 mg, 0.364 mmol, 95% yield) as a white solid. ¹H NMR (400 MHz, CDCl₃) δ 7.92 (s, 1H), 7.64 (dd, J=8.2, 1.1 Hz, 1H), 7.28-7.23 (m, 2H), 7.07-6.98 (m, 2H), 6.85-6.77 (m, 1H), 4.98-4.86 (m, 1H), 4.35 (dtd, J=11.0, 6.4, 2.0 Hz, 1H), 3.12 (dd, J=13.9, 6.4 Hz, 1H), 2.97 (dd, J=13.9, 6.1 Hz, 1H), 2.31 (ddd, J=13.1, 6.2, 2.0 Hz, 1H), 1.91-1.70 (m, 2H), 1.36-1.33 (m, 12H).

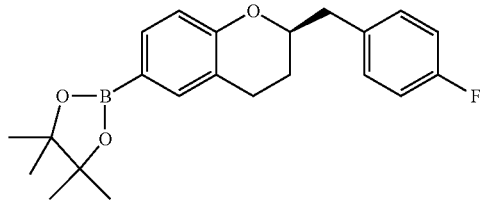 [SMILES: CC1(C)OB(c2ccc3c(c2)CC[C@H](Cc2ccc(F)cc2)O3)OC1(C)C]

(R)-2-(2-(4-Fluorobenzyl)chroman-6-yl)-4,4,5,5-tetramethyl-1,3,2-dioxaborolane

A mixture of (2S,4R)-2-(4-fluorobenzyl)-6-(4,4,5,5-tetramethyl-1,3,2-dioxaborolan-2-yl)chroman-4-ol (140 mg, 0.364 mmol) in DCM (10 mL) was added triethylsilane (0.466 mL, 2.91 mmol), TFA (0.898 mL, 11.66 mmol) and stirred at rt for 3 h. It was then diluted with EtOAc, washed with NaHCO₃, water. The organic was dried over MgSO₄, filtered and concentrated to obtain (R)-2-(2-(4-fluorobenzyl)chroman-6-yl)-4,4,5,5-tetramethyl-1,3,2-dioxaborolane (100 mg, 0.272 mmol, 74.5% yield) as a white solid. ¹H NMR (400 MHz, CDCl₃) δ 7.62-7.51 (m, 2H), 7.27-7.20 (m, 2H), 7.07-6.96 (m, 2H), 6.81 (d, J=8.1 Hz, 1H), 4.22 (t, J=6.4 Hz, 1H), 3.10 (dd, J=13.9, 6.1 Hz, 1H), 2.94-2.73 (m, 3H), 2.00 (d, J=13.0 Hz, 1H), 1.80-1.68 (m, 2H), 1.35 (s, 12H.).

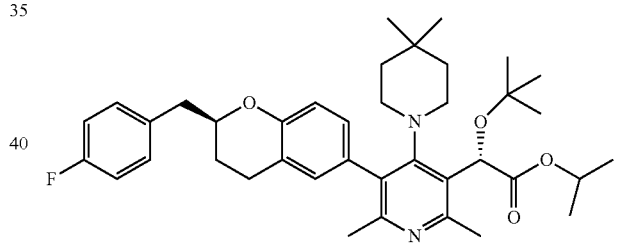

(S)-Isopropyl 2-tert-butoxy-2-(4-(4,4-dimethylpiperidin-1-yl)-5-((S)-2-(4-fluorobenzyl)chroman-6-yl)-2,6-dimethylpyridin-3-yl)acetate A mixture of (R)-2-(2-(4-fluorobenzyl)chroman-6-yl)-4,4,5,5-tetramethyl-1,3,2-dioxaborolane (51.0 mg, 0.138 mmol), (S)-isopropyl 2-(5-bromo-4-(4,4-dimethylpiperidin-1-yl)-2,6-dimethylpyridin-3-yl)-2-(tert-butoxy)acetate (50 mg, 0.107 mmol), potassium phosphate (170 mg, 0.799 mmol) in dioxane (3 mL) and water (0.3 mL) was vacuum, back-filled with N₂ for 3 times. It was then added Pd(Ph₃P)₄ (24.61 mg, 0.021 mmol) and heated at 85° C. for 16 h. It was then diluted with EtOAc, washed with water. The organic was dried over MgSO₄, filtered and concentrated to obtain 50 mg of an oil, which was then purified by biotage, eluting with 25% EtOAc/hexane to isolate (S)-isopropyl 2-(tert-butoxy)-2-(4-(4,4-dimethylpiperidin-1-yl)-5-((S)-2-(4-fluorobenzyl)chroman-6-yl)-2,6-dimethylpyridin-3-yl)acetate (25 mg, 0.040 mmol, 37.2% yield) as a white solid. LCMS (M+H)=631.1.

Example 34

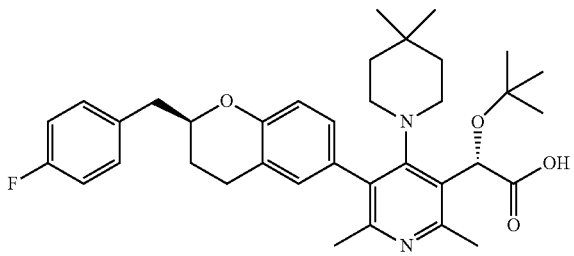 [SMILES: Cc1nc(C)c([C@H](OC(C)(C)C)C(=O)O)c(N2CCC(C)(C)CC2)c1-c1ccc2c(c1)CC[C@@H](Cc1ccc(F)cc1)O2]

(S)-2-tert-Butoxy-2-(4-(4,4-dimethylpiperidin-1-yl)-5-((S)-2-(4-fluorobenzyl)chroman-6-yl)-2,6-dimethylpyridin-3-yl)acetic acid A mixture of (S)-isopropyl 2-(tert-butoxy)-2-(4-(4,4-dimethylpiperidin-1-yl)-5-((S)-2-(4-fluorobenzyl)chroman-6-yl)-2,6-dimethylpyridin-3-yl)acetate (25 mg, 0.040 mmol), KOH (2.223 mg, 0.040 mmol) in EtOH (2 mL) and water (0.2 mL) was refluxed for 16 h. It was then cooled to rt, filtered and purified by prep HPLC to isolate (S)-2-(tert-butoxy)-2-(4-(4,4-dimethylpiperidin-1-yl)-5-((S)-2-(4-fluorobenzyl)chroman-6-yl)-2,6-dimethylpyridin-3-yl)acetic acid (17.8 mg, 0.030 mmol, 76% yield) as a white solid. LCMS (M+H)=589.2.

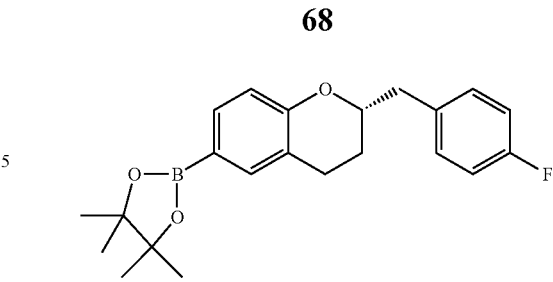

(S)-2-(2-(4-Fluorobenzyl)chroman-6-yl)-4,4,5,5-tetramethyl-1,3,2-dioxaborolane

A mixture of (2R,4S)-2-(4-fluorobenzyl)-6-(4,4,5,5-tetramethyl-1,3,2-dioxaborolan-2-yl)chroman-4-ol (140 mg, 0.364 mmol) in DCM (10 mL) was added triethylsilane (0.466 mL, 2.91 mmol), TFA (0.898 mL, 11.66 mmol) and stirred at rt for 3 h. It was then diluted with EtOAc, washed with NaHCO$_3$, water. The organic was dried over MgSO$_4$, filtered and concentrated to obtain (S)-2-(2-(4-fluorobenzyl)chroman-6-yl)-4,4,5,5-tetramethyl-1,3,2-dioxaborolane (100 mg, 0.272 mmol, 74.5% yield) as a white solid. $^1$H NMR (400 MHz, CDCl$_3$) δ 7.64-7.50 (m, 2H), 7.25 (dd, J=8.7, 5.3 Hz, 2H), 7.05-6.96 (m, 2H), 6.81 (d, J=8.1 Hz, 1H), 4.29-4.14 (m, 1H), 3.14-3.05 (m, 1H), 2.94-2.76 (m, 3H), 2.08-1.96 (m, 1H), 1.39-1.31 (m, 12H).

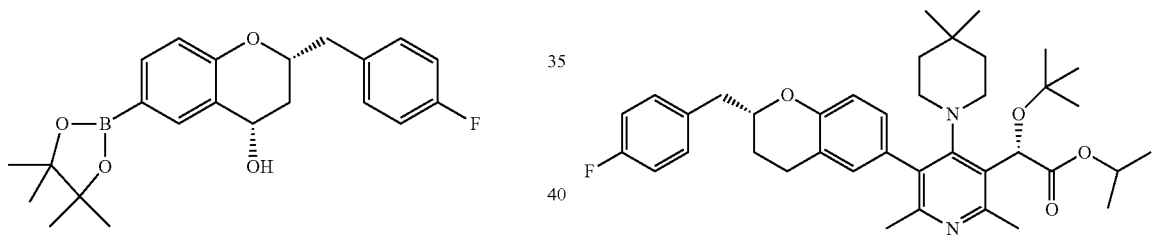

(2R,4S)-2-(4-Fluorobenzyl)-6-(4,4,5,5-tetramethyl-1,3,2-dioxaborolan-2-yl)chroman-4-ol A mixture of (2R,4S)-6-bromo-2-(4-fluorobenzyl)chroman-4-ol (130 mg, 0.386 mmol), 4,4,4',4',5,5,5',5'-octamethyl-2,2'-bi(1,3,2-dioxaborolane) (147 mg, 0.578 mmol), in dioxane (3 mL) was degassed three times and then filled with N$_2$. It was then added 1,1'-bis(diphenylphosphino)ferrocene-palladium(II)dichloride dichloromethane complex (31.5 mg, 0.039 mmol)) and heated at 90° C. for 16 h. It was then quenched with water, extracted with EtOAc. The organic layer was dried over MgSO$_4$, filtered and concentrated. It was then purified by biotage, eluting with 50% EtOAc/hexane to obtain (2R,4S)-2-(4-fluorobenzyl)-6-(4,4,5,5-tetramethyl-1,3,2-dioxaborolan-2-yl)chroman-4-ol (90 mg, 0.234 mmol, 60.8% yield) as a white solid. $^1$H NMR (400 MHz, CDCl$_3$) δ 7.92 (s, 1H), 7.64 (dd, J=8.2, 1.1 Hz, 1H), 7.28-7.22 (m, 2H), 7.05-6.99 (m, 2H), 6.82 (d, J=8.1 Hz, 1H), 4.92 (br. s., 1H), 4.35 (dtd, J=10.9, 6.3, 2.0 Hz, 1H), 3.12 (dd, J=13.9, 6.4 Hz, 1H), 2.97 (dd, J=13.9, 6.4 Hz, 1H), 2.31 (ddd, J=13.1, 6.2, 2.0 Hz, 1H), 1.87-1.71 (m, 2H), 1.35 (s, 12H).

(S)-Isopropyl 2-tert-butoxy-2-(4-(4,4-dimethylpiperidin-1-yl)-5-((R)-2-(4-fluorobenzyl)chroman-6-yl)-2,6-dimethylpyridin-3-yl)acetate A mixture of (S)-2-(2-(4-fluorobenzyl)chroman-6-yl)-4,4,5,5-tetramethyl-1,3,2-dioxaborolane (51.0 mg, 0.138 mmol), (S)-isopropyl 2-(5-bromo-4-(4,4-dimethylpiperidin-1-yl)-2,6-dimethylpyridin-3-yl)-2-(tert-butoxy)acetate (50 mg, 0.107 mmol), potassium phosphate (170 mg, 0.799 mmol) in dioxane (3 mL) and water (0.3 mL) was vacuum, back-filled with N$_2$ for 3 times. It was then added Pd(Ph$_3$P)$_4$ (24.61 mg, 0.021 mmol) and heated at 85° C. for 16 h. It was then diluted with EtOAc, washed with water. The organic was dried over MgSO$_4$, filtered and concentrated to obtain 50 mg of an oil, which was then purified by biotage, eluting with 25% EtOAc/hexane to isolate(S)-isopropyl 2-(tert-butoxy)-2-(4-(4,4-dimethylpiperidin-1-yl)-5-((R)-2-(4-fluorobenzyl)chroman-6-yl)-2,6-dimethylpyridin-3-yl)acetate (15 mg, 0.024 mmol, 22.33% yield) as a white solid. LCMS (M+H)=631.1.

Example 35

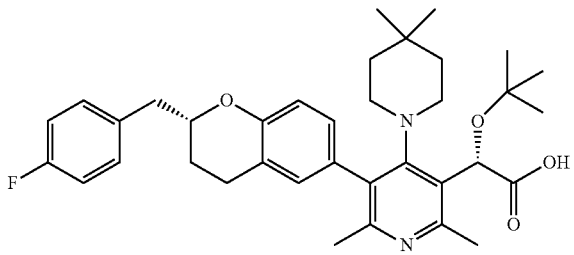 [SMILES: Cc1nc(C)c([C@H](OC(C)(C)C)C(=O)O)c(N2CCC(C)(C)CC2)c1-c1ccc2c(c1)CC[C@H](Cc1ccc(F)cc1)O2]

(S)-2-tert-Butoxy-2-(4-(4,4-dimethylpiperidin-1-yl)-5-((R)-2-(4-fluorobenzyl)chroman-6-yl)-2,6-dimethylpyridin-3-yl)acetic acid A mixture of (S)-isopropyl 2-(tert-butoxy)-2-(4-(4,4-dimethylpiperidin-1-yl)-5-((R)-2-(4-fluorobenzyl)chroman-6-yl)-2,6-dimethylpyridin-3-yl)acetate (18 mg, 0.029 mmol), KOH (8.00 mg, 0.143 mmol) in ethanol (2 mL) and water (0.2 mL) and refluxed for 16 h. It was then cooled to rt, filtered and purified by prep HPLC to obtain (S)-2-(tert-butoxy)-2-(4-(4,4-dimethylpiperidin-1-yl)-5-((R)-2-(4-fluorobenzyl)chroman-6-yl)-2,6-dimethylpyridin-3-yl)acetic acid (15 mg, 0.025 mmol, 89% yield) as a white solid. LCMS (M+H)=587.5.

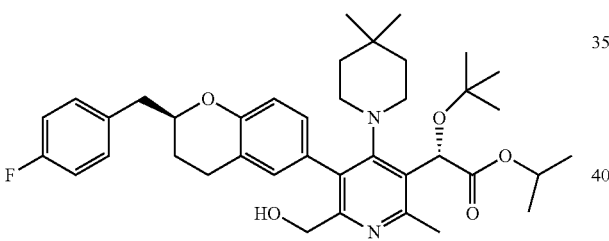

(S)-Isopropyl 2-tert-butoxy-2-(4-(4,4-dimethylpiperidin-1-yl)-5-((S)-2-(4-fluorobenzyl)chroman-6-yl)-6-(hydroxymethyl)-2-methylpyridin-3-yl)acetate A mixture of (S)-isopropyl 2-(5-bromo-4-(4,4-dimethylpiperidin-1-yl)-6-(hydroxymethyl)-2-methylpyridin-3-yl)-2-(tert-butoxy)acetate (20 mg, 0.041 mmol), (R)-2-(2-(4-fluorobenzyl)chroman-6-yl)-4,4,5,5-tetramethyl-1,3,2-dioxaborolane (22.76 mg, 0.062 mmol), potassium phosphate tribasic (65.6 mg, 0.309 mmol) in dioxane (3 mL), water (0.3 mL) was vacuum, back-filled with $N_2$ for 3 times. It was then added Pd(Ph3P)4 (9.52 mg, 8.24 µmol) and heated at 85° C. for 16 h. It was then diluted with EtOAc, washed with water. The organic was dried over $MgSO_4$, filtered and concentrated to obtain 40 mg of an oil, which was then purified by biotage, eluting with 50% EtOAc/hexane to isolate(S)-isopropyl 2-(tert-butoxy)-2-(4-(4,4-dimethylpiperidin-1-yl)-5-((S)-2-(4-fluorobenzyl)chroman-6-yl)-6-(hydroxymethyl)-2-methylpyridin-3-yl)acetate (10 mg, 0.015 mmol, 37.5% yield) as a white solid. LCMS (M+H)=647.2.

Example 36

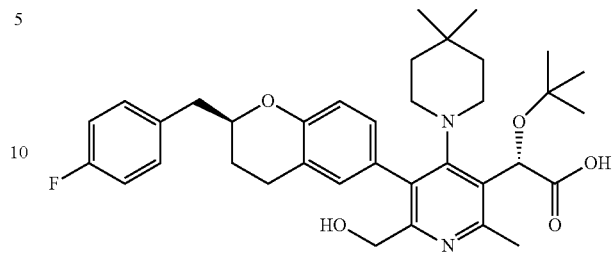

(S)-2-(tert-Butoxy)-2-(4-(4,4-dimethylpiperidin-1-yl)-5-((S)-2-(4-fluorobenzyl)chroman-6-yl)-6-(hydroxymethyl)-2-methylpyridin-3-yl)acetic acid A mixture of (S)-isopropyl 2-(tert-butoxy)-2-(4-(4,4-dimethylpiperidin-1-yl)-5-((S)-2-(4-fluorobenzyl)chroman-6-yl)-6-(hydroxymethyl)-2-methylpyridin-3-yl)acetate (10 mg, 0.015 mmol), KOH (0.867 mg, 0.015 mmol) in ethanol (2 mL), water (0.2 mL) was heated at 85° C. for 16 h. It was then cooled to rt, filtered and purified by prep HPLC to isolate (S)-2-(tert-butoxy)-2-(4-(4,4-dimethylpiperidin-1-yl)-5-((S)-2-(4-fluorobenzyl)chroman-6-yl)-6-(hydroxymethyl)-2-methylpyridin-3-yl)acetic acid (5.8 mg, 9.59 µmol, 62.0% yield) as a white solid. LCMS (M+H)=605.2. $^1$H NMR (500 MHz, DMSO-d$_6$) δ 7.45-7.26 (m, 2H), 7.21-7.07 (m, 2H), 7.08-6.93 (m, 1H), 6.88-6.71 (m, 2H), 5.78 (d, J=11.4 Hz, 1H), 4.34-4.13 (m, 2H), 4.07-3.96 (m, 1H), 3.07-2.88 (m, 2H), 2.87-2.69 (m, 3H), 2.50 (s, 3H), 2.29-2.07 (m, 1H), 2.00 (br. s., 1H), 1.76-1.62 (m, 1H), 1.49 (br. s., 1H), 1.33-1.16 (m, 2H), 1.15-1.09 (m, 9H), 1.01 (d, J=13.2 Hz, 1H), 0.85 (br. s., 3H), 0.64 (br. s., 3H).

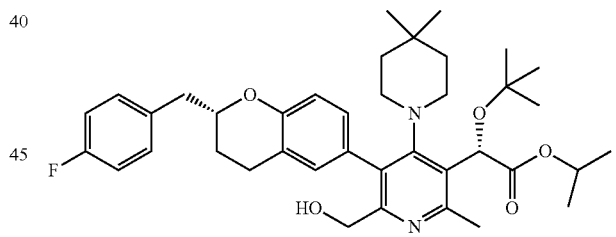

(S)-Isopropyl 2-tert-butoxy-2-(4-(4,4-dimethylpiperidin-1-yl)-5-((R)-2-(4-fluorobenzyl)chroman-6-yl)-6-(hydroxymethyl)-2-methylpyridin-3-yl)acetate A mixture of (S)-isopropyl 2-(5-bromo-4-(4,4-dimethylpiperidin-1-yl)-6-(hydroxymethyl)-2-methylpyridin-3-yl)-2-(tert-butoxy)acetate (20 mg, 0.041 mmol), (S)-2-(2-(4-fluorobenzyl)chroman-6-yl)-4,4,5,5-tetramethyl-1,3,2-dioxaborolane (22.76 mg, 0.062 mmol) in dioxane (3 mL), water (0.3 mL) was vacuum, back-filled with $N_2$ for 3 times. It was then added Pd(Ph$_3$P)$_4$ (9.52 mg, 8.24 µmol) and heated at 85° C. for 16 h. It was then diluted with EtOAc, washed with water. The organic was dried over $MgSO_4$, filtered and concentrated to obtain 50 mg of an oil, which was then purified by biotage, eluting with 50% EtOAc/hexane to isolate(S)-isopropyl 2-(tert-butoxy)-2-(4-(4,4-dimethylpiperidin-1-yl)-5-((R)-2-(4-fluorobenzyl)chroman-6- yl)-6-(hydroxymethyl)-2-methylpyridin-3-yl)acetate (10 mg, 0.015 mmol, 37.5% yield) as a white solid. LCMS (M+H)=647.2.

Example 37

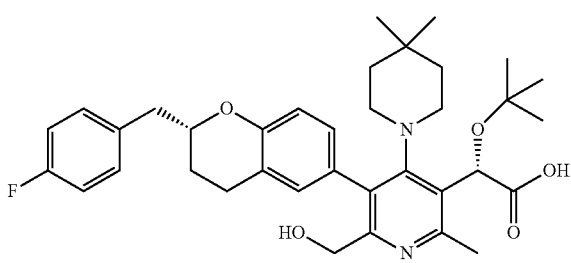 [SMILES: Cc1nc(CO)c(-c2ccc3c(c2)CC[C@H](Cc2ccc(F)cc2)O3)c(N2CCC(C)(C)CC2)c1[C@H](OC(C)(C)C)C(=O)O]

(S)-2-tert-Butoxy-2-(4-(4,4-dimethylpiperidin-1-yl)-5-((R)-2-(4-fluorobenzyl)chroman-6-yl)-6-(hydroxymethyl)-2-methylpyridin-3-yl)acetic acid A mixture of (S)-isopropyl 2-(tert-butoxy)-2-(4-(4,4-dimethylpiperidin-1-yl)-5-((R)-2-(4-fluorobenzyl)chroman-6-yl)-6-(hydroxymethyl)-2-methylpyridin-3-yl)acetate (10 mg, 0.015 mmol) and KOH (0.867 mg, 0.015 mmol) in EtOH (2 mL)/water (0.2 mL) was refluxed for 16 h. It was then filtered and purified by prep HPLC to isolate (S)-2-(tert-butoxy)-2-(4-(4,4-dimethylpiperidin-1-yl)-5-((R)-2-(4-fluorobenzyl)chroman-6-yl)-6-(hydroxymethyl)-2-methylpyridin-3-yl)acetic acid (2.7 mg, 4.46 μmol, 28.9% yield) as a white solid. LCMS (M+H)=605.1. $^1$H NMR (500 MHz, DMSO-$d_6$) δ 7.43-7.29 (m, 2H), 7.15 (t, J=8.6 Hz, 2H), 7.06-6.95 (m, 1H), 6.87-6.63 (m, 2H), 5.70 (d, J=6.6 Hz, 1H), 4.42-4.16 (m, 2H), 4.08-3.85 (m, 1H), 3.11-2.87 (m, 2H), 2.86-2.69 (m, 3H), 2.50 (br. s., 3H), 2.30-2.07 (m, 1H), 2.07-1.93 (m, 1H), 1.64 (br. s., 1H), 1.50 (br. s., 1H), 1.37-1.14 (m, 2H), 1.11 (s, 9H), 1.07-0.94 (m, 1H), 0.86 (br. s., 3H), 0.74-0.56 (m, 3H).

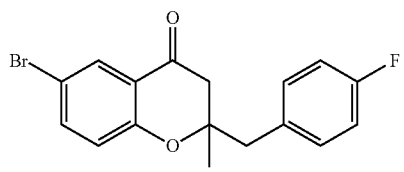 [SMILES: CC1(Cc2ccc(F)cc2)CC(=O)c2cc(Br)ccc2O1]

6-Bromo-2-(4-fluorobenzyl)-2-methylchroman-4-one

To a mixture of 1-(5-bromo-2-hydroxyphenyl)ethanone (1 g, 4.65 mmol) in toluene (5 mL), 1-(4-fluorophenyl)propan-2-one (0.849 g, 5.58 mmol) was added acetic acid (0.266 mL, 4.65 mmol) and pyrrolidine (0.385 mL, 4.65 mmol). The mixture was heated to 70° C. for 18 hours. The reaction mixture was concentrated in vacuo. The mixture was diluted with diethyl ether and 1N aqueous NaOH. The phases were separated, and the organic was washed with more water. The combined organic phases were dried (MgSO$_4$), filtered and concentrated. The residue was purified by biotage silica gel chromatography, eluting with 10% EtOAc/hexane to isolate 6-bromo-2-(4-fluorobenzyl)-2-methylchroman-4-one (0.93 g, 2.66 mmol, 57.3% yield). LCMS (M+H)=350.8. $^1$H NMR (400 MHz, CDCl$_3$) δ 7.99 (d, J=2.4 Hz, 1H), 7.59 (dd, J=8.8, 2.4 Hz, 1H), 7.21-7.12 (m, 2H), 7.08-6.96 (m, 2H), 6.89 (d, J=8.8 Hz, 1H), 3.09-2.93 (m, 2H), 2.81-2.57 (m, 2H), 1.40 (s, 3H).

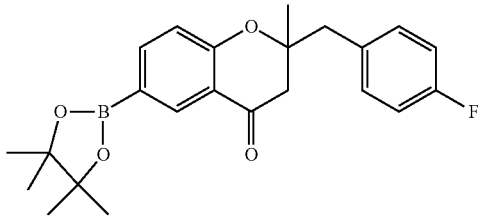 [SMILES: CC1(Cc2ccc(F)cc2)CC(=O)c2cc(B3OC(C)(C)C(C)(C)O3)ccc2O1]

2-(4-Fluorobenzyl)-2-methyl-6-(4,4,5,5-tetramethyl-1,3,2-dioxaborolan-2-yl)chroman-4-one A mixture of 6-bromo-2-(4-fluorobenzyl)-2-methylchroman-4-one (120 mg, 0.344 mmol), bis(pinacolato)diboron (131 mg, 0.515 mmol), potassium acetate (101 mg, 1.031 mmol) in dioxane (3 mL) was degassed three times and then filled with N$_2$. It was then added 1,1'-bis(diphenylphosphino)ferrocene-palladium(II)dichloride dichloromethane complex (28.1 mg, 0.034 mmol) and heated at 90° C. for 16 h. It was then quenched with water, extracted with EtOAc. The organic layer was dried over MgSO$_4$, filtered and concentrated. It was then purified by biotage, eluting with 20% EtOAc/hexane to obtain 2-(4-fluorobenzyl)-2-methyl-6-(4,4,5,5-tetramethyl-1,3,2-dioxaborolan-2-yl)chroman-4-one (120 mg, 0.303 mmol, 88% yield). LCMS (M+H)=396.9. $^1$H NMR (400 MHz, CDCl$_3$) δ 8.38 (s, 1H), 7.93 (d, J=8.3 Hz, 1H), 7.16 (dd, J=8.1, 5.6 Hz, 2H), 7.06-6.87 (m, 3H), 3.11-2.91 (m, 2H), 2.82-2.59 (m, 2H), 1.39 (s, 3H), 1.35 (s, 12H), 1.29 (s, 9H).

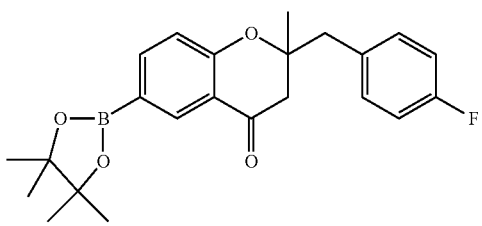 [SMILES: CC1(Cc2ccc(F)cc2)CC(=O)c2cc(B3OC(C)(C)C(C)(C)O3)ccc2O1]

2-(4-Fluorobenzyl)-2-methyl-6-(4,4,5,5-tetramethyl-1,3,2-dioxaborolan-2-yl)chroman-4-one A mixture of 6-bromo-2-(4-fluorobenzyl)-2-methylchroman-4-one (740 mg, 2.119 mmol), bis(pinacolato)diboron (807 mg, 3.18 mmol), potassium acetate (624 mg, 6.36 mmol) in dioxane (15 mL) was degassed three times and then filled with N$_2$. It was then added 1,1'-bis(diphenylphosphino)ferrocene-palladium(II)dichloride dichloromethane complex (173 mg, 0.212 mmol) and heated at 90° C. for 16 h. It was then quenched with water, extracted with EtOAc. The organic layer was dried over MgSO$_4$, filtered and concentrated. It was then purified by biotage, eluting with 20% EtOAc/hexane to obtain 2-(4-fluorobenzyl)-2-methyl-6-(4,4,5,5-tetramethyl-1,3,2-dioxaborolan-2-yl)chroman-4-one (500 mg, 1.262 mmol, 59.5% yield) as a white solid. LCMS (M+H)=396.9. $^1$H NMR (400 MHz, CDCl$_3$) δ 8.38 (s, 1H), 7.93 (d, J=8.3 Hz, 1H), 7.20-7.13 (m, 2H), 7.04-6.92 (m, 3H), 3.09-2.92 (m, 2H), 2.80-2.62 (m, 2H), 1.39 (s, 3H), 1.35 (s, 12H).

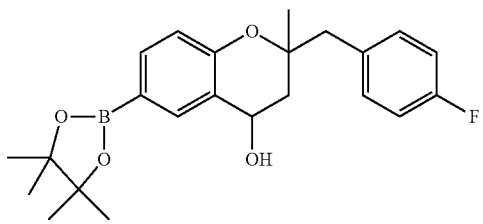 [SMILES: CC1(Cc2ccc(F)cc2)CC(O)c2cc(B3OC(C)(C)C(C)(C)O3)ccc2O1]

2-(4-Fluorobenzyl)-2-methyl-6-(4,4,5,5-tetramethyl-1,3,2-dioxaborolan-2-yl)chroman-4-ol To a mixture of 2-(4-fluorobenzyl)-2-methyl-6-(4,4,5,5-tetramethyl-1,3,2-dioxaborolan-2-yl)chroman-4-one (100 mg, 0.252 mmol) in MeOH (5 mL) was added NaBH$_4$ (9.55 mg, 0.252 mmol) at 0° C. and stirred at rt for 1 h. It was then quenched by water, extracted with EtOAc. The organic was dried over MgSO$_4$, filtered and concentrated to obtain an oil, which was then purified by biotage, eluting with 20% EtOAc/hexane to obtain 2-(4-fluorobenzyl)-2-methyl-6-(4,4,5,5-tetramethyl-1,3,2-dioxaborolan-2-yl)chroman-4-ol (60 mg, 0.151 mmol, 59.7% yield) as a white solid. $^1$H NMR (400 MHz, CDCl$_3$) δ 7.93 (s, 1H), 7.73-7.65 (m, 1H), 7.25 (dd, J=7.8, 5.9 Hz, 1H), 7.19-7.12 (m, 1H), 6.99 (t, J=8.6 Hz, 2H), 6.87 (t, J=7.6 Hz, 1H), 5.02-4.87 (m, 1H), 3.08-2.75 (m, 2H), 2.25-2.10 (m, 1H), 2.00-1.75 (m, 2H), 1.36 (d, J=3.7 Hz, 12H), 1.28 (s, 3H).

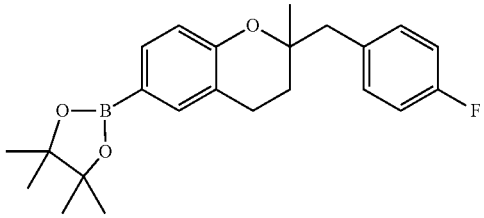 [SMILES: CC1(Cc2ccc(F)cc2)CCc2cc(B3OC(C)(C)C(C)(C)O3)ccc2O1]

2-(2-(4-Fluorobenzyl)-2-methylchroman-6-yl)-4,4,5,5-tetramethyl-1,3,2-dioxaborolane To a mixture of 2-(4-fluorobenzyl)-2-methyl-6-(4,4,5,5-tetramethyl-1,3,2-dioxaborolan-2-yl)chroman-4-ol (65 mg, 0.163 mmol) in CH$_2$Cl$_2$ (2 mL) was added triethylsilane (0.209 mL, 1.306 mmol) and then TFA (0.402 mL, 5.22 mmol). It was then stirred at rt for 1 h. It was then diluted with EtOAc, washed with NaHCO$_3$. The organic was dried over MgSO$_4$, filtered and concentrated to obtain an oil, which was then purified by biotage, eluting with 20% EtOAc/hexane to obtain 2-(2-(4-fluorobenzyl)-2-methylchroman-6-yl)-4,4,5,5-tetramethyl-1,3,2-dioxaborolane (50 mg, 0.131 mmol, 80% yield). LCMS (M+H)=382.9.

(2S)-Isopropyl 2-tert-butoxy-2-(4-(4,4-dimethylpiperidin-1-yl)-5-(2-(4-fluorobenzyl)-2-methylchroman-6-yl)-2,6-dimethylpyridin-3-yl)acetate A mixture of (S)-isopropyl 2-(5-bromo-4-(4,4-dimethylpiperidin-1-yl)-2,6-dimethylpyridin-3-yl)-2-(tert-butoxy)acetate (50 mg, 0.107 mmol), 2-(2-(4-fluorobenzyl)-2-methylchroman-6-yl)-4,4,5,5-tetramethyl-1,3,2-dioxaborolane (61.1 mg, 0.160 mmol) in DMF (2 mL) was vacuum, back-filled with N$_2$ for 3 times. It was then added Pd(Ph$_3$P)$_4$ (24.61 mg, 0.021 mmol) and heated at 85° C. for 16 h. It was then diluted with EtOAc, washed with water. The organic was dried over MgSO$_4$, filtered and concentrated to obtain 50 mg of an oil, which was then purified by biotage, eluting with 25% acetone/hexane to isolate (2S)-isopropyl 2-(tert-butoxy)-2-(4-(4,4-dimethylpiperidin-1-yl)-5-(2-(4-fluorobenzyl)-2-methylchroman-6-yl)-2,6-dimethylpyridin-3-yl)acetate (30 mg, 0.047 mmol, 43.7% yield) white solid. LCMS (M+H)=645.3.

Example 38

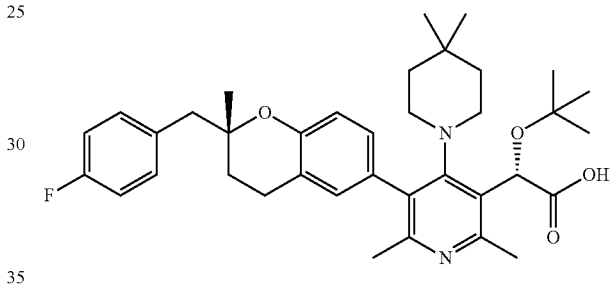

(S)-2-tert-Butoxy-2-(4-(4,4-dimethylpiperidin-1-yl)-5-((R)-2-(4-fluorobenzyl)-2-methylchroman-6-yl)-2,6-dimethylpyridin-3-yl)acetic acid A mixture of (2S)-isopropyl 2-(tert-butoxy)-2-(4-(4,4-dimethylpiperidin-1-yl)-5-(2-(4-fluorobenzyl)-2-methylchroman-6-yl)-2,6-dimethylpyridin-3-yl)acetate (20 mg, 0.031 mmol), KOH (1.740 mg, 0.031 mmol) in EtOH (2 mL), water (0.5 mL) and heated at reflux for 16 h. It was then cooled to rt, filtered and purified by prep HPLC to isolate (S)-2-(tert-butoxy)-2-(4-(4,4-dimethylpiperidin-1-yl)-5-((R)-2-(4-fluorobenzyl)-2-methylchroman-6-yl)-2,6-dimethylpyridin-3-yl)acetic acid (8.9 mg, 0.015 mmol, 47.6% yield) as a white solid. LCMS (M+H)=603.2.

Example 39

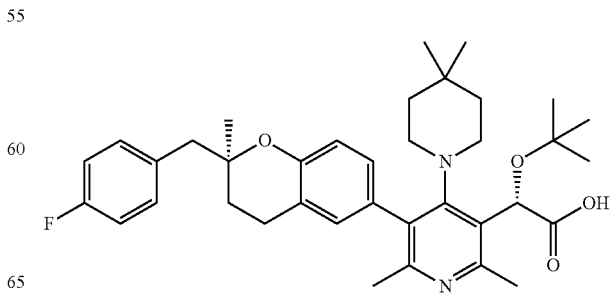

(S)-2-tert-Butoxy-2-(4-(4,4-dimethylpiperidin-1-yl)-5-((S)-2-(4-fluorobenzyl)-2-methylchroman-6-yl)-2,6-dimethylpyridin-3-yl)acetic acid A mixture of (2S)-isopropyl 2-(tert-butoxy)-2-(4-(4,4-dimethylpiperidin-1-yl)-5-(2-(4-fluorobenzyl)-2-methylchroman-6-yl)-2,6-dimethylpyridin-3-yl)acetate (20 mg, 0.031 mmol), KOH (1.740 mg, 0.031 mmol) in EtOH (2 mL), water (0.5 mL) and heated at reflux for 16 h. It was then cooled to rt, filtered and purified by prep HPLC to isolate (S)-2-(tert-butoxy)-2-(4-(4,4-dimethylpiperidin-1-yl)-5-((S)-2-(4-fluorobenzyl)-2-methylchroman-6-yl)-2,6-dimethylpyridin-3-yl)acetic acid (2.3 mg, 3.82 µmol, 12.30% yield) as a white solid. LCMS (M+H)=603.1.

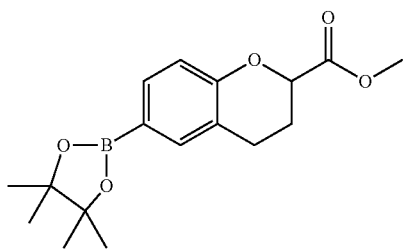

Methyl 6-(4,4,5,5-tetramethyl-1,3,2-dioxaborolan-2-yl)chroman-2-carboxylate

A mixture of methyl 6-bromochroman-2-carboxylate (300 mg, 1.107 mmol), bis(pinacolato)diboron (422 mg, 1.660 mmol), potassium acetate (326 mg, 3.32 mmol) in dioxane (5 mL) was degassed three times and then filled with $N_2$. It was then added 1,1'-bis(diphenylphosphino)ferrocene-palladium(II)dichloride dichloromethane complex (90 mg, 0.111 mmol) and heated at 90° C. for 16 h. It was then quenched with water, extracted with EtOAc. The organic layer was dried over $MgSO_4$, filtered and concentrated. It was then purified by biotage, eluting with 20% EtOAc/hexane to obtain methyl 6-(4,4,5,5-tetramethyl-1,3,2-dioxaborolan-2-yl)chroman-2-carboxylate (350 mg, 1.100 mmol, 99% yield). LCMS (M+H)=319.0. $^1$H NMR (400 MHz, $CDCl_3$) δ 7.60 (d, J=8.3 Hz, 1H), 7.54 (s, 1H), 6.95 (d, J=8.1 Hz, 1H), 4.78 (dd, J=7.2, 3.8 Hz, 1H), 3.81 (s, 3H), 2.98-2.70 (m, 2H), 2.42-2.16 (m, 2H), 1.35 (s, 12H).

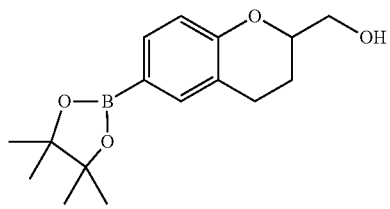 [SMILES: CC1(C)OB(c2ccc3c(c2)CCC(CO)O3)OC1(C)C]

(6-(4,4,5,5-Tetramethyl-1,3,2-dioxaborolan-2-yl)chroman-2-yl)methanol

A mixture of methyl 6-(4,4,5,5-tetramethyl-1,3,2-dioxaborolan-2-yl)chroman-2-carboxylate (160 mg, 0.503 mmol) in THF (5 mL) was added LAH (0.603 mL, 0.603 mmol) at 0° C. and stirred at 0° C. for 2 h. It was then diluted with $NH_4Cl$, extracted with EtOAc. The organic was dried over $MgSO_4$, filtered and concentrated. The residue was purified by biotage, eluting with 20% EtOAc/hexane to obtain (6-(4,4,5,5-tetramethyl-1,3,2-dioxaborolan-2-yl)chroman-2-yl)methanol (100 mg, 0.345 mmol, 68.5% yield). $^1$H NMR (400 MHz, $CDCl_3$) δ 7.67-7.51 (m, 2H), 6.93-6.73 (m, 1H), 4.26-4.05 (m, 1H), 3.95-3.68 (m, 2H), 3.03-2.68 (m, 2H), 2.04-1.93 (m, 2H), 1.93-1.76 (m, 1H), 1.43-1.32 (s, 12H).

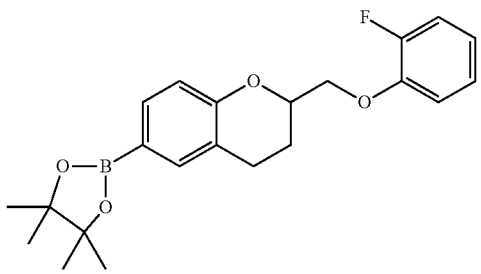 [SMILES: CC1(C)OB(c2ccc3c(c2)CCC(COc2ccccc2F)O3)OC1(C)C]

2-(2-((2-Fluorophenoxy)methyl)chroman-6-yl)-4,4,5,5-tetramethyl-1,3,2-dioxaborolane A mixture of 2-fluorophenol (15.45 mg, 0.138 mmol), triphenylphosphine (36.2 mg, 0.138 mmol) in THF (2 mL) at rt was added (Z)-diisopropyl diazene-1,2-dicarboxylate (0.027 mL, 0.138 mmol) and stirred at rt for 10 min, then (6-(4,4,5,5-tetramethyl-1,3,2-dioxaborolan-2-yl)chroman-2-yl)methanol (20 mg, 0.069 mmol) was added and stirred at rt for 1 h. It was then concentrated and purified by biotage, eluting with 25% EtOAc/hexane to obtain 2-(2-((2-fluorophenoxy)methyl)chroman-6-yl)-4,4,5,5-tetramethyl-1,3,2-dioxaborolane (22 mg, 0.057 mmol, 83% yield) as a colorless oil. LCMS (M+Na)=406.9.

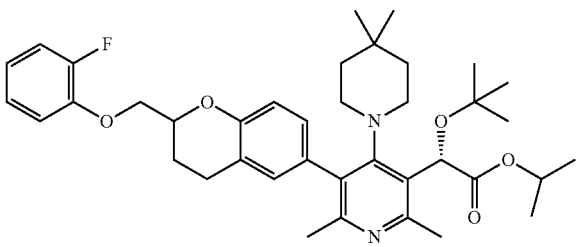 [SMILES: Cc1nc(C)c([C@H](OC(C)(C)C)C(=O)OC(C)C)c(N2CCC(C)(C)CC2)c1-c1ccc2c(c1)CCC(COc1ccccc1F)O2]

(2S)-Isopropyl 2-tert-butoxy-2-(4-(4,4-dimethylpiperidin-1-yl)-5-(2-((2-fluorophenoxy)methyl)chroman-6-yl)-2,6-dimethylpyridin-3-yl)acetate A mixture of (S)-isopropyl 2-(5-bromo-4-(4,4-dimethylpiperidin-1-yl)-2,6-dimethylpyridin-3-yl)-2-(tert-butoxy)acetate (20 mg, 0.043 mmol), 2-(2-((2-fluorophenoxy)methyl)-chroman-6-yl)-4,4,5,5-tetramethyl-1,3,2-dioxaborolane (21.28 mg, 0.055 mmol) in dioxane (3 mL) and water (0.3 mL) was vacuum, back-filled with $N_2$ for 3 times. It was then added $Pd(Ph_3P)_4$ (9.85 mg, 8.52 µmol) and heated at 85° C. for 16 h. It was then diluted with EtOAc, washed with water. The organic was dried over $MgSO_4$, filtered and concentrated to obtain 50 mg of an oil, which was then purified by biotage, eluting with 25% EtOAc/hexane to isolate (2S)-isopropyl 2-(tert-butoxy)-2-(4-(4,4-dimethylpiperidin-1-yl)-5-(2-((2-fluorophenoxy)methyl)

chroman-6-yl)-2,6-dimethylpyridin-3-yl)acetate (12 mg, 0.019 mmol, 43.5% yield) as a white solid. LCMS (M+H)=647.1.

Example 40

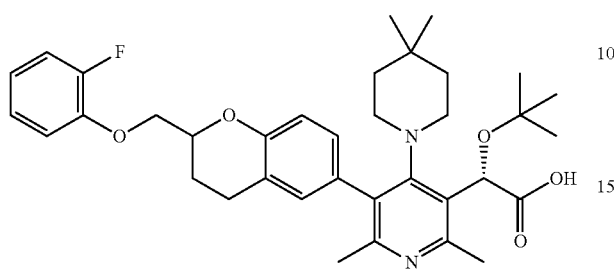

(2S)-2-tert-Butoxy-2-(4-(4,4-dimethylpiperidin-1-yl)-5-(2-((2-fluorophenoxy)methyl)chroman-6-yl)-2,6-dimethylpyridin-3-yl)acetic acid A mixture of (2S)-isopropyl 2-(tert-butoxy)-2-(4-(4,4-dimethylpiperidin-1-yl)-5-(2-((2-fluorophenoxy)methyl)chroman-6-yl)-2,6-dimethylpyridin-3-yl)acetate (12 mg, 0.019 mmol), KOH (1.041 mg, 0.019 mmol) in ethanol (2 mL), water (1 mL) was refluxed for 16 h. It was then filtered and purified by prep HPLC to obtain (2S)-2-(tert-butoxy)-2-(4-(4,4-dimethylpiperidin-1-yl)-5-(2-((2-fluorophenoxy)methyl)chroman-6-yl)-2,6-dimethylpyridin-3-yl)acetic acid (8.5 mg, 0.014 mmol, 76% yield) as a white solid. LCMS (M+H)=605.1.

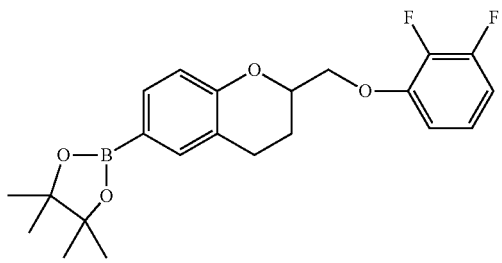 [SMILES: CC1(C)OB(c2ccc3c(c2)CCC(COc2cccc(F)c2F)O3)OC1(C)C]

2-(2-((2,3-Difluorophenoxy)methyl)chroman-6-yl)-4,4,5,5-tetramethyl-1,3,2-dioxaborolane A mixture of 2,3-difluorophenol (53.8 mg, 0.414 mmol), triphenylphosphine (108 mg, 0.414 mmol) in THF (2 mL) at rt was added (Z)-diisopropyl diazene-1,2-dicarboxylate (0.080 mL, 0.414 mmol) and stirred at rt for 10 min, then (6-(4,4,5,5-tetramethyl-1,3,2-dioxaborolan-2-yl)chroman-2-yl)methanol (60 mg, 0.207 mmol) was added and stirred at rt for 1 h. It was then concentrated and purified by biotage, eluting with 25% EtOAc/hexane to obtain 2-(2-((2,3-difluorophenoxy)methyl)chroman-6-yl)-4,4,5,5-tetramethyl-1,3,2-dioxaborolane (60 mg, 0.149 mmol, 72.1% yield) as a colorless oil. LCMS (M+Na)=424.8. $^1$H NMR (400 MHz, CDCl$_3$) δ 7.68-7.53 (m, 2H), 7.13-6.92 (m, 2H), 6.81-6.67 (m, 2H), 4.52-4.40 (m, 1H), 4.39-4.28 (m, 1H), 4.26-4.12 (m, 1H), 3.02-2.68 (m, 2H), 2.23 (d, J=13.0 Hz, 1H), 2.05-1.89 (m, 1H), 1.36 (s, 12H).

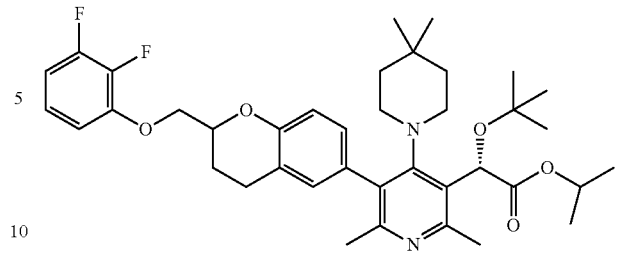

(2S)-Isopropyl 2-tert-butoxy-2-(5-(2-((2,3-difluorophenoxy)methyl)chroman-6-yl)-4-(4,4-dimethylpiperidin-1-yl)-2,6-dimethylpyridin-3-yl)acetate A mixture of (S)-isopropyl 2-(5-bromo-4-(4,4-dimethylpiperidin-1-yl)-2,6-dimethylpyridin-3-yl)-2-(tert-butoxy) acetate (50 mg, 0.107 mmol), 2-(2-((2,3-difluorophenoxy)methyl)-chroman-6-yl)-4,4,5,5-tetramethyl-1,3,2-dioxaborolane (55.7 mg, 0.138 mmol) in DMF (2 mL) was vacuum, back-filled with N$_2$ for 3 times. It was then added Pd(Ph$_3$P)$_4$ (24.61 mg, 0.021 mmol) and heated at 85° C. for 16 h. It was then diluted with EtOAc, washed with water. The organic was dried over MgSO$_4$, filtered and concentrated to obtain 30 mg of an oil, which was then purified by biotage, eluting with 25% EtOac/hexane to isolate (2S)-isopropyl 2-(tert-butoxy)-2-(5-(2-((2,3-difluorophenoxy) methyl)chroman-6-yl)-4-(4,4-dimethylpiperidin-1-yl)-2,6-dimethylpyridin-3-yl)acetate (12 mg, 0.018 mmol, 16.95% yield) as a white solid. LCMS (M+H)=665.2.

Example 41

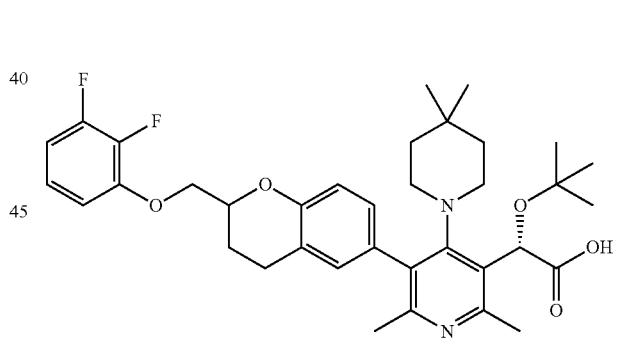

(2S)-2-tert-Butoxy-2-(5-(2-((2,3-difluorophenoxy) methyl)chroman-6-yl)-4-(4,4-dimethylpiperidin-1-yl)-2,6-dimethylpyridin-3-yl)acetic acid A mixture of (2S)-isopropyl 2-(tert-butoxy)-2-(5-(2-((2,3-difluorophenoxy)methyl)chroman-6-yl)-4-(4,4-dimethylpiperidin-1-yl)-2,6-dimethylpyridin-3-yl)acetate (50 mg, 0.075 mmol), KOH (21.10 mg, 0.376 mmol) in ethanol (2 mL) and water (0.2 mL) was reflux for 16 h. It was then submit to purified to obtain (2S)-2-(tert-butoxy)-2-(5-(2-((2,3-difluorophenoxy)methyl)chroman-6-yl)-4-(4,4-dimethyl-piperidin-1-yl)-2,6-dimethylpyridin-3-yl)acetic acid (45 mg, 0.072 mmol, 96% yield) as a white solid. LCMS (M+H)=623.1.

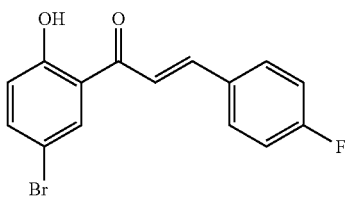 [SMILES: O=C(/C=C/c1ccc(F)cc1)c1cc(Br)ccc1O]

(E)-1-(5-Bromo-2-hydroxyphenyl)-3-(4-fluorophenyl)prop-2-en-1-one

A mixture of 1-(5-bromo-2-hydroxyphenyl)ethanone (1 g, 4.65 mmol), 4-fluorobenzaldehyde (0.540 mL, 5.12 mmol), NaOH (0.558 g, 13.95 mmol) in NaOH (0.558 g, 13.95 mmol) was stirred at rt for 16 h. It was then added 1 N HCl until a yellow ppt was formed. It was then filtered and washed with water. It was then filtered and dried to obtain (E)-1-(5-bromo-2-hydroxyphenyl)-3-(4-fluorophenyl)prop-2-en-1-one (1.45 g, 4.52 mmol, 97% yield). $^1$H NMR (400 MHz, CDCl$_3$) δ 12.72 (s, 1H), 8.02 (s, 1H), 7.94 (d, J=15.7 Hz, 1H), 7.75-7.68 (m, 2H), 7.60 (d, J=8.8 Hz, 1H), 7.52 (d, J=15.4 Hz, 1H), 7.18 (t, J=8.4 Hz, 2H), 6.97 (d, J=8.8 Hz, 1H).

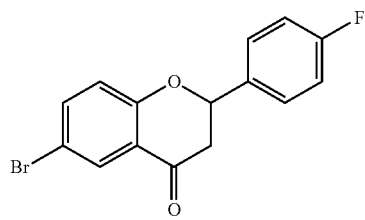 [SMILES: O=C1CC(c2ccc(F)cc2)Oc2ccc(Br)cc21]

6-Bromo-2-(4-fluorophenyl)chroman-4-one

To a solution of (E)-1-(5-bromo-2-hydroxyphenyl)-3-(4-fluorophenyl)prop-2-en-1-one (1.45 g, 4.52 mmol) in EtOH (10 mL), HCl (0.3 mL, 9.87 mmol) was added. The resulting orange slurry was refluxed for 16 h. It was cooled to rt and then filtered. The solid was washed with water to obtain 6-bromo-2-(4-fluorophenyl)chroman-4-one (1.4 g, 4.36 mmol, 97% yield). $^1$H NMR (400 MHz, CDCl$_3$) δ 8.07 (s, 1H), 7.62 (d, J=7.3 Hz, 1H), 7.48 (dd, J=8.2, 5.7 Hz, 2H), 7.19-7.11 (m, 2H), 6.98 (d, J=8.8 Hz, 1H), 5.48 (d, J=10.8 Hz, 1H), 3.15-2.84 (m, 2H). LCMS (M+H)=322.1.

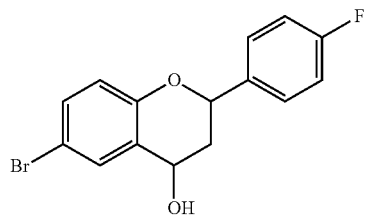 [SMILES: OC1CC(c2ccc(F)cc2)Oc2ccc(Br)cc21]

6-Bromo-2-(4-fluorophenyl)chroman-4-ol

A mixture of 6-bromo-2-(4-fluorophenyl)chroman-4-one (400 mg, 1.246 mmol) in MeOH (10 mL) was added NaBH$_4$ (47.1 mg, 1.246 mmol) and stirred at rt for 1 h. It was then quenched with NH$_4$Cl, extracted with EtOAc. The organic was washed with water, dried over MgSO$_4$, filtered and concentrated. It was then purify by biotage, eluting with 20% EtOAc/hexane to obtain 6-bromo-2-(4-fluorophenyl)chroman-4-ol (350 mg, 1.083 mmol, 87% yield). $^1$H NMR (400 MHz, CDCl$_3$) δ 7.68 (s, 1H), 7.43 (dd, J=7.9, 5.5 Hz, 2H), 7.32 (d, J=8.8 Hz, 1H), 7.12 (t, J=8.4 Hz, 2H), 6.79 (d, J=8.6 Hz, 1H), 5.17 (d, J=11.5 Hz, 1H), 5.15-5.06 (m, 1H), 2.52 (dd, J=13.2, 6.1 Hz, 1H), 2.19-2.09 (m, 1H), 1.81 (d, J=8.3 Hz, 1H).

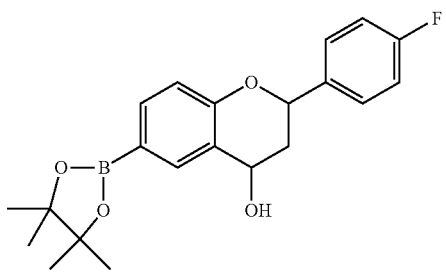 [SMILES: CC1(C)OB(c2ccc3c(c2)C(O)CC(c2ccc(F)cc2)O3)OC1(C)C]

2-(4-Fluorophenyl)-6-(4,4,5,5-tetramethyl-1,3,2-dioxaborolan-2-yl)chroman-4-ol

A mixture of 6-bromo-2-(4-fluorophenyl)chroman-4-ol (350 mg, 1.083 mmol), bis(pinacolato)diboron (413 mg, 1.625 mmol), potassium acetate (319 mg, 3.25 mmol) in Dioxane (10 mL) was degassed three times and then filled with N2. It was then added 1,1'-bis(diphenylphosphino)ferrocene-palladium(II)dichloride dichloromethane complex (88 mg, 0.108 mmol) and heated at 85° C. for 16 h. It was then quenched with water, extracted with EtOAc. The organic layer was dried over MgSO$_4$, filtered and concentrated. It was then purified by biotage, eluting with 50% EtOAc/hexane to obtain 2-(4-fluorophenyl)-6-(4,4,5,5-tetramethyl-1,3,2-dioxaborolan-2-yl)chroman-4-ol (250 mg, 62%). $^1$H NMR (400 MHz, CDCl$_3$) δ 8.01 (s, 1H), 7.75-7.63 (m, 1H), 7.50-7.38 (m, 2H), 7.11 (t, J=8.4 Hz, 2H), 6.91 (d, J=8.1 Hz, 1H), 5.25-5.05 (m, 2H), 2.54 (dd, J=13.2, 6.1 Hz, 1H), 2.25-2.08 (m, 1H), 1.87 (d, J=7.3 Hz, 1H), 1.37 (s, 12H).

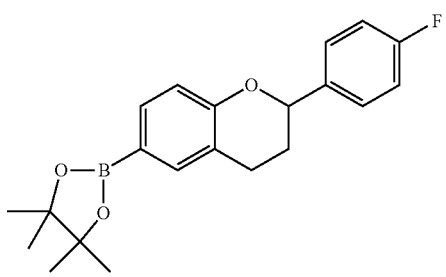 [SMILES: CC1(C)OB(c2ccc3c(c2)CCC(c2ccc(F)cc2)O3)OC1(C)C]

2-(2-(4-Fluorophenyl)chroman-6-yl)-4,4,5,5-tetramethyl-1,3,2-dioxaborolane

A mixture of 2-(4-fluorophenyl)-6-(4,4,5,5-tetramethyl-1,3,2-dioxaborolan-2-yl)chroman-4-ol (300 mg, 0.810 mmol) in DCM (10 mL) was added triethylsilane (1.035 mL, 6.48 mmol) and TFA (1.998 mL, 25.9 mmol) and stirred at rt for 2 h. It was then diluted with EtOAc, washed with NaHCO₃, water. The organic was dried over MgSO₄, filtered and concentrated to obtain 2-(2-(4-fluorophenyl)chroman-6-yl)-4,4,5,5-tetramethyl-1,3,2-dioxaborolane (200 mg, 0.565 mmol, 69.7% yield) as a white solid. ¹H NMR (400 MHz, CDCl₃) δ 7.66-7.56 (m, 2H), 7.46-7.37 (m, 2H), 7.14-7.06 (m, 2H), 6.92 (d, J=7.8 Hz, 1H), 5.10 (d, J=10.5 Hz, 1H), 3.00 (ddd, J=16.8, 10.9, 5.9 Hz, 1H), 2.88-2.77 (m, 1H), 2.23 (d, J=15.2 Hz, 1H), 2.15-2.00 (m, 1H), 1.42-1.33 (m, 12H).

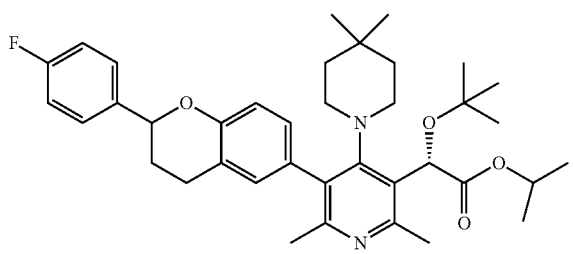 [SMILES: Cc1nc(C)c([C@H](OC(C)(C)C)C(=O)OC(C)C)c(N2CCC(C)(C)CC2)c1-c1ccc2c(c1)CCC(c1ccc(F)cc1)O2]

(2S)-Isopropyl 2-tert-butoxy-2-(4-(4,4-dimethylpiperidin-1-yl)-5-(2-(4-fluorophenyl)chroman-6-yl)-2,6-dimethylpyridin-3-yl)acetate A mixture of (S)-isopropyl 2-(5-bromo-4-(4,4-dimethylpiperidin-1-yl)-2,6-dimethylpyridin-3-yl)-2-(tert-butoxy)acetate (50 mg, 0.107 mmol), potassium phosphate tribasic (170 mg, 0.799 mmol), 2-(2-(4-fluorophenyl)chroman-6-yl)-4,4,5,5-tetramethyl-1,3,2-dioxaborolane (56.6 mg, 0.160 mmol) in dioxane (3 mL) was vacuum, back-filled with N₂ for 3 times. It was then added Pd(Ph₃P)₄ (24.61 mg, 0.021 mmol) and heated at 85° C. for 16 h. It was then diluted with EtOAc, washed with water. The organic was dried over MgSO₄, filtered and concentrated to obtain 50 mg of an oil, which was then purified by biotage, eluting with 25% EtOAc/hexane to isolate (2S)-isopropyl 2-(tert-butoxy)-2-(4-(4,4-dimethylpiperidin-1-yl)-5-(2-(4-fluorophenyl)chroman-6-yl)-2,6-dimethylpyridin-3-yl)acetate (50 mg, 0.081 mmol, 76% yield) as a white solid. LCMS (M+H)=617.1.

Example 42

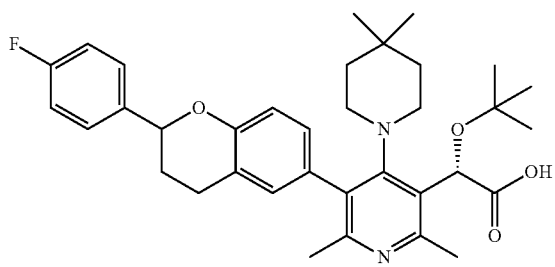 [SMILES: Cc1nc(C)c([C@H](OC(C)(C)C)C(=O)O)c(N2CCC(C)(C)CC2)c1-c1ccc2c(c1)CCC(c1ccc(F)cc1)O2]

(2S)-2-tert-Butoxy-2-(4-(4,4-dimethylpiperidin-1-yl)-5-(2-(4-fluorophenyl)chroman-6-yl)-2,6-dimethylpyridin-3-yl)acetic acid A mixture of (2S)-isopropyl 2-(tert-butoxy)-2-(4-(4,4-dimethylpiperidin-1-yl)-5-(2-(4-fluorophenyl)chroman-6-yl)-2,6-dimethylpyridin-3-yl)acetate (50 mg, 0.081 mmol), KOH (22.74 mg, 0.405 mmol) in EtOH (3 mL), water (0.3 mL) was refluxed for 16 h. It was then cooled to rt and purified by prep HPLC to obtain (2S)-2-(tert-butoxy)-2-(4-(4,4-dimethylpiperidin-1-yl)-5-(2-(4-fluorophenyl)chroman-6-yl)-2,6-dimethylpyridin-3-yl)acetic acid (29.7 mg, 0.052 mmol, 63.7% yield) as a white solid. LCMS (M+H)=575.3.

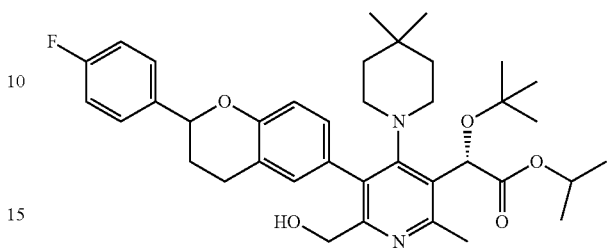

(2S)-Isopropyl 2-tert-butoxy-2-(4-(4,4-dimethylpiperidin-1-yl)-5-(2-(4-fluorophenyl)chroman-6-yl)-6-(hydroxymethyl)-2-methylpyridin-3-yl)acetate A mixture of (S)-isopropyl 2-(5-bromo-4-(4,4-dimethylpiperidin-1-yl)-6-(hydroxymethyl)-2-methylpyridin-3-yl)-2-(tert-butoxy)acetate (50 mg, 0.103 mmol), potassium phosphate tribasic (164 mg, 0.772 mmol), 2-(2-(4-fluorophenyl)chroman-6-yl)-4,4,5,5-tetramethyl-1,3,2-dioxaborolane (54.7 mg, 0.154 mmol) in dioxane (3 mL) was vacuum, back-filled with N₂ for 3 times. It was then added Pd(Ph₃P)₄ (23.80 mg, 0.021 mmol) and heated at 85° C. for 16 h. It was then diluted with EtOAc, washed with water. The organic was dried over MgSO₄, filtered and concentrated to obtain 50 mg of an oil, which was then purified by biotage, eluting with 25% EtOAc/hexane to isolate (2S)-isopropyl 2-(tert-butoxy)-2-(4-(4,4-dimethylpiperidin-1-yl)-5-(2-(4-fluorophenyl)chroman-6-yl)-6-(hydroxymethyl)-2-methylpyridin-3-yl)acetate (50 mg, 0.079 mmol, 77% yield) as a white solid. LCMS (M+H)=633.1.

Example 43

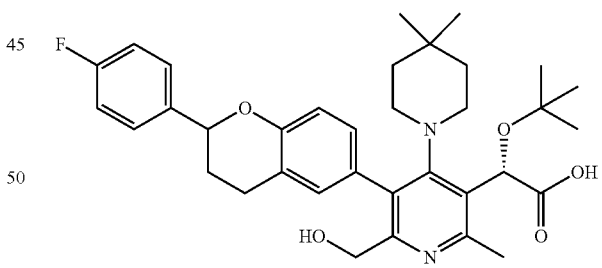

(2S)-2-tert-Butoxy-2-(4-(4,4-dimethylpiperidin-1-yl)-5-(2-(4-fluorophenyl)chroman-6-yl)-6-(hydroxymethyl)-2-methylpyridin-3-yl)acetic acid A mixture of (2S)-isopropyl 2-(tert-butoxy)-2-(4-(4,4-dimethylpiperidin-1-yl)-5-(2-(4-fluorophenyl)-chroman-6-yl)-6-(hydroxymethyl)-2-methylpyridin-3-yl)acetate (50 mg, 0.079 mmol), KOH (22.17 mg, 0.395 mmol) in EtOH (3 mL), water (0.3 mL) was refluxed for 16 h. It was then cooled to rt and purified by prep HPLC to obtain (2S)-2-(tert-butoxy)-2-(4-(4,4-dimethylpiperidin-1-yl)-5-(2-(4-fluorophenyl)chroman-6-yl)-6-(hydroxymethyl)-2-methylpyridin-3-yl)acetic acid (19 mg, 0.032 mmol, 40.7% yield) as a white solid. LCMS (M+1)=591.3.

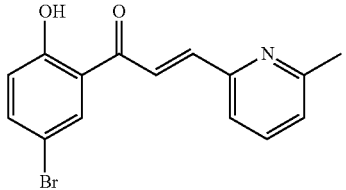 [SMILES: Cc1cccc(/C=C/C(=O)c2cc(Br)ccc2O)n1]

(E)-1-(5-Bromo-2-hydroxyphenyl)-3-(6-methylpyridin-2-yl)prop-2-en-1-one

A mixture of 6-methyl-2-pyridinecarboxaldehyde (0.620 g, 5.12 mmol), 1-(5-bromo-2-hydroxyphenyl)ethanone (1 g, 4.65 mmol) and NaOH (0.558 g, 13.95 mmol) in EtOH (15 mL) was stirred at rt for 16 h. It was then concentrated and adjusted pH=5 using 1 N HCl to form a yellow ppt. It was then filtered and washed with water, dried to obtain (E)-1-(5-bromo-2-hydroxyphenyl)-3-(6-methylpyridin-2-yl)prop-2-en-1-one (1.1 g, 3.46 mmol, 74.3% yield). $^1$H NMR (400 MHz, CDCl$_3$) δ 12.73 (s, 1H), 8.23-8.12 (m, 2H), 7.88 (d, J=14.7 Hz, 1H), 7.68 (t, J=7.7 Hz, 1H), 7.61 (d, J=8.8 Hz, 1H), 7.35 (d, J=7.6 Hz, 1H), 7.23 (d, J=8.1 Hz, 1H), 6.97 (d, J=8.6 Hz, 1H), 2.68 (s, 3H).

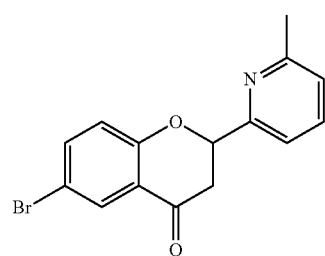 [SMILES: Cc1cccc(C2CC(=O)c3cc(Br)ccc3O2)n1]

6-Bromo-2-(6-methylpyridin-2-yl)chroman-4-one

To a solution of (E)-1-(5-bromo-2-hydroxyphenyl)-3-(6-methylpyridin-2-yl)prop-2-en-1-one (1.45 g, 4.56 mmol) in EtOH (10 mL) was added concentrated HCl (0.3 mL, 9.87 mmol). The resulting orange slurry was refluxed for 16 h. It was then concentrated temperature and then filtered. The solid was washed with water to obtain 6-bromo-2-(6-methylpyridin-2-yl)chroman-4-one (0.45 g, 1.414 mmol, 31.0% yield) as a yellow solid. $^1$H NMR (400 MHz, CDCl$_3$) δ 8.05 (d, J=2.5 Hz, 1H), 7.72-7.69 (m, 1H), 7.60 (dd, J=8.8, 2.8 Hz, 1H), 7.39 (d, J=7.5 Hz, 1H), 7.17 (d, J=7.5 Hz, 1H), 7.01 (d, J=8.8 Hz, 1H), 5.57 (dd, J=11.7, 3.6 Hz, 1H), 3.28-3.08 (m, 2H), 2.59 (s, 3H).

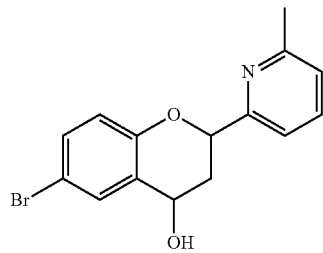 [SMILES: Cc1cccc(C2CC(O)c3cc(Br)ccc3O2)n1]

6-Bromo-2-(6-methylpyridin-2-yl)chroman-4-ol

A mixture of 6-bromo-2-(6-methylpyridin-2-yl)chroman-4-one (450 mg, 1.414 mmol) in MeOH (3 mL) was added MeOH (3 mL) and stirred at rt for 1 h. It was then quenched with water, extracted with EtOAc, dried over MgSO$_4$, filtered and concentrated to obtain 6-bromo-2-(6-methylpyridin-2-yl)chroman-4-ol (400 mg, 1.249 mmol, 88% yield) as an oil. $^1$H NMR (400 MHz, CDCl$_3$) δ 7.73-7.59 (m, 2H), 7.42 (d, J=7.6 Hz, 1H), 7.25 (s, 1H), 7.13 (d, J=7.8 Hz, 1H), 6.75 (d, J=8.6 Hz, 1H), 5.49-5.39 (m, 1H), 4.98-4.87 (m, 1H), 4.69 (d, J=8.1 Hz, 1H), 2.77 (dt, J=14.2, 5.2 Hz, 1H), 2.55 (s, 3H), 2.41 (dt, J=13.9, 6.6 Hz, 1H).

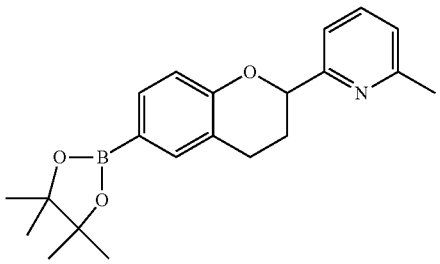

2-Methyl-6-(6-(4,4,5,5-tetramethyl-1,3,2-dioxaborolan-2-yl)chroman-2-yl)pyridine A mixture of 2-(6-methylpyridin-2-yl)-6-(4,4,5,5-tetramethyl-1,3,2-dioxaborolan-2-yl)chroman-4-ol (150 mg, 0.408 mmol) in DCM (5 mL) was added triethylsilane (0.522 mL, 3.27 mmol), TFA (1.007 mL, 13.07 mmol) and stirred at rt for 16 h. It was then added NaHCO$_3$ to adjusted pH around 8. It was then extracted with EtOAc. The organic was dried over MgSO$_4$, filtered and concentrated to obtain an oil, which was then purified by biotage, eluting with 0-50% EtOAc/hexane to obtain 2-methyl-6-(6-(4,4,5,5-tetramethyl-1,3,2-dioxaborolan-2-yl)chroman-2-yl)pyridine (67 mg, 0.191 mmol, 46.7% yield) as a white solid. $^1$H NMR (400 MHz, CDCl$_3$) δ 7.65-7.57 (m, 3H), 7.34 (d, J=7.3 Hz, 1H), 7.09 (d, J=7.6 Hz, 1H), 6.96 (d, J=7.8 Hz, 1H), 5.22 (d, J=10.3 Hz, 1H), 3.04-2.88 (m, 1H), 2.81-2.68 (m, 1H), 2.58 (s, 3H), 2.44 (d, J=13.2 Hz, 1H), 2.19-2.02 (m, 1H), 1.36 (s, 12H).

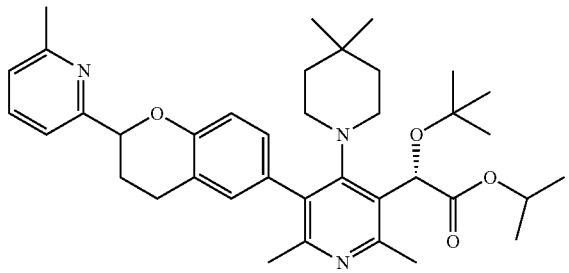 [SMILES: Cc1cccc(C2CCc3cc(-c4c(C)nc(C)c([C@H](OC(C)(C)C)C(=O)OC(C)C)c4N4CCC(C)(C)CC4)ccc3O2)n1]

(2S)-Isopropyl 2-tert-butoxy-2-(4-(4,4-dimethylpiperidin-1-yl)-2,6-dimethyl-5-(2-(6-methylpyridin-2-yl)chroman-6-yl)pyridin-3-yl)acetate A mixture of (S)-isopropyl 2-(5-bromo-4-(4,4-dimethylpiperidin-1-yl)-2,6-dimethylpyridin-3-yl)-2-(tert-butoxy)

acetate (30 mg, 0.064 mmol), 2-methyl-6-(6-(4,4,5,5-tetramethyl-1,3,2-dioxaborolan-2-yl)chroman-2-yl)pyridine (33.7 mg, 0.096 mmol) in dioxane (3 mL), water (0.3 mL) was vacuum, back-filled with $N_2$ for 3 times. It was then added $Pd(Ph_3P)_4$ (14.77 mg, 0.013 mmol) and heated at 85° C. for 16 h. It was then diluted with EtOAc, washed with water. The organic was dried over $MgSO_4$, filtered and concentrated to obtain 50 mg of an oil, which was then purified by biotage, eluting with 25% EtOAc/hexane to isolate (2S)-isopropyl 2-(tert-butoxy)-2-(4-(4,4-dimethylpiperidin-1-yl)-2,6-dimethyl-5-(2-(6-methylpyridin-2-yl)chroman-6-yl)pyridin-3-yl)acetate (20 mg, 0.033 mmol, 51.0% yield) as a white solid. LCMS (M+H)=614.1.

pyridine (32.6 mg, 0.093 mmol) in dioxane (3 mL), water (0.3 mL) was vacuum, back-filled with $N_2$ for 3 times. It was then added $Pd(Ph_3P)_4$ (14.28 mg, 0.012 mmol) and heated at 85° C. for 16 h. It was then diluted with EtOAc, washed with water. The organic was dried over $MgSO_4$, filtered and concentrated to obtain 50 mg of an oil, which was then purified by biotage, eluting with 25% EtOAc/hexane to isolate (2S)-isopropyl 2-(tert-butoxy)-2-(4-(4,4-dimethylpiperidin-1-yl)-6-(hydroxymethyl)-2-methyl-5-(2-(6-methylpyridin-2-yl)chroman-6-yl)pyridin-3-yl)acetate (30 mg, 0.048 mmol, 77% yield) as a white solid. LCMS (M+H)=630.2.

Example 44

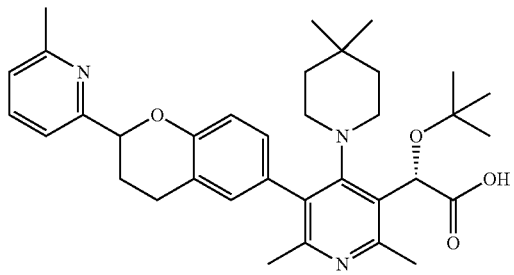 [SMILES: Cc1cccc(C2CCc3cc(-c4c(C)nc(C)c([C@H](OC(C)(C)C)C(=O)O)c4N4CCC(C)(C)CC4)ccc3O2)n1]

(2S)-2-tert-Butoxy-2-(4-(4,4-dimethylpiperidin-1-yl)-2,6-dimethyl-5-(2-(6-methylpyridin-2-yl)chroman-6-yl)pyridin-3-yl)acetic acid A mixture of (2S)-isopropyl 2-(tert-butoxy)-2-(4-(4,4-dimethylpiperidin-1-yl)-2,6-dimethyl-5-(2-(6-methylpyridin-2-yl)chroman-6-yl)pyridin-3-yl)acetate (35 mg, 0.057 mmol) and KOH (32.0 mg, 0.570 mmol) in ethanol (2 mL) was refluxed for 16 h. It was filtered and purified by prep HPLC to obtain (2S)-2-(tert-butoxy)-2-(4-(4,4-dimethylpiperidin-1-yl)-2,6-dimethyl-5-(2-(6-methylpyridin-2-yl)chroman-6-yl)pyridin-3-yl)acetic acid (19.9 mg, 0.035 mmol, 61.0% yield) as a white solid. LCMS (M+H)=572.1.

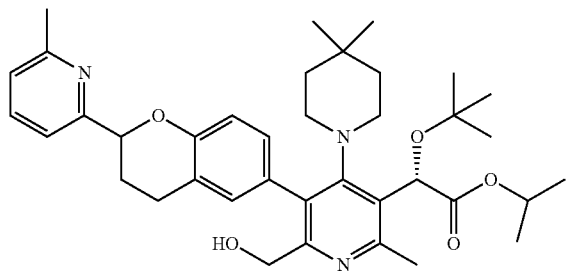 [SMILES: Cc1cccc(C2CCc3cc(-c4c(CO)nc(C)c([C@H](OC(C)(C)C)C(=O)OC(C)C)c4N4CCC(C)(C)CC4)ccc3O2)n1]

(2S)-Isopropyl 2-tert-butoxy-2-(4-(4,4-dimethylpiperidin-1-yl)-6-(hydroxymethyl)-2-methyl-5-(2-(6-methylpyridin-2-yl)chroman-6-yl)pyridin-3-yl)acetate A mixture of (S)-isopropyl 2-(5-bromo-4-(4,4-dimethylpiperidin-1-yl)-6-(hydroxymethyl)-2-methylpyridin-3-yl)-2-(tert-butoxy)acetate (30 mg, 0.062 mmol), 2-methyl-6-(6-(4,4,5,5-tetramethyl-1,3,2-dioxaborolan-2-yl)chroman-2-yl)

Example 45

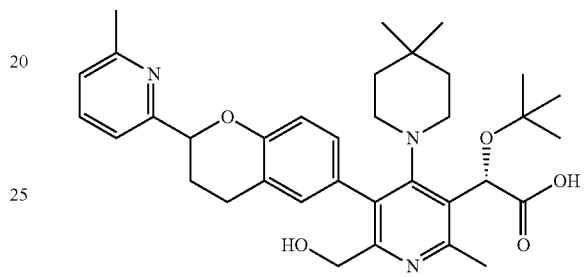

(2S)-2-tert-Butoxy-2-(4-(4,4-dimethylpiperidin-1-yl)-6-(hydroxymethyl)-2-methyl-5-(2-(6-methylpyridin-2-yl)chroman-6-yl)pyridin-3-yl)acetic acid A mixture of (2S)-isopropyl 2-(tert-butoxy)-2-(4-(4,4-dimethylpiperidin-1-yl)-6-(hydroxymethyl)-2-methyl-5-(2-(6-methylpyridin-2-yl)chroman-6-yl)pyridin-3-yl)acetate (30 mg, 0.048 mmol), KOH (2.67 mg, 0.048 mmol) in ethanol (2 mL), water (0.2 mL) was refluxed for 16 h. It was then filtered and purified by prep HPLC to obtain (2S)-2-(tert-butoxy)-2-(4-(4,4-dimethylpiperidin-1-yl)-6-(hydroxymethyl)-2-methyl-5-(2-(6-methylpyridin-2-yl)chroman-6-yl)pyridin-3-yl)acetic acid (21.4 mg, 0.036 mmol, 76% yield) as a white solid. LCMS (M+H)=588.1.

Biological Methods

Inhibition of HIV Replication

A recombinant NL-RLuc proviral clone was constructed in which a section of the nef gene from NL4-3 was replaced with the *Renilla* Luciferase gene. This virus is fully infectious and can undergo multiple cycles of replication in cell culture. In addition, the luciferous reporter provides a simple and easy method for quantitating the extent of virus growth and consequently, the antiviral activity of test compounds. The plasmid pNLRLuc contains the proviral NL-Rluc DNA cloned into pUC18 at the PvuII site. The NL-RLuc virus was prepared by transfection of 293T cells with the plasmid pNLRLuc. Transfections were performed using the LipofectAMINE PLUS kit from Invitrogen (Carlsbad, Calif.) according to the manufacturer and the virus generated was titered in MT-2 cells. For susceptibility analyses, the titrated virus was used to infect MT-2 cells in the presence of compound, and after 5 days of incubation, cells were processed and quantitated for virus growth by the amount of expressed luciferase. Assay media was RPMI 1640 supplemented with 10% heat inactivated fetal bovine serum (FBS), 100 units/ml penicillin G/100 units/ml streptomycin, 10 mM HEPES buffer pH 7.55 and 2 mM L-glutamine. The results from at least 2 experiments were used to calculate the $EC_{50}$ values. Luciferase was quantitated using the Dual Luciferase kit from Promega (Madison, Wis.). Susceptibility of viruses to compounds was determined by incubation in the presence of serial dilutions of the compound. The 50% effective concentration ($EC_{50}$) was calculated by using the exponential form of the median effect equation where $(Fa)=1/[1+(ED_{50}/\text{drug conc.})^m]$ (Johnson V A, Byington R T. Infectivity Assay. In *Techniques in HIV Research*. ed. Aldovini A, Walker B D. 71-76. New York: Stockton Press. 1990). Results are shown in Table 1.

TABLE 1

| Example | $EC_{50}$ μM |
| --- | --- |
| 1 | 0.047 |
| 2 | 0.073 |
| 3 | 0.101 |
| 4 | 0.233 |
| 5 | 0.056 |
| 6 | 66.012 |
| 7 | 0.288 |
| 8 | 7.065 |
| 9 | 0.087 |
| 10 | 0.307 |
| 11 | 1.675 |
| 12 | 4.963 |
| 13 | 0.012 |
| 14 | 0.006 |
| 15 | 0.014 |
| 16 | 0.006 |
| 17 | 0.024 |
| 18 | 0.504 |
| 19 | 0.240 |
| 20 | 0.087 |
| 21 | 0.030 |
| 22 | 0.053 |
| 23 | 0.017 |
| 24 | 0.010 |
| 25 | 0.005 |
| 26 | 0.010 |
| 27 | 0.006 |
| 28 | 0.002 |
| 29 | 0.005 |
| 30 | 0.005 |
| 31 | 0.003 |
| 32 | 0.002 |
| 33 | 0.007 |
| 34 | 0.002 |
| 35 | 0.003 |
| 36 | 0.002 |
| 37 | 0.001 |
| 38 | 0.004 |
| 39 | 0.003 |
| 40 | 0.004 |
| 41 | 0.003 |
| 42 | 0.007 |
| 43 | 0.007 |
| 44 | 0.008 |
| 45 | 0.007 |

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

We claim:
1. A compound of Formula I

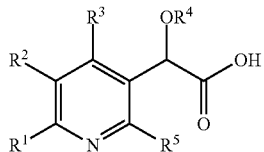

or a pharmaceutically acceptable salt thereof wherein:
$R^1$ is selected from hydrogen, $C_{1-6}$alkyl, $C_{3-7}$cycloalkyl, or hydroxy$C_{1-6}$alkyl;
$R^2$ is selected from indanyl, tetrahydronaphthalinyl, indolyl, indolinyl, isoindolinyl, isoindolinonyl, benzofuranyl, benzothiophenyl, benzoimidazolonyl, chromanyl, quinolinyl, quinolinonyl, isoquinolinyl, tetrahydroisoquinolinonyl, dihydrobenzodioxinyl or benzoxazinyl, and is substituted with 0-1 $R^6$ substituent and 0-3 halo or $C_{1-6}$alkyl substituents;
$R^3$ is selected from azetidinyl, pyrrolidinyl, piperidinyl, piperazinyl, morpholinyl, homopiperidinyl, homopiperazinyl, or homomorpholinyl, and is substituted with 0-3 substituents selected from cyano, halo, $C_{1-6}$alkyl, halo$C_{1-6}$alkyl, $C_{1-6}$alkoxy, and halo$C_{1-6}$alkoxy;
$R^4$ is selected from $C_{1-6}$alkyl or halo$C_{1-6}$alkyl;
$R^5$ is $C_{1-6}$alkyl;
$R^6$ is selected from $(Ar^1)C_{1-6}$alkyl, $((Ar^1)O)C_{1-6}$alkyl, $(Ar^1)C_{2-10}$alkenyl, hydroxy, $C_{1-6}$alkoxy, $(Ar^1)O$, $(Ar^1)SO_2$, $(Ar^1)CO$, carboxy, or $Ar^1$; wherein $Ar^1$ is selected from phenyl, pyridinyl, or thiazolyl, and is substituted with 0-3 substituents selected from cyano, halo, $C_{1-6}$alkyl, halo$C_{1-6}$alkyl, $C_{1-6}$alkoxy, and halo$C_{1-6}$alkoxy;
or a pharmaceutically acceptable salt thereof.

2. A compound or salt of claim 1 wherein $R^2$ is selected from tetrahydronaphthalinyl, isoindolinyl, isoindolinonyl, chromanyl, quinolinyl, quinolinonyl, isoquinolinyl and tetrahydroisoquinolinonyl, and is substituted with 0-1 $R^6$ substituent and 0-3 halo or $C_{1-6}$alkyl substituents.

3. A compound or salt of claim 2 where $R^2$ is chromanyl substituted with 0-1 $R^6$ substituent and 0-3 halo or $C_{1-6}$alkyl substituents.

4. A compound or salt of claim 1 where $R^2$ has 1 $R^6$ substituent and 0-3 halo or $C_{1-6}$alkyl substituents.

5. A compound or salt of claim 1 where $R^3$ is piperidinyl substituted with 0-3 substituents selected from cyano, halo, $C_{1-6}$alkyl, halo$C_{1-6}$alkyl, $C_{1-6}$alkoxy, and halo$C_{1-6}$alkoxy.

6. A compound or salt of claim 1 where $R^6$ is selected from $(Ar^1)C_{1-6}$alkyl, $((Ar^1)O)C_{1-6}$alkyl, $(Ar^1)C_{2-10}$alkenyl.

7. A compound or salt of claim 1 where $R^6$ is selected from hydroxy, alkoxy, $(Ar^1)O$, $(Ar^1)SO_2$, $(Ar^1)CO$, or carboxy.

8. A composition useful for treating HIV infection comprising a compound or salt of claim 1 and a pharmaceutically acceptable carrier.

9. The composition of claim 8 further comprising a therapeutically effective amount at least one other agent used for treatment of AIDS or HIV infection selected from nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors, and a pharmaceutically acceptable carrier.

10. The composition of claim 9 wherein the other agent is dolutegravir.

11. A method for treating HIV infection comprising administering a compound of claim 1, or a pharmaceutically acceptable salt thereof, to a patient in need thereof.

12. The method of claim 11 further comprising administering a therapeutically effective amount of at least one other agent used for treatment of AIDS or HIV infection selected from nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors.

13. The method of claim 12 wherein the other agent is dolutegravir.

* * * * *